US010941398B2

(12) United States Patent
Heck et al.

(10) Patent No.: US 10,941,398 B2
(45) Date of Patent: Mar. 9, 2021

(54) SELECTING AND STABILIZING DSRNA CONSTRUCTS

(75) Inventors: Gregory R. Heck, Crystal Lake Park, MO (US); Tichafa R. I. Munyikwa, Ballwin, MO (US); Jean C. Goley, Saint Charles, MO (US); James K. Roberts, Chesterfield, MO (US); Scott C. Johnson, Wildwood, MO (US); Ty T. Vaughn, Imperial, MO (US)

(73) Assignee: Monsanto Technology LLC, St. Louis, MO (US)

(*) Notice: Subject to any disclaimer, the term of this patent is extended or adjusted under 35 U.S.C. 154(b) by 587 days.

(21) Appl. No.: 13/305,688

(22) Filed: Nov. 28, 2011

(65) Prior Publication Data

US 2012/0192317 A1 Jul. 26, 2012

Related U.S. Application Data

(62) Division of application No. 11/674,005, filed on Feb. 12, 2007, now abandoned.

(60) Provisional application No. 60/772,736, filed on Feb. 13, 2006.

(51) Int. Cl.
*C12N 15/82* (2006.01)
*C12N 15/113* (2010.01)
*C12N 15/11* (2006.01)

(52) U.S. Cl.
CPC .......... *C12N 15/113* (2013.01); *C12N 15/111* (2013.01); *C12N 15/8218* (2013.01); *C12N 15/8286* (2013.01); *C12N 2310/14* (2013.01); *C12N 2320/10* (2013.01); *Y02A 40/146* (2018.01)

(58) Field of Classification Search
CPC .................................................. C12N 15/113
USPC ....................................................... 800/285
See application file for complete search history.

(56) References Cited

U.S. PATENT DOCUMENTS

| 5,107,065 | A | 4/1992 | Shewmaker et al. |
| 5,231,020 | A | 7/1993 | Jorgensen et al. |
| 5,283,184 | A | 2/1994 | Jorgensen et al. |
| 5,759,829 | A | 6/1998 | Shewmaker et al. |
| 6,326,193 | B1 | 12/2001 | Liu et al. |
| 6,506,559 | B1 | 1/2003 | Fire et al. |
| 7,109,393 | B2 | 9/2006 | Gutterson |
| 7,507,811 | B2 | 3/2009 | Khvorova et al. |
| 2002/0048814 | A1 | 4/2002 | Oeller |
| 2003/0018993 | A1 | 1/2003 | Gutterson |
| 2003/0061626 | A1 | 3/2003 | Plaetinck et al. |
| 2003/0150017 | A1* | 8/2003 | Mesa ................. C07K 14/4354 800/279 |
| 2003/0175965 | A1 | 9/2003 | Lowe et al. |
| 2003/0237111 | A1* | 12/2003 | Baum ................. C07K 14/325 800/302 |
| 2004/0029283 | A1 | 2/2004 | Fillatti |
| 2004/0237138 | A1 | 11/2004 | Cheikh et al. |
| 2006/0272049 | A1* | 11/2006 | Waterhouse ..... C07K 14/43563 800/279 |
| 2009/0188005 | A1 | 7/2009 | Boukharov et al. |
| 2010/0122381 | A1 | 5/2010 | Buehler et al. |

FOREIGN PATENT DOCUMENTS

| CN | 1348376 A | 5/2002 |
| EP | 1 484 415 A3 | 2/2008 |
| WO | WO 94/01550 | 1/1994 |
| WO | WO 98/05770 | 2/1998 |
| WO | WO 99/49029 | 9/1999 |
| WO | WO 99/53050 | 10/1999 |
| WO | WO 00/051621 | 9/2000 |
| WO | WO 01/37654 | 5/2001 |
| WO | WO 2005/110068 | 11/2005 |
| WO | WO-2005110068 A2 * | 11/2005 ......... C12N 15/8279 |

OTHER PUBLICATIONS

Reynolds et al (2004) Nat. Biotechnol. 22: 326-330.*
Feinberg et al (2003) Science 301:1545-1547 and supplemental.*
Gordon et al. (2007 Nature Biotechnology 25:1231-1232).*
Feinberg et al Science (2003) 301:1545-1547.*
Dong et al. (2005) BMC 5:25 1-7.*
Reynolds et al Nat. Biotechnol. (2004) 22: 326-330.*
Leuhrsen et al Mol. Gen. Genet. (1991) 225: 81-93.*
Bucher et al. 2002, Current Biology 12:R85-86.*
Arizman et al., "E-RNAi: a web application to design optimized RNAi constructs," *Nucl. Acids Res.*, 33:W582-588, 2005.
Bakhetia et al., "RNA interference and plant parasitic nematodes," *Trends in Plant Science*, 10(8):362-267, 2005.
Bettencourt et al., "Hemolin gene silencing by ds-RNA injected into *Cecropia pupae* is lethal to next generation embryos," *Insect Mol. Biol.*, 11:267-271, 2002.
Bucher et al., "Parental RNAi in Tribolium (Coleoptera)," *Curr. Biol.*, 12:R85-R86, 2002.
Carthew, "Gene silencing by double-stranded RNA," *Curr. Opin. Cell Biology*, 13:244-248, 2001.
Cogoni et al., "Post-transcriptional gene silencing across kingdoms," *Curr. Opin. Genet Dev.*, 10:638-643, 2000.
Feinberg et al., "Transport of dsRNA into cells by the transmembrane protein SID-1," *Science*, 301:1545-1547, 2003.
Fire et al., "Potent and specific genetic interference by double-stranded RNA in *Caenorhabditis elegans*," *Nature*, 391:806-811, 1998.

(Continued)

*Primary Examiner* — Li Zheng
(74) *Attorney, Agent, or Firm* — Dentons Us LLP; Amanda Carmany-Rampey

(57) ABSTRACT

The invention provides methods for selecting nucleotide sequences that yield dsRNA-mediated gene suppression in a target organism and enable their uptake by the target organism. The invention further provides expression constructs that confer stabilized expression of such sequences in a transgenic host cell, and methods for their use. Also provided are organisms, cells and tissues prepared by a method of the invention.

39 Claims, 8 Drawing Sheets

Specification includes a Sequence Listing.

(56) References Cited

OTHER PUBLICATIONS

Kumar et al., "High-Throughput Selection of Effective RNAi Probes for Gene Silencing," *Genome Res.*, 13:2333-2340, 2003.
Reynolds et al., "Rational siRNA design for RNA interference ," *Nat. Biotechnol.*, 22:326-330, 2004.
Uhlirova et al., "Use of sindbis virus-mediated RNA interference to demonstrate a conserved role of broad-complex in insect metamorphosis," *Proc. Nat. Acad. Sci. USA*, 100:15607-15613, 2003.
Voinnet, "Non-cell autonomous RNA silencing," *FEBS Lett.*, 579:5858-5871, 2005.
Wassenegger et al., "RNA-directed de novo methylation of genomic sequences in plants," *Cell*, 76:567-576, 1994.
Wesley et al., "Construct design for efficient, effective and high-throughput gene silencing in plants," *Plant J.*, 27:581-590, 2001.
Winston et al., "Systemic RNAi in *C. elegans* requires the putative transmembrane protein SID-1," *Science*, 295:2456-2459, 2002.
Yuan et al., "siRNA selection server: an automated siRNA oligonucleotide prediction server," *Nucl. Acids Res.*, W130-W134, 2004.
Zilberman et al., "Role of *Arabidopsis* ARGONAUTE4 in RNA-directed DNA methylation triggered by inverted repeats," *Curr. Biol.*, 14(13):1214-1220, 2004.
Tomoyasu et al., "Exploring systemic RNA interference in insects: a genome-wide survey for RNAi genes in *Tribolium*," *Genome Bio*; 9:R10-R22; 2008.
Hu et al., "High efficiency transport of quantum dots into plant roots with the aid of silwet L-77," *Plant Physiology and Biochemistry* 48:703-709, 2010.

\* cited by examiner

FIG. 1A

```
              :    10     :    20     :    30     :    40     :    50
Pt49_1     AGAAAGAAGAGGTTCGAGAAACAGCTCACTCAGATTGATGGCACACTTTC
Pt49_2     CGTAAGAAGAGGTATGAGAAGCAGCTGGCGCAGATCGACGGCACATTATC
Cf49_1     AGGAAGAAAAGATTGGAACAGCAGCTGGCACAAACCGATGGGACATTATC
Cf49_2     CGCAAGAAGAGGTATGAAAAGCAGCTGGCGCAGATCGACGGCACACTATC
Gg49       CGTAAGAAGAGGTATGAGAAGCAGCTTGCACAGATAGATGGCACGTTGTC
Xl49       CGTAAGAAGCGATATGAGAAGCAGCTGGCCCAGATTGATGGCACGCTATC
Dr49       CGAAAGAAGCGATATGAGAAGCAACTCGCTCAGATAGATGGCACTCTTTC
Fr49       AGAAAGAAGCGCTATGAGAAACAGCTCGCCCAGATTGATGGAACACTGTC
Af49       AGGAAGAAGCGTTATGAGAAGCAGTTGACTCAGATCGATGGTACACTGTC
Cs49       CGAAAGAAGCGTTATGAGAAGCAACTGCAGAACGTGGACGGAACGCTGTC
Sp49       AGGAAGAAGAAGTATGAGAAGCAGCTGGCCCAAGTTGATGGAACCTTGAC
Dmag49     CGGAAGAAGAGGTATGAGAAGCAACTCCAGCAGATTGATGGCACTATTTC
Bm49       CGGAAGAAGAGATACGAGAAGCAACTTACTCAAATAGATGGGACCCTCAC
Ap49       CGTAAGAAACGGTATGAACAACAACTAGCGCAAATTGATGGTACCATGTT
Am49       AGAAAGAAACGTTATGAAAAACAATTGCAACAAATTGATGGTACACTCAC
Lm49       AGAAAGAAGCGATATGAAAAACAACTGCAACAGATGGATGGAACTTTATC
Ag49       CGGAAGAAGCGGTACGAGAAACAGCTACAGCAAATCGATGGCACACTTTC
Gm49       AAAAAAAAGCGCTTAGAAAAGCAATTGCAACAAATCGATGGCACTCTGTC
Dm49       AAAAAGAAGCGGCTGGAGAAGCAACTCCAGCAGATCGATGGCACCCTGTC
Lh49       AAGAAAAAGCGGTTTGAAAAACAACTTCAACACATTGATGGAACTCTGTC
Tc49       AGGAAGAAACGCTACGAAAAGCAGCTCCAGCAGATCGATGGCACCCTCAG
Dbal49     AAGAAGAAACGATTGGAAAAGACCCAACTACAAATAGATGGAACMCTTAC
Du49       AAGAAGAAACGATTGGAAAAGACCCAACTACAAATAGATGGAACCCTTAC
Db49       AAGAAGAAACGATTGGAAAAGACTCAACTACAAATAGATGGAACCCTTAC
Dz49       AAGAAGAAACGATTGGAAAAGACCCAACTACAAATAGATGGAACCCTTAC
Dv49       AAGAAGAAACGATTGGAAAAGACCCAACTACAAATAGATGGAACCCTTAC
a.a.        K  K  K  R  L  E  K  T  Q  L  Q  I  D  G  T  L  T
Reynolds   68576435445746887959643664333675784677768776637464
Scan seg.    0          2          4          6          8   .
            13%        22%*       43%*       62%*       67%*
                 1          3          5          7          9
                16%        97%*       39%       80%*S
```

FIG. 1B

```
                  :    60    :    70    :    80    :    90    :   100
Pt49_1     TACCATTGAGTTCCAGAGAGAAGCCCTGGAGAACTCACACACCAACACTG
Pt49_2     AACCATCGAGTTCCAGCGGGAGGCCCTGGAGAATGCCAACACCAACACCG
Cf49_1     CACCCTGGAGTTTCAGCGTGAGGCCATTGAGAATGCCACCACCAATGCAG
Cf49_2     AACCATCGAGTTTCAGCGGGAAGCCCTGGAGAATGCCAATACCAACACCG
Gg49       CACAATCGAATTTCAGAGGGAAGCCTTGGAGAATGCCAACACCAACACTG
Xl49       AACCATCGAATTCCAGAGGGAAGCCCTTGAAAATGCCAACACAAATACTG
Dr49       CACCATTGAGTTCCAGAGAGAAGCATTAGAAAATGCCAATACAAACACAG
Fr49       GACCATCGAGTTCCAGAGAGAAGCTTTAGAGAACGCCAACACCAGCACTGA
Af49       CACCATCGAGTTCCAGAGGGAAGCACTGGAGAATGCCAACACCAACACAG
Cs49       CACTGTTGAGTTCCAACTGGAAGCTTTACAAAATGCGCAATCAAATAAAC
Sp49       TACGATAGAAGCACAGAGGGAGGCGCTGGAGAATGCTAATACCAATGCAG
Dmag       AACTATTGAAATGCAAAGAGAAGCTTTGGAGGGAGCAAATACCAATACAG
Bm49       TCAGATTGAGGCCCAAAGGGAAGCGCTAGAAGGTGCCAATACCAATGCCC
Ap49       AACTATTGAACAACAGCGAGAGGCATTAGAAGGTGCTAACACAAATACAG
Am49       TACAATTGAAAGTCAAAGGGAAGCACTTGAATGTGCGAATACTAATACTG
Lm49       AACAATGGAGATGCAACGAGAAGCTCTTGAAGGAGCAAATACCAATACTG
Ag49       GACGATTGAAATGCAGCGAGAGGCGCTGGAGAATGCGAACACAAACGCCG
Gm49       AACAATTGAAATGCAACGAGAAGCATTGGAAAGTGCTAACACGAATACCG
Dm49       CACAATCGAAATGCAGCGCGAGGCTCTGGAGAGCGCCAACACAAACACTG
Lh49       GACGATTGAAATGCAGAGAGAAGTCTTGGAATCACCAATACTAGTTCCA
Tc49       CACCATCGAGATGCAGCGGGAGGCCCTCGAGGGGCAACACCAACACAG
Dba149     AACTATTGAAATGCAGAGGGAAGCCCTCGAAGGAGCTAGCACAAATACTG
Du49       AACTATTGAAATGCAGAGGGAAGCCCTCGAAGGAGCTAGCACAAATACTG
Db49       AACTATTGAAATGCAGAGGGAAGCCCTCGAAGGAGCTAGCACAAATACTG
Dz49       AACTATTGAAATGCAGAGGGAAGCCCTCGAAGGAGCTAGCACAAATACTG
Dv49       AACTATTGAAATGCAGAGGGAAGCCCTCGAAGGAGCTAGCACAAATACTG
a.a.         T   I   E   M   Q   R   E   A   L   E   G   A   S   T   N   T   A
Reynolds   22743221201351240134013134689565
Scan seg.     10        12        14   .
              7%        14%       42%*
                    11        13   .
           19%      5%        33%*
```

FIG. 2

SEQUENCE LISTING

```
<160> NUMBER OF SEQ ID NOS: 167

<210> SEQ ID NO 1
<211> LENGTH: 50
<212> TYPE: DNA
<213> ORGANISM: Diabrotica virgifera

<400> SEQUENCE: 1
gaatacttcc gtgatatggg ttacaacgta tctatgatgg ctgactcgac         50

<210> SEQ ID NO 2
<211> LENGTH: 536
<212> TYPE: DNA
<213> ORGANISM: Diabrotica virgifera

<400> SEQUENCE: 2
agagagactg aagaaatgtt aataaaaaaa caggattttt tagaaaagaa gaagaagatt    60
taccatggta gcaaagaaaa atgcgtcgaa aaataaaaga gttgcactcc aagccctcaa   120
aaagaagaaa cgattggaaa agacccaact acaaatagat ggaaccctta caactattga   180
aatgcagagg gaagccctcg aaggagctag cacaaatact gctgtattag attctatgaa   240
aaatgctgca gatgccctta agaaagctca taagaatttg aatgtagatg atgttcacga   300
tatcatggat gacatagccg aacaacacga catagccaac gaaatcacaa acgctattag   360
caatcctgtc ggattcaccg acgatctgga tgacgatgaa ttagaaaaag aattagaaga   420
gctcgaacaa gaaggattgg aagaagacct gctccaagtc ccaggtccaa ctcaactgcc   480
ggctgtgcct gctgatgcag ttgctactaa accaatcaaa ccagcagcta aaaaag       536

<210> SEQ ID NO 3
<211> LENGTH: 1265
<212> TYPE: DNA
<213> ORGANISM: Drosophila melanogaster

<400> SEQUENCE: 3
aatcggtatc gggtgacgca tacgaacaac agctcccaga caaccaagaa acgcaatagc    60
agaaaaaaac tcacttgttc gctaaattcg ggtgaaaaaa cagatcagcc aggatgagtt   120
tcttcgggaa gatgttcggc ggcaagaagg aagtggcccc caccaccggc gaggcgatac   180
agaagctgcg cgagacggag aacatgctta tcaaaaagca ggagttcctg gaggccaaga   240
tcgaggacga actgaatata gcccgcaaga atgcgtctaa aaacaaaaga gtggccctgc   300
aagcactcaa gaaaaagaag cggctggaga agcaactcca gcagatcgat ggcaccctgt   360
ccacaatcga aatgcagcgc gaggctctgg agagcgccaa cacaaacact gccgtcttga   420
ccacgatgaa gaatgccgcg gatgccctca agagagccca tcagaatatg gacgtggaca   480
aggtgcacga catgatggat gacattgccg agcagcagga cgtggcccgc gagatttccg   540
```

```
atgccatttc gaacccagtg gcattcggcg ccgatctgga tgatgaggat ctcgagcggg    600
aactcgacga gctggagcag gagaactttg ataaggaaat cattggcata cccgagccga    660
cgcccacatt gccagaagca cccacagaag atttgcccga aaggccaaa gaaaagaaaa     720 aggcgacaac cacgactgcc gtggaggatg atgatgatcc agacatgaag cagcttttat    780
cctggtccaa ctaaatcaga gagctattga aatctcctta ctgttctgaa gatacaccct    840 atcgttttg tttaatttaa taatcaatac tgctgttaat taagcaaaat tttagttcga     900
agcgagggag agaatacaag gcattaattc ctttggcaat tcaacaaatg gtacataaac    960
taggaatgtg attttaaaat aaacgaaata agcatagtca ggcctcacat gagcaaaagt    1020
aggtatcaac gtagtttcat atttgatttg tttattttga ataacgctga ttggccatca    1080
ggtgtatgca gatctaatat tccaacaaag aaatgtagct ttttgataaa acccaaata    1140 tgttttgtgg cactcatctt tccgcagtct tagctttgta tcgagcgatt caaacgaaaa    1200
taaaaacatg aagcctctcg actgcaggta actcagtagc cgcgagaggc gcaaaaaaac    1260
atcaa                                                                1265

<210> SEQ ID NO 4
<211> LENGTH: 100
<212> TYPE: DNA
<213> ORGANISM: Diabrotica virgifera

<400> SEQUENCE: 4
aagaagaaac gattggaaaa gacccaacta caaatagatg gaacccttac aactattgaa     60
atgcagaggg aagccctcga aggagctagc acaaatactg                          100

<210> SEQ ID NO 5
<211> LENGTH: 23
<212> TYPE: DNA
<213> ORGANISM: Artificial sequence
<220> FEATURE:
<223> OTHER INFORMATION: Synthetic primer

<400> SEQUENCE: 5
aagaagaaac gattggaaaa gac                                              23

<210> SEQ ID NO 6
<211> LENGTH: 41
<212> TYPE: DNA
<213> ORGANISM: Artificial sequence
<220> FEATURE:
<223> OTHER INFORMATION: Synthetic primer

<400> SEQUENCE: 6
taatacgact cactataggc agtatttgtg ctagctcctt c                          41

<210> SEQ ID NO 7
<211> LENGTH: 22
<212> TYPE: DNA
<213> ORGANISM: Artificial sequence
<220> FEATURE:
<223> OTHER INFORMATION: Synthetic primer

<400> SEQUENCE: 7
cagtatttgt gctagctcct tc                                               22

<210> SEQ ID NO 8
<211> LENGTH: 42
<212> TYPE: DNA
```

<213> ORGANISM: Artificial sequence
<220> FEATURE:
<223> OTHER INFORMATION: Synthetic primer

<400> SEQUENCE: 8
taatacgact cactatagga agaagaaacg attggaaaag ac            42

<210> SEQ ID NO 9
<211> LENGTH: 26
<212> TYPE: DNA
<213> ORGANISM: Artificial sequence
<220> FEATURE:
<223> OTHER INFORMATION: Synthetic primer

<400> SEQUENCE: 9
aagaagaaac gattggaaaa gaccca                              26

<210> SEQ ID NO 10
<211> LENGTH: 26
<212> TYPE: DNA
<213> ORGANISM: Artificial sequence
<220> FEATURE:
<223> OTHER INFORMATION: Synthetic primer

<400> SEQUENCE: 10
tgggtctttt ccaatcgttt cttctt                              26

<210> SEQ ID NO 11
<211> LENGTH: 32
<212> TYPE: DNA
<213> ORGANISM: Artificial sequence
<220> FEATURE:
<223> OTHER INFORMATION: Synthetic primer

<400> SEQUENCE: 11
aattcaaggg tgttttcatg aactagacca ta                       32

<210> SEQ ID NO 12
<211> LENGTH: 32
<212> TYPE: DNA
<213> ORGANISM: Artificial sequence
<220> FEATURE:
<223> OTHER INFORMATION: Synthetic primer

<400> SEQUENCE: 12
ctagtctagt tcatgaaaac acccttgtca ag                       32

<210> SEQ ID NO 13
<211> LENGTH: 32
<212> TYPE: DNA
<213> ORGANISM: Artificial sequence
<220> FEATURE:
<223> OTHER INFORMATION: Synthetic primer

<400> SEQUENCE: 13
aattcttgac aagggtgttt tcatgaacta ga                       32

<210> SEQ ID NO 14
<211> LENGTH: 32
<212> TYPE: DNA
<213> ORGANISM: Artificial sequence
<220> FEATURE:
<223> OTHER INFORMATION: Synthetic primer

<400> SEQUENCE: 14
ctagttcatg aaaacaccct tgtcaaacac ag                       32

<210> SEQ ID NO 15
<211> LENGTH: 32
<212> TYPE: DNA
<213> ORGANISM: Artificial sequence
<220> FEATURE:
<223> OTHER INFORMATION: Synthetic primer

<400> SEQUENCE: 15
aattctgtgt tgacaagggg tgttttcatg aa                32

<210> SEQ ID NO 16
<211> LENGTH: 32
<212> TYPE: DNA
<213> ORGANISM: Artificial sequence
<220> FEATURE:
<223> OTHER INFORMATION: Synthetic primer

<400> SEQUENCE: 16
ctagtaaaac acccttgtca aacacaaaat gg                32

<210> SEQ ID NO 17
<211> LENGTH: 32
<212> TYPE: DNA
<213> ORGANISM: Artificial sequence
<220> FEATURE:
<223> OTHER INFORMATION: Synthetic primer

<400> SEQUENCE: 17
aattccattt tgtgtttgac aagggtgttt ta                32

<210> SEQ ID NO 18
<211> LENGTH: 746
<212> TYPE: DNA
<213> ORGANISM: Artificial sequence
<220> FEATURE:
<223> OTHER INFORMATION: Synthetic primer

<400> SEQUENCE: 18
gcatcctgat ttatatcggg caaaagatta aatatgtctt gtaattggta gatgatttgg      60
tgattgattg gaagctggtt accacacact tgtaccaaat agtccctaat atcacgtaac     120
tgtgaatgga gacctttaa ccctaaaagc tgattcgtta ttctctgtga caaagtacca     180
acagttgtgt ctttaatatc tctcaataag tgttcaacac caacttcttc agcttcctca     240
gctccgattt cactaggaac atgctcaaat gttttagatg taggtgaacc gtcatcgtgt     300
acttcttcta cagcttgata agcttcagtt ggtaaaccta atctttttgg tttagcgtct     360
atgataacta gaacggaatt tggacaatac cttctgatta actcattaat ggcaatatca     420
tttttgatgaa gtttggggcc ggtgtggtac caacctacta ctcgttccct ggcattaact     480
tttttgaaca ttccatacat gttttctaag taatcatggt ccaagaacca cacagactta     540
tccttgtcat cttcgtcaaa aggaactgca aaactgttag aaacatctaa gactcccttta    600
gcacgccaac agccaagaag aacaccaaca acacgctttt gattgccgat tttgcccatg     660
cgattaaaat ggtccaccac acttagaaga accaaagggt ggactattac tttattagtt     720
gttaattctt gactcggcat tttcgg                                          746

<210> SEQ ID NO 19
<211> LENGTH: 746
<212> TYPE: DNA
<213> ORGANISM: Artificial sequence
<220> FEATURE:

<223> OTHER INFORMATION: Synthetic primer

<400> SEQUENCE: 19

```
gcatcctgat ttatatcggg caaaagatta aatatatctt gtaattgata gatgatttgg      60
tgattaattg gaagttggtt agcacaaact tgtactaaat agtccctaat atcacgtaac     120
tgtgaatgga gaccttttaa tcctaaaagc tgatttgtta ttctctgaga caaagtgcca     180
acagttgtat ctttaatatc tctcaataag tgttcaacac caacttcttc tgcctcttca     240
gctccaattt cactaggaac atgctcaaat gttttagaag taggtgaacc atcatcatgt     300
acttcttcta cagcttgata agcctcagtc ggtaaaccta atctttttgg tttagcatct     360
ataataacta gaactgaatt tggacaatat cttctgatta actcattaat ggcaatatca     420
ttttgatgca gtttggggcc agtatggtac caacccacta ctcgttccct agcattaact     480
tttttaaaca ttccatacat attttctaaa taatcatggt ccaagaacca aacagattta     540
tctttgtcat cttcatcaaa gggaactgca aaactgttag aaacatctaa aactccttta     600
gcacgccaac aaccaagaag aacaccaaca acacgctttt gattgccgat tttgcccatc     660
cgattaaaat ggtctactac acttagaagg accaaaggat ggactattac tttattagtt     720
gttaattctt gactcggcat tttcgg                                          746
```

<210> SEQ ID NO 20
<211> LENGTH: 746
<212> TYPE: DNA
<213> ORGANISM: Artificial sequence
<220> FEATURE:
<223> OTHER INFORMATION: Synthetic primer

<400> SEQUENCE: 20

```
gcatcctgat ttatatcggg caaaagatta aatatgtctt gtaattggta gatgatttgg      60
tgattgattg gaagctggtt accacacact tgtaccaaat agtccctaat atcacgtaac     120
tgtgaatgga gaccttttaa ccctaaaagc tgattcgtta ttctctgtga caaagtacca     180
acagttgtgt ctttaatatc tctcaataag tgttcaacac caacttcttc agcttcctca     240
gctccgattt cactaggaac atgctcaaat gttttagatg taggtgaacc gtcatcgtgt     300
acttcttcta cagcttgata agcttcagtt ggtaaaccta atctttttgg tttagcgtct     360
atgataacta gaacggaatt tggacaatac cttctgatta actcattaat ggcaatatca     420
ttttgatgaa gtttggggcc ggtgtggtac caacctacta ctcgttccct ggcattaact     480
tttttgaaca ttccatacat gttttctaag taatcatggt ccaagaacca cacagactta     540
tccttgtcat cttcgtcaaa aggaactgca aaactgttag aaacatctaa gactccttta     600
gcacgccaac agccaagaag aacaccaaca acacgctttt gattgccgat tttgcccatg     660
cgattaaaat ggtccaccac acttagaaga accaaagggt ggactattac tttattagtt     720
gttaattctt gactcggcat tttcgg                                          746
```

<210> SEQ ID NO 21
<211> LENGTH: 26
<212> TYPE: DNA
<213> ORGANISM: Artificial sequence
<220> FEATURE:
<223> OTHER INFORMATION: Synthetic primer

<400> SEQUENCE: 21

```
gaaacgattg gaaagaccc aactac                                            26
```

```
<210> SEQ ID NO 22
<211> LENGTH: 512
<212> TYPE: DNA
<213> ORGANISM: Artificial sequence
<220> FEATURE:
<223> OTHER INFORMATION: Synthetic primer

<400> SEQUENCE: 22
gtcgagaaca ttttgaaatt tttrgataag tactacgttc ccagcaaaat agctaaagga     60
aatggccaaa taaaaacatg ctctcatcac gactatccta ctagtggaga agtatgcgaa    120
gtcgatgtca gagattggga agaatgcaac agggatcaat tctttaatta tcacaagaat    180
tctccatgta tttttattaa attgaacaaa atatatgact gggagccaga atattacgat    240
gatccctaca atttacctga ggaaatgccg gataatctga agcaacatat aagaagtatc    300
aacaatacta gagagttgag aaacgtttgg gtctcatgtc agggagaaaa tcctgctgat    360
gtagaatact tgggtcccat tacatactat cccagaggca tacagggctt ccctggttac    420
tattttccgt acttgaactc tgaaggttac ctaagtcctt tagtagcagt taaatttgaa    480
agaccagtgg ctggtatcgt tattaacgta ga                                  512

<210> SEQ ID NO 23
<211> LENGTH: 513
<212> TYPE: DNA
<213> ORGANISM: Artificial sequence
<220> FEATURE:
<223> OTHER INFORMATION: Synthetic primer

<400> SEQUENCE: 23
gtagagaaca ttttgaaatt tttggataag tactacgttc ccagcaaaat agctaaagga     60
aatggtcaaa taaaaacatg ctctcatcac gactatccta ccagtggaga agtatgcgaa    120
gttgatgtta gagattggga ggaatgcaat agggatcagt tctttaatta tcacaagaat    180
tctccatgta tttttattaa attgaacaaa atatatgact gggaaccatt atattacgac    240
gatccctata atttacccga ggaaatgcct gattctctga agcaacatat aagaagtatc    300
aacaatacta gagagttgag aaacgtttgg atctcgtgtc agggagaaaa tcctgctgat    360
gtagaatact tgggccccat tacatactat cctagaggca tacagggctt tccaggctac    420
tattttccgt acttgaactc tgaaggttac ctaagtcctt tagtagcagt taaatttgaa    480
agaccagtcg ctggtatcgt ctattaacgt aga                                 513

<210> SEQ ID NO 24
<211> LENGTH: 512
<212> TYPE: DNA
<213> ORGANISM: Artificial sequence
<220> FEATURE:
<223> OTHER INFORMATION: Synthetic primer

<400> SEQUENCE: 24
gtagagaaca ttttgaaatt tttggataag tactatgttc ccagcaaaat agctaaagga     60
aatagccaaa taaaaacatg ctctcatcac gactatccta ccagtggaga agtatgcgaa    120
gttgatgtta gagattggga agaatgcaat agggatcagt tctttaatta tcacaagaat    180
tctccatgta tctttattaa attgaacaaa atatatgact gggaaccaat gtattacgat    240
gatccctatg atttacccga ggaaatgcct gatactctga agcaacatat aaggagtatc    300
aacaatacta gagagttgag aaatgtttgg atctcgtgtc agggagaaaa tcctgctgat    360
gtagaatact tgggccccat tacatactat cctagaggca tacagggctt cccaggctac    420
```
tattttccgt acttgaactc tgaaggttac ctaagccctt tagtagcagt taaatttgaa    480
agaccagtcg ctggcatcgt cattaacgta ga    512

<210> SEQ ID NO 25
<211> LENGTH: 543
<212> TYPE: DNA
<213> ORGANISM: Artificial sequence
<220> FEATURE:
<223> OTHER INFORMATION: Synthetic primer

<400> SEQUENCE: 25
gggctccaac aagacgagct attcttactg ggtcgagaac attttaaaat ttttggataa    60
gtactacgtt cccagcaaaa tagctaaagg aaatggccaa atwaaaacat gctctcatca    120
cgactatcct actagtggag aagtatgcga agtcgatgtc agagattggg aagaatgcaa    180
cagggatcaa ttctttaatt atcacaagaa ttctccatgt atttttatta aattgaacaa    240
aatatataac tgggagccaa trtattacga tgatccmtac gatttacctg aggaaatgcc    300
ggataatctg aagcaacata aaggggtat caacaatact agagagttga gaaacgtttg    360
ggtytcatgt carggagaaa atcctgctga tgtagaatac ttgggcccca ttacatacta    420
tccccgaasc rtacarggct tccctggtta ctattttccg tacttgaact ctgaaggtta    480
cctaagtcct ttagtagcag ttaaatttga agaccagtg gctggtatcg ttattaacgt    540
aga    543

<210> SEQ ID NO 26
<211> LENGTH: 512
<212> TYPE: DNA
<213> ORGANISM: Artificial sequence
<220> FEATURE:
<223> OTHER INFORMATION: Synthetic primer

<400> SEQUENCE: 26
gtcgagaaca ttttaaaatt tttggataag tactacgttc ccagcaaaat agctaaagga    60
aatggccaaa taaaaacatg ctctcatcac gactatccta ctagtggaga agtatgcgaa    120
gtcgatgtca gagattggga agaatgcaac agggatcaat tctttaatta tcacaagaat    180
tctccatgta tttttattaa attgaacaaa atatataact gggagccaat atattacgat    240
gatccctacg atttacctga ggaaatgccg gataatctga agcaacatat aaggggtatc    300
aacaatacta gagagttgag aaacgtttgg gtttcatgtc agggagaaaa tcctgctgat    360
gtagaatact tgggcccat tacatactat ccccgaacca taaaggctt ccctggttac    420 tattttccgt acttgaactc tgaaggttac ctaagtcctt tagtagcagt taaatttgaa    480
agaccagtgg ctggtatcgt tattaacgta ga    512

<210> SEQ ID NO 27
<211> LENGTH: 501
<212> TYPE: DNA
<213> ORGANISM: Artificial sequence
<220> FEATURE:
<223> OTHER INFORMATION: Synthetic primer

<400> SEQUENCE: 27
taaaaagaaa gtatggttgg accctaatga aatcaacgaa attgctaaca ccaactcaag    60
acagaacatc cgtaagttga tcaaggatgg tcttattatt aagaagcccg tagctgtaca    120
ttcccgtgcc cgtgttcgca aaaacactga agcccgcagg aaaggaaggc actgcgtttt    180
cggtaaaagg aagggtactg ctaatgcccg taccccacaa aaggaattat ggattcagcg    240

```
catgagagtt ttgcgtcgtc tccttaaaaa atacagggaa gctaaaaaaa ttgacagaca    300
tctataccac tcactctaca tgaaggccaa gggtaacgta ttcaagaaca agcgtgtcct    360
tatggaatac atccacaaga agaaggcaga gaaagcccgt gccaagatgt tggcagacca    420
ggccaatgcc agaaggatga aggtaaaaca ggctagagaa agrcgtgagg aacgtatcgc    480
cacaaagaaa caagaagttt t                                              501
```

<210> SEQ ID NO 28
<211> LENGTH: 462
<212> TYPE: DNA
<213> ORGANISM: Artificial sequence
<220> FEATURE:
<223> OTHER INFORMATION: Synthetic primer

<400> SEQUENCE: 28

```
taaaaagaaa gtttggttgg accctaatga aatcaacgaa atcgcmaaca ccaactcaag    60
acagaacatt cgtaarttga tcaaggatgg tcttattatt aagaagcccg tagctgtaca    120
ttcccgtgcc cgtgttcgca aaaacactga agcccgcagg aaaggaaggc actgtggttt    180
tggtaaaagg aagggtactg ctaatgcccg taccccrcaa aaggaattat ggattcaacg    240
catgagagtc ttgcgtcggc tccttaaaaa atatagggaa gctaaaaaaa ttgacagaca    300
tctataccac tcactgtaca tgaaggctaa gggtaatgta ttcaagaaca agcgtgtcct    360
catggaatac atccacaaga agaaggcaga gaaagcccgt gccaagatgt tggcagacya    420
ggccaatgcc agaaggatga aggtaaaaca ggctagggaa ag                       462
```

<210> SEQ ID NO 29
<211> LENGTH: 501
<212> TYPE: DNA
<213> ORGANISM: Artificial sequence
<220> FEATURE:
<223> OTHER INFORMATION: Synthetic primer

<400> SEQUENCE: 29

```
taaaaagaaa gtatggttgg accctaatga aatcaacgaa attgccaaca ctaactcaag    60
acagaacatc cgtaagttga taaggatgg tcttattatt aagaagcccg tagctgtaca    120
ttcccgtgcc cgtgttcgca aaaacactga agcccgcagg aaaggaaggc actgcggttt    180
tggtaaaagg aagggtactg ctaatgcccg taccccacaa aaggaattat ggattcaacg    240
catgagagtt ttgcgtcgtc tccttaaaaa atacagggaa gctaaaaara ttgacagaca    300
tctataccac tcactctaca tgaaggccaa gggtaacgta ttcaagaaca agcgtgtcct    360
tatggaatac atccacaaga agaaggcaga gaaagcccgt gccaagatgt tggcagacca    420
ggccaatgcc agaaggatga aggtaaaaca ggctagagaa agacgtgagg aacgtatcgc    480
cacaaagaaa caagaagttt t                                              501
```

<210> SEQ ID NO 30
<211> LENGTH: 501
<212> TYPE: DNA
<213> ORGANISM: Artificial sequence
<220> FEATURE:
<223> OTHER INFORMATION: Synthetic primer

<400> SEQUENCE: 30

```
taaaaagaaa gtatggttgg accctaatga aatcaacgaa attgccaaca ctaactcaag    60
acagaacatc cgtaagttga taaggatgg tcttattatt aagaagcccg tagctgtaca    120
```

```
ttcccgtgcc cgtgttcgca aaaacactga agcccgcagg aaaggaaggc actgcggttt      180
tggtaaaagg aagggtactg ctaatgcccg tacccacaa aaggaattat ggattcaacg       240
catgagagtt ttgcgtcgtc tccttaaaaa atacagggaa gctaaaaaaa ttgacagaca     300
tctataccac tcactctaca tgaaggccaa gggtaacgta ttcaagaaca agcgtgtcct     360
tatggaatac atccacaaga agaaggcaga gaaagcccgt gccaagatgt tggcagacca    420
ggccaatgcc agaaggatga aggtaaaaca ggctagagaa agacgtgagg aacgtatcgc     480
cacaaagaaa caagaagttt t                                                501
```

```
<210> SEQ ID NO 31
<211> LENGTH: 435
<212> TYPE: DNA
<213> ORGANISM: Artificial sequence
<220> FEATURE:
<223> OTHER INFORMATION: Synthetic primer

<400> SEQUENCE: 31
gtctaggcac ggacaaaagg gaacgtgcgg tatacaatac cgtcaagagg atatgatttt     60
tagtgctgaa ggtattactc cagacattat catcaatcct cacgctatcc cctcccgtat    120
gacgattggt cacttgatcg agtgcatcca aggtaaggta tcatccaata aaggagwaat   180
cggtgatgct acacctttca acgatgccgt caacgtacag aaaatctcca ctttgttaca   240
agaatatggt tatcaactca gaggcaacga agtaatgtac aacggccaca ctggacgtaa  300
gataaatgct cagattttct taggacctac ttactatcaa agattgaagc acatggtgga  360
cgataagatc cattcaagag ctagaggacc attgcagatt ctcgtcagac agcctatgga   420
gggtcgtgca agaga                                                      435
```

```
<210> SEQ ID NO 32
<211> LENGTH: 26
<212> TYPE: DNA
<213> ORGANISM: Artificial sequence
<220> FEATURE:
<223> OTHER INFORMATION: Synthetic primer

<400> SEQUENCE: 32
gtagttgggt cttttccaat cgtttc                                           26
```

```
<210> SEQ ID NO 33
<211> LENGTH: 435
<212> TYPE: DNA
<213> ORGANISM: Artificial sequence
<220> FEATURE:
<223> OTHER INFORMATION: Synthetic primer

<400> SEQUENCE: 33
gtctaggcac ggacaaaagg gaacgtgcgg tatacaatac cgtcaagagg atatgatttt     60
tagtgctgaa ggtattacgc cagacattat cattaatcct cacgctatcc cctcccgtat   120
gacgattggt cacttgatcg agtgcatcca aggtaaggta tcatccaata aaggagaaat   180
cggtgatgct acacctttca acgatgccgt caacgtacag aaaatctcca ctttgttaca   240
agaatatggt tatcaactca gaggcaacga agtaatgtac aacggccata ctggacgtaa  300
gataaatgct cagattttct taggacctac ctattatcaa agattgaagc acatggtgga  360
cgataagatt cattcaagag ctagaggacc gttgcagatt ctcgtcagac agcctatgga   420
gggtcgtgca agaga                                                      435
```

```
<210> SEQ ID NO 34
<211> LENGTH: 435
<212> TYPE: DNA
<213> ORGANISM: Artificial sequence
<220> FEATURE:
<223> OTHER INFORMATION: Synthetic primer

<400> SEQUENCE: 34
gtctaggcac ggacaaaagg gaacgtgcgg tatacaatac cgtcaagagg atatgatttt      60
tagtgctgaa ggtattackc cagacattay catyaatcct cacgctatcc cctcccgtat     120
gacgattggt cacttgatcg agtgcatcca aggtaaggta tcatccaata aaggagaaat     180
cggtgatgct acacctttca acgatgccgt caacgtacag aaaatctcca ctttgttaca     240
agaatatggt tatcaactca gaggcaacga agtaatgtac aacggccaya ctggacgtaa     300
gataaatgct cagattttct taggacctac ytaytatcaa agattgaagc acatggtgga     360
cgataagaty cattcaagag ctagaggacc gttgcagatt ctcgtcagac agcctatgga     420
gggtcgtgca agaga                                                     435

<210> SEQ ID NO 35
<211> LENGTH: 490
<212> TYPE: DNA
<213> ORGANISM: Artificial sequence
<220> FEATURE:
<223> OTHER INFORMATION: Synthetic primer

<400> SEQUENCE: 35
gtttagatca agaattgaaa atcatcggag cctttggtct cagaaacaaa cgtgaagtat      60
ggagggtaaa atacactcta gccaaaatcc gtaaggccgc cagagaactg cttactctag     120
aagagaaaga acccaaaagg ttgtttgaag gtaatgcact cctacgtcgt ttggtccgta     180
ttggagtact agacgagaac agaatgaagc ttgattacgt attgggtctc aagattgaag     240
atttcttgga aagacgtctg cagacacaag tcttcaaatc tggtctagct aagtcaatcc     300
atcatgctag ggtattgatc agacaacgcc acattcgggt ccgcaaacaa gttgtgaaca     360
ttccctcctt catcgtccgt ttggattcac aaaaacacat cgacttctct ctgaaatcac     420 cttttgggagg cggtcgtcca ggacgtgtta agaggaagaa cctcaccaag aagagcggtg     480
gtggaggtgc                                                           490

<210> SEQ ID NO 36
<211> LENGTH: 490
<212> TYPE: DNA
<213> ORGANISM: Artificial sequence
<220> FEATURE:
<223> OTHER INFORMATION: Synthetic primer

<400> SEQUENCE: 36
gtttagatca agaattgaaa atcatcggag ccttcggtct tcgtaacaaa cgtgaagtat      60
ggagagtgaa atacactctg gccaaaatcc gtaaggccgc cagagaactg cttactctag     120
aagagaagga tcccaaaagg ttgtttgaag gtaatgcact cctacgtcga ttggtccgta     180
tcggagtact agacgagaac agaatgaagc tcgattatgt attgggtctc aagattgaag     240
atttcttgga aagacgtcta cagacacaag tcttcaaatc tggtctagct aagtcaatcc     300
atcatgctag ggtattgatc agacaacgtc acatccgggt ccgcaagcaa gttgtgaaca     360
ttccctcctt cattgtccgt ttagattcac aaaaacacat tgacttctct ctgaaatcac     420 cttttgggagg tggtcgtcca ggacgtgtta agaggaagaa cctcaccaag aagagcggtg     480
```
gtggaggtgc 490

<210> SEQ ID NO 37
<211> LENGTH: 490
<212> TYPE: DNA
<213> ORGANISM: Artificial sequence
<220> FEATURE:
<223> OTHER INFORMATION: Synthetic primer

<400> SEQUENCE: 37
gtctagatca agaattgata atcatgggag ccttcggtct tcgtaacaaa cgtgaagtat    60
cgagagtgaa atacactctg gccaaaatct gtaaggccgc cagagaactg cttactctag   120
aagagaagga tcccaaaagg ttgtttgaag gtaatgcact cgtacgtcga ttggtccgta   180
tcggactact agacgagaac agaatgaagc tggattatgt attgggtttc aagattgaag   240
atttcttgga aagacgttta cagacacaag tcttcaaatc tggtctagtt aagtcaatcc   300
atcattctag ggtattgatc agacaacgtc acatccgggt ccgcaagcaa gtggtgaaca   360
ttccctcctt cattgtccgt ttagattcac aaaaccacat tgacttctct ctgaaatcac   420
ctctgggagg tggtcgtcca ggacgtgtta agaggaagaa cctcaccaag aagagcggtg   480
gtggaggtgc                                                          490

<210> SEQ ID NO 38
<211> LENGTH: 490
<212> TYPE: DNA
<213> ORGANISM: Artificial sequence
<220> FEATURE:
<223> OTHER INFORMATION: Synthetic primer

<400> SEQUENCE: 38
gtttagatca agaattgaaa atcatcggag cctttggtct ccgaaacaaa cgtgaagtat    60
ggagagtaaa atacactcta gccaaaatcc gtaaggccgc cagagaactg cttactctag   120
aagagaaaga acccaaaagg ttgtttgaag gtaatgcact cctacgtcgt ttggttcgta   180
ttggagtact agacgagaac agaatgaagc tcgattacgt attgggtctc aagattgaag   240
atttcttgga aagacgtctg caaacacaag tcttcaaatc tggtctagct aagtcaatcc   300
atcatgctag ggtattgatc agacaacgac acattcgggt ccgcaaacaa gttgtgaaca   360
ttccctcctt catcgtccgt ttggattcac aaaaacacat cgacttctct ctgaaatcac   420
ctttgggagg cggtcgtcca ggacgtgtta agaggaagaa cctcaccaag aagagcggtg   480
gtggaggtgc                                                          490

<210> SEQ ID NO 39
<211> LENGTH: 598
<212> TYPE: DNA
<213> ORGANISM: Artificial sequence
<220> FEATURE:
<223> OTHER INFORMATION: Synthetic primer

<400> SEQUENCE: 39
atcggagatg aagaraagga agggcagtat ggttatgtcc atgctgtctc aggtccagty    60
gttactgctg agaaaatgtc tggttctgct atgtacgaac tggtacgtgt cggatactat   120
gagctggtag gagaaatcat tagattggaa ggtgacatgg ctactattca ggtmtacgaa   180
gaaacatcag gtgtaactgt tggtgatcca gtattaagaa ctggtaaacc actttcagta   240
gaacttggac ctggtattat gggttccatt tttgatggta tccaacgtcc attgaaagac   300
atttgtgacg ctactgatag tatttacatc cccaagggta ttaacgtacc ttctttatcg   360

```
agaacagcaa aatgggactt caacccaatm aacatcaagt tgggatctca cttaactgga      420
ggtgatatat atggtctagt tcatgaaaac acccttgtca aacayaaaat gwtwctgcct      480
ccyagagcta agggtactgt aacctacatt gcagaaccag gaaactacac tgttgatgaa      540
gtagtattgg aaactgaatt tgatggtgat cgtaccaaat atactatgtt gcaagtat       598
```

<210> SEQ ID NO 40
<211> LENGTH: 598
<212> TYPE: DNA
<213> ORGANISM: Artificial sequence
<220> FEATURE:
<223> OTHER INFORMATION: Synthetic primer

<400> SEQUENCE: 40

```
atcggagatg aagagaagga agggcagtat ggttacgtcc atgctgtctc aggtccagtc       60
gttactgctg agaaaatgtc tggttctgct atgtacgaac tggtgcgtgt aggatactat      120
gagctggtag gagaaatcat tagattggaa ggtgacatgg ctactattca ggtatatgaa      180
gaaacttctg gtgtaaccgt tggtgatcca gtattaagaa ctggtaaacc actttcagta      240
gaacttggac ctggtattat gggttccatt tttgatggta ccaacgtcc attgaaagac       300 atttgcgatg ctactgaaag tatttacatc cctaagggta tcaatgtacc ttctttatcg      360
agaactgcaa aatgggactt caacccaatc aacatcaagt tgggatctca cttaactgga      420
ggtgatatat atggtctagt tcatgaaaac actcttgtca aacacaaaat gatactgcct      480
cccaaagcta agggtactgt aacctacatt gcagaaccag gaaactacac agttgatgaa      540
atagtattgg aaacagaatt tgatggtgat cgtaccaaat atactatgtt gcaagtat       598
```

<210> SEQ ID NO 41
<211> LENGTH: 598
<212> TYPE: DNA
<213> ORGANISM: Artificial sequence
<220> FEATURE:
<223> OTHER INFORMATION: Synthetic primer

<400> SEQUENCE: 41

```
atcggagatg aagagaagga agggcagtat ggttatgtcc atgctgtctc aggtccagtc       60
gttactgctg agaaaatgtc tggttctgct atgtacgaac tggtacgtgt cggatactat      120
gagctggtag gagaaatcat tagattggaa ggtgacatgg ctactattca ggtatacgaa      180
gaaacatcag gtgtaactgt tggtgatcca gtattaagaa ctggtaaacc actttcagta      240
gaacttggac ctggtattat gggttccatt tttgatggta ccaacgtcc attgaaagac       300 atttgtgacg ctactgatag tatttacatc cccaagggta ttaaygtacc ttctttatck      360
agaacagcaa aatgggactt caacccaatc aacatcaagt tgggatctca cttaactgga      420
ggtgatatat atggtctagt tcatgaaaac acccttgtca aacacaaaat gattctgcct      480
cctagagcta agggtactgt aacctacatt gcagaaccag gaaactacac tgttgatgaa      540
gtagtattgg aaactgaatt tgatggtgat cgtaccaaat atactatgtt gcaagtat       598
```

<210> SEQ ID NO 42
<211> LENGTH: 1585
<212> TYPE: DNA
<213> ORGANISM: Artificial sequence
<220> FEATURE:
<223> OTHER INFORMATION: Synthetic primer

<400> SEQUENCE: 42

```
cggagctttc ggttgtggaa aaactgtaat ttcacaatct ctttccaaat attccaactc      60
tgatgtcatt atctacgtcg gttgcggaga aagaggtaac gaaatgtctg aagtattgag     120
agatttccct gaattgactg ttgaaattga cggacacact gaatctatta tgaaacgtac     180
cgcattggtc gccaacacat ctaacatgcc tgtagctgct cgtgaagctt ctatctacac     240
tggtattact ctgtctgaat acttccgtga tatgggttac aacgtatcta tgatggctga     300
ctcgacatca cgttgggccg aagctttgag agaaatttca ggtcgtttgg ctgaaatgcc     360
tgccgattcc ggttatccgg cttacttggg tgcccgtttg gcttccttct acgaacgtgc     420
tggccgtgtt aaatgtctag gtaatccaga cagagaagga tccgtttcaa ttgtaggagc     480
cgtatcacct cctggtggtg atttctcaga tcctgttacc actgctactc ttggtattgt     540
acaggtgttc tggggtttgg acaagaaact tgcccaacgt aagcacttcc cttcagtaga     600
ctggcttgga tcatattcca aatatttaag agcattggac gacttttatg acaaaaactt     660
ccaagagttt attcctctta gaaccaaagt taaggaaatt cttcaggaag aagatgatct     720
agccgaaatt gtgcagctgg taggtaaagc atctctggca gaaacggaca aaatcacctt     780
ggaaattgcc aggcttctta agaagatttc ttgcaacaa aactcatact cttcttatga     840
cagattctgt ccattctata aaactgtcgg tatgttgaga aacatgatcg gtttgtacga     900
catggcgaga cacgccgtag aatcaaccgc acaatcagaa ataagatca cttggaacgt     960 aataagagat tcaatgagtg gaattttata tcaacttagc agtatgaaat ttaaggatcc    1020
cgtaaaagat ggtgaagcta aaatcaaggc agattttgat caattatatg aagatattca    1080
acaggccttc agaaacttag aagattaaat cttttaagg aaattttcct atttttgttca    1140 tcagtgtaag tttaaaaata tagcgatatt tatcaaaaag aataataagg cctctatccc    1200
tcacttctgt gaatattaat atggccgtac taaagatagt aactaaagat aggttttctc    1260 tttttttgata ttatcctgta caaaataaat tatgtaaatt gttgaatatg tgtatagttt    1320
ttttgggtga gggtacagtg cttattaaat acttttaaa catttttccc gccattccaa    1380
ttactattaa gttttttcgt tttaatactt tttttaaatat gcaggtgctt aatatcgttt    1440
atattttcag tattacttgg ttttcttcat gtaaattgtt ttaaattttt cttttaccct    1500
tttaatcttg tatattacat tacccaataa agttaattgt acagattaag ataaacgagt    1560
atcttataac atctattaga ttgtt                                          1585
```

<210> SEQ ID NO 43
<211> LENGTH: 26
<212> TYPE: DNA
<213> ORGANISM: Artificial sequence
<220> FEATURE:
<223> OTHER INFORMATION: Synthetic primer

<400> SEQUENCE: 43

```
gattggaaaa gacccaacta caaata                                           26
```

<210> SEQ ID NO 44
<211> LENGTH: 1585
<212> TYPE: DNA
<213> ORGANISM: Artificial sequence
<220> FEATURE:
<223> OTHER INFORMATION: Synthetic primer

<400> SEQUENCE: 44

```
cggtgctttc ggttgtggaa aaactgtaat ttcacaatct ctttccaaat attccaactc      60
tgatgtcatt atctacgtcg gttgcggaga aagaggtaac gaaatgtctg aagtattgag     120
```

```
agatttccct gaattgactg ttgaaataga cgggcacact gaatctatta tgaaacgtac    180
tgcattrgtt gccaacacct ctaacatgcc tgtagctgct cgtgaagctt ctatctatac    240
tggtattact ctttctgaat acttccgtga tatgggttac aatgtatcta tgatggctga    300
ctcgacatca cgttgggccg aagctttgag agaaatttca ggtcgtttgg ctgaaatgcc    360
tgccgattcc ggttayccgg cttacttggg tgcccgtttg gcttccttct acgaacgtgc    420
aggtcgtgtt aaatgtctag gtaatccaga cagggaagga tccgtttcaa ttgtaggagc    480
tgtatcacct cctggtggtg atttctcaga tcctgttacc accgctaccc ttggtattgt    540
acaggtgttc tggggtttgg acaagaaact tgctcaacgt aagcacttcc cttcagtaga    600
ctggcttgga tcatactcca aatatttacg agcattggat gacttttatg ataaaaacta    660
ccaagagttt attcctctta gaaccaaagt taaggaaatt cttcaggaag aagatgatct    720
agccgaaatt gtgcagctgg taggtaaagc atctctagca gaaacggaca aaatcacctt    780
ggaaattgcc aggcttctta agaagatttc ttgcaacaa aactcatact cttcttacga    840
cagattctgt ccattctata aaactgttgg tatgctcagg aacatgatcg gtttgtacga    900
tatggcgaga cacgccgtag aatcaaccgc acaatcagaa ataagatca cttggaacgt    960 aataagagat tcaatgagtg gaattttata tcaacttagc agtatgaaat ttaaggatcc   1020
cgtaaaagat ggtgaagcta agatcaaggc agattttgat caattatatg aagatattca   1080
acaggccttc agaaacttag aagattaaat cattttaagg aaattttcct attttgttca   1140
tcagtgtaag tttaaaaata tagcgatatt tatcaaaaag aataataagg cctctatccc   1200
tcacttctgt gaatattaaa atggccgtac taaagatagt aactaaagat aagttttctc   1260 tttttgata ttatcctgta caaaataaat tatgtaaatt gttgaatatg tgtatagttt    1320
ttttgggtga gggtacagtg cttattaaat acttttaaa cagttttccc gccattccaa    1380
ttactattag gttttttcgt tttaatactt tttaaatat acaggtgctt aatatcgttt    1440
atattttcag tattacttgg ttttcttcat gtaaattgtt ttaaattttc cttttacct    1500 tttaatcttg tatattacat tacccaatat agttaattgt acagattaag ataaacaaat   1560
atcttattac atctattaga ttgtt                                         1585
```

<210> SEQ ID NO 45
<211> LENGTH: 1586
<212> TYPE: DNA
<213> ORGANISM: Artificial sequence
<220> FEATURE:
<223> OTHER INFORMATION: Synthetic primer

<400> SEQUENCE: 45

```
cggagctttc ggttgtggaa aaactgtaat ttcacaatct ctttccaaat attccaactc     60
tgatgtcatt atctacgtcg gttgcggaga agaggtaac gaaatgtctg aagtattgag    120
agatttccct gaattgactg ttgaaattga cgggcacact gaatctatta tgaaacgtac    180
cgcattggtc gccaacacat ctaacatgcc tgtagctgct cgtgaagctt ctatctayac    240
tggtattact ctttctgaat acttccgtga tatgggttac aacgtatcta tgatggctga    300
ctcgacatca cgttgggccg aagctttgag agaaatttca ggtcgtttgg ctgaaatgcc    360
tgccgattcc ggttatccgg cttacttrgg tgcccgtttg gcttccttct acgaacgtgc    420
tggycgcgtt aaatgtytag gtaatccaga cagagaagga tccgtttcaa ttgtaggagc    480
cgtatcacct cctggtggtg atttctcaga tcctgttacc actgctactc ttggtattgt    540
```

```
acaggtgttc tggggtttgg acaagaaact tgcccaacgt aagcacttcc cttcagtaga       600
ctggcttgga tcatattcca aatatttaag agcattggac gacttttatg acaaaaactt       660
ccaagagttt attcctctta gaaccaaagt taaggaaatt cttcaggaag aagatgatct       720
agccgaaatt gtgcagctgg taggtaaagc atctctggca gaaacggaca aaatcacctt       780
ggaaattgcc aggcttctta agaagatttt cttgcaacaa aactcatact cttcttatga       840
cagattctgt ccattctata aaactgtcgg tatgttgaga acatgatcg gtttgtacga        900 catggcgaga cacgcygtag aatcaaccgc acaatcagaa aataagatca cttggaacgt       960
aataagagat tcaatgagtg gaattttata tcaacttagc agtatgaaat ttaaggatcc      1020
cgtaaaagat ggtgaagcta aatcaaggc agattttgat caattatatg aagatattca       1080
rcaggccttc agaaacttag aagattaaat cttttttaagg aaattttcct attttgttca     1140
tcagtgtaag tttaaaaata tagcgatatt tatcaaaaag aataataagg cctctatccc      1200
tcacttctgt gaatattaat atggccgtac taawgatagt aactaaagat aggttttctc      1260
ttttttgata ttatcctgta caaaataaat tatgtaaatt gttgaatatg tgtatagttt      1320
ttttgggtga gggtacagtg cttattaaat acttttaaa cattttttccc gccattccaa      1380 ttactattaa gttttttcgt tttaatactt ttttaaatat acaggtgctt aatatcgttt      1440
atattttcag tattacttgg ttttcttcat gtaaattgtt ttaaatttttt cttttacccct    1500 tttaatcttg tatattacat tacccaatta aagttaattg tacagattaa gataaacgag      1560
tatcttataa catctattag attgtt                                           1586

<210> SEQ ID NO 46
<211> LENGTH: 688
<212> TYPE: DNA
<213> ORGANISM: Artificial sequence
<220> FEATURE:
<223> OTHER INFORMATION: Synthetic primer

<400> SEQUENCE: 46
agaaacataa catccatcca caaatatgtc gaaatcaagg atcggagatg aagagaagga        60
agggcagtat ggttacgtcc atgctgtctc aggtccagtc gttactgctg agaaaatgtc       120
tggttctgct atgtacgaac tggtacgtgt aggatactat gagctggtag gagaaatcat       180
tagattggaa ggtgacatgg ctactattca ggtatatgaa gaaacttctg gtgtaactgt       240
tggtgatcca gtattaagaa ctggtaaacc cctttcagta gaacttggac ctggtattat       300
gggttccatt tttgatggta tccaacgtcc attgaaagac atttgcgatg ctactgaaag       360
tatttacatc cctaagggta tcaatgtacc ttctttatcg agaactgcaa aatgggactt       420
caacccaatc aacatcaagt tgggatctca cttaactgga ggtgatatat atggtctagt       480
tcatgaaaac actcttgtca aacacaaaat gatactgcct cccaaagcta agggtactgt       540
aacctacatt gcagaaccag gaaaytacac agttgatgaa atagtattgg aaacagaatt       600
tgatggtgat cgtaccaaat atactatgtt gcaagtatgg cctgtacgtc aagcaagacc       660
agtaagtgaa aaattgccag ccaaccat                                         688

<210> SEQ ID NO 47
<211> LENGTH: 688
<212> TYPE: DNA
<213> ORGANISM: Artificial sequence
<220> FEATURE:
<223> OTHER INFORMATION: Synthetic primer

<400> SEQUENCE: 47
```

```
agaaacataa catccatcca caaatatgtc gaaagtaagg atcggagatg aagagaagga    60
agggcagtat ggttatgtcc atgctgtctc aggtccagtc gttactgctg agaaaatgtc   120
tggttctgct atgtacgaac tggtacgtgt cggatactat gagctggtag agaaatcat   180 tagattggaa ggtgacatgg ctactattca ggtatacgaa gaaacatcag gtgtaactgt   240
tggtgatcca gtattaagaa ctggtaaacc actttcagta gaacttggac ctggtattat   300
gggttccatt tttgatggta tccaacgtcc attgaaagac atttgtgacg ctactgatag   360
tatttacatc cccaagggta ttaacgtacc ttctttatcg agaacagcaa aatgggactt   420
caacccaatc aacatcaagt tgggatctca cttaactgga ggtgatatat atggtctagt   480
tcatgaaaac acccttgtca aacacaaaat gattctgcct cctagagcta agggtactgt   540
aacctacatt gcagaaccag gaaactacac tgttgatgaa gtagtattgg aaactgaatt   600
tgatggtgat cgtaccaaat atactatgtt gcaagtatgg cctgtacgtc aagcaaggcc   660
agtcagtgaa aaattacctg ccaaccat                                      688

<210> SEQ ID NO 48
<211> LENGTH: 1059
<212> TYPE: DNA
<213> ORGANISM: Artificial sequence
<220> FEATURE:
<223> OTHER INFORMATION: Synthetic primer

<400> SEQUENCE: 48
gtaactgttg gtgatccagt attaagaact ggtaaacccc tttcagtaga acttggacct    60
ggtattatgg gttccatttt tgatggtatc caacgtccat tgaaagacat ttgcgatgct   120
actgaaagta tttacatccc taagggtatc aatgtaccct ctttatcgag aactgcaaaa   180
tgggacttca acccaatcaa catcaagttg ggatctcact taactggagg tgatatatat   240
ggtctagttc atgaaaacac tcttgtcaaa cacaaaatga tactgcctcc caaagctaag   300
ggtactgtaa cctacattgc agaaccagga aattacacag ttgatgaaat agtattggaa   360
acagaatttg atggtgatcg taccaaatat actatgttgc aagtatggcc tgtacgtcaa   420
gcaagaccag taagtgaaaa attgccagcc aaccatcctc tgcttacagg acagcgtgta   480
cttgatgctc ttttcccatg tgtacagggt ggtactactg caattcccgg tgctttcggt   540
tgtgaaaaaa ctgtaatttc ccaatctctt tccaaatatt ccaactctga tgtcattatc   600
tacgtcggtt gcggagaaag aggtaacgaa atgtctgaag tattgagaga ttttcctgaa   660
ttgactgttg aaatagacgg gcacactgaa tctattatga acgtactgc attggttgcc   720 aacacctcta acatgcctgt agctgctcgt gaagcttcta tctatactgg tattactctt   780
tctgaatact tccgtgatat gggttacaac gtatctatga tggctgactc gacatcacgt   840
tgggccgaag ctttgagaga aatttcaggt cgtttggctg aaatgcctgc cgattccggt   900
tatccggctt acttgggtgc ccgtttggct tccttctacg aacgtgcagg tcgtgttaaa   960
tgtctaggta acccagacag agaaggatct gtttcaattg taggagccgt atcacctcct  1020
ggtggtgatt tctcagatcc tgttaccacc gctaccctt                         1059

<210> SEQ ID NO 49
<211> LENGTH: 1059
<212> TYPE: DNA
<213> ORGANISM: Artificial sequence
<220> FEATURE:
<223> OTHER INFORMATION: Synthetic primer
```

<400> SEQUENCE: 49

```
gtaacagttg gagatcctgt tctacgtact ggtaaaccat tgtcggtaga attaggtcct      60
ggtataatgg gttcaattt tgatggtatc cagcgtcctt tgaaagatat caaygttctc     120
acagaaagta tctacattcc caaaggtatc aacgtgcctt gcttgtctag aactgctaag    180
tgggacttca atcctaccaa cattaaaatg ggatctcact taactggtgg agatatttac    240
ggtattgtcc atgaaaatac tttggtaaaa caaaaactca tgttgccgcc aaagtctaaa    300
ggtacagtta cctatattgc tgaaccagga agttacactg tcgatgatgt tgttttggaa    360
actgaattcg atggcgaacg cacaaagtac actatgttgc aagtttggcc agtccgtcaa    420
ccgcgtccag tgagcgaaaa actgccagca aatcatcctc ttcttactgg acagagagtt    480
ttagattctc tctttccatg tgtacaaggg ggtaccactg ccatccctgg tgccttcggt    540
tgtggaaaaa ctgtaatctc tcaatctcta tccaaatatt ctaattctga tgtcatcatc    600
tatgtaggat gtggagaaag aggtaacgaa atgtctgaag tacttcgtga cttccccgaa    660
ctgacagtcg agatcgaagg ccagactgaa tccatcatga acgtaccgc ccttgtagcg     720
aacacgtcca acatgcctgt cgccgctcgt gaagcttcca tctacaccgg tatcacgttg    780
tctgagtact tccgtgacat gggttacaac gtgtccatga tggccgattc gacctcrcgt    840
tgggccgaag ccctgagaga aatctccggt cgtttggccg aaatgcccgc cgattccggt    900
taccccgcct acttggggc ccgtctsgcc tccttctacg agcgtgccgg tcgcgttaaa     960
tgcctgggta acccagatag agagggttcc gtctccatcg taggagccgt gtcgccwcct   1020
ggtggtgact tctcagatcc cgtcacgtca gcyactctc                          1059
```

<210> SEQ ID NO 50
<211> LENGTH: 26
<212> TYPE: DNA
<213> ORGANISM: Artificial sequence
<220> FEATURE:
<223> OTHER INFORMATION: Synthetic primer

<400> SEQUENCE: 50

```
tatttgtagt tgggtctttt ccaatc                                           26
```

<210> SEQ ID NO 51
<211> LENGTH: 26
<212> TYPE: DNA
<213> ORGANISM: Artificial sequence
<220> FEATURE:
<223> OTHER INFORMATION: Synthetic primer

<400> SEQUENCE: 51

```
gaaaagaccc aactacaaat agatgg                                           26
```

<210> SEQ ID NO 52
<211> LENGTH: 26
<212> TYPE: DNA
<213> ORGANISM: Artificial sequence
<220> FEATURE:
<223> OTHER INFORMATION: Synthetic primer

<400> SEQUENCE: 52

```
ccatctattt gtagttgggt cttttc                                           26
```

<210> SEQ ID NO 53
<211> LENGTH: 26
<212> TYPE: DNA
<213> ORGANISM: Artificial sequence

```
<220> FEATURE:
<223> OTHER INFORMATION: Synthetic primer

<400> SEQUENCE: 53
gacccaacta caaatagatg gaaccc                                              26

<210> SEQ ID NO 54
<211> LENGTH: 26
<212> TYPE: DNA
<213> ORGANISM: Artificial sequence
<220> FEATURE:
<223> OTHER INFORMATION: Synthetic primer

<400> SEQUENCE: 54
gggttccatc tatttgtagt tgggtc                                              26

<210> SEQ ID NO 55
<211> LENGTH: 26
<212> TYPE: DNA
<213> ORGANISM: Amphioxus floridae

<400> SEQUENCE: 55
aactacaaat agatggaacc cttaca                                              26

<210> SEQ ID NO 56
<211> LENGTH: 26
<212> TYPE: DNA
<213> ORGANISM: Anopheles gambiae

<400> SEQUENCE: 56
tgtaagggtt ccatctattt gtagtt                                              26

<210> SEQ ID NO 57
<211> LENGTH: 26
<212> TYPE: DNA
<213> ORGANISM: Acyrthosiphon pisum

<400> SEQUENCE: 57
caaatagatg gaacccttac aactat                                              26

<210> SEQ ID NO 58
<211> LENGTH: 26
<212> TYPE: DNA
<213> ORGANISM: Canis familiaris

<400> SEQUENCE: 58
atagttgtaa gggttccatc tatttg                                              26

<210> SEQ ID NO 59
<211> LENGTH: 26
<212> TYPE: DNA
<213> ORGANISM: Canis familiaris

<400> SEQUENCE: 59
agatggaacc cttacaacta ttgaaa                                              26

<210> SEQ ID NO 60
<211> LENGTH: 26
<212> TYPE: DNA
<213> ORGANISM: Daphnia magna

<400> SEQUENCE: 60
tttcaatagt tgtaagggtt ccatct                                              26
```

<210> SEQ ID NO 61
<211> LENGTH: 26
<212> TYPE: DNA
<213> ORGANISM: Diabrotica balteata

<400> SEQUENCE: 61
gaacccttac aactattgaa atgcag          26

<210> SEQ ID NO 62
<211> LENGTH: 26
<212> TYPE: DNA
<213> ORGANISM: Diabrotica barberi

<400> SEQUENCE: 62
ctgcatttca atagttgtaa gggttc          26

<210> SEQ ID NO 63
<211> LENGTH: 26
<212> TYPE: DNA
<213> ORGANISM: Diabrotica undecimpunctata

<400> SEQUENCE: 63
cttacaacta ttgaaatgca gaggga          26

<210> SEQ ID NO 64
<211> LENGTH: 26
<212> TYPE: DNA
<213> ORGANISM: Diabrotica virgifera zeae

<400> SEQUENCE: 64
tccctctgca tttcaatagt tgtaag          26

<210> SEQ ID NO 65
<211> LENGTH: 26
<212> TYPE: DNA
<213> ORGANISM: Fugu rubripes

<400> SEQUENCE: 65
aactattgaa atgcagaggg aagccc          26

<210> SEQ ID NO 66
<211> LENGTH: 26
<212> TYPE: DNA
<213> ORGANISM: Gallus gallus

<400> SEQUENCE: 66
gggcttccct ctgcatttca atagtt          26

<210> SEQ ID NO 67
<211> LENGTH: 26
<212> TYPE: DNA
<213> ORGANISM: Glossina morsitans

<400> SEQUENCE: 67
ttgaaatgca gagggaagcc ctcgaa          26

<210> SEQ ID NO 68
<211> LENGTH: 26
<212> TYPE: DNA
<213> ORGANISM: Locusta migratoria

<400> SEQUENCE: 68
ttcgagggct tccctctgca tttcaa          26

```
<210> SEQ ID NO 69
<211> LENGTH: 26
<212> TYPE: DNA
<213> ORGANISM: Pan troglodytes

<400> SEQUENCE: 69
atgcagaggg aagccctcga aggagc                                          26

<210> SEQ ID NO 70
<211> LENGTH: 26
<212> TYPE: DNA
<213> ORGANISM: Pan troglodytes

<400> SEQUENCE: 70
gctccttcga gggcttccct ctgcat                                          26

<210> SEQ ID NO 71
<211> LENGTH: 26
<212> TYPE: DNA
<213> ORGANISM: Strongylocentrotus purpuratus

<400> SEQUENCE: 71
gagggaagcc ctcgaaggag ctagca                                          26

<210> SEQ ID NO 72
<211> LENGTH: 26
<212> TYPE: DNA
<213> ORGANISM: Xenopus laevis

<400> SEQUENCE: 72
tgctagctcc ttcgagggct tccctc                                          26

<210> SEQ ID NO 73
<211> LENGTH: 26
<212> TYPE: DNA
<213> ORGANISM: Artificial sequence
<220> FEATURE:
<223> OTHER INFORMATION: Synthetic primer

<400> SEQUENCE: 73
aagccctcga aggagctagc acaaat                                          26

<210> SEQ ID NO 74
<211> LENGTH: 26
<212> TYPE: DNA
<213> ORGANISM: Artificial sequence
<220> FEATURE:
<223> OTHER INFORMATION: Synthetic primer

<400> SEQUENCE: 74
atttgtgcta gctccttcga gggctt                                          26

<210> SEQ ID NO 75
<211> LENGTH: 42
<212> TYPE: DNA
<213> ORGANISM: Artificial sequence
<220> FEATURE:
<223> OTHER INFORMATION: Synthetic primer

<400> SEQUENCE: 75
taatacgact cactataggg acaggaaaca gctatgacca tg                        42

<210> SEQ ID NO 76
```

<211> LENGTH: 28
<212> TYPE: DNA
<213> ORGANISM: Artificial sequence
<220> FEATURE:
<223> OTHER INFORMATION: Synthetic primer

<400> SEQUENCE: 76
taatacgact cactataggg cgaattgg					28

<210> SEQ ID NO 77
<211> LENGTH: 27
<212> TYPE: DNA
<213> ORGANISM: Artificial sequence
<220> FEATURE:
<223> OTHER INFORMATION: Synthetic primer

<400> SEQUENCE: 77
ctagtaagcc ctcgaaggag ctagcag					27

<210> SEQ ID NO 78
<211> LENGTH: 27
<212> TYPE: DNA
<213> ORGANISM: Artificial sequence
<220> FEATURE:
<223> OTHER INFORMATION: Synthetic primer

<400> SEQUENCE: 78
aattctgcta gctccttcga gggctta					27

<210> SEQ ID NO 79
<211> LENGTH: 27
<212> TYPE: DNA
<213> ORGANISM: Artificial sequence
<220> FEATURE:
<223> OTHER INFORMATION: Synthetic primer

<400> SEQUENCE: 79
ctagtagccc tcgaaggagc tagcacg					27

<210> SEQ ID NO 80
<211> LENGTH: 27
<212> TYPE: DNA
<213> ORGANISM: Artificial sequence
<220> FEATURE:
<223> OTHER INFORMATION: Synthetic primer

<400> SEQUENCE: 80
aattcgtgct agctccttcg agggcta					27

<210> SEQ ID NO 81
<211> LENGTH: 27
<212> TYPE: DNA
<213> ORGANISM: Artificial sequence
<220> FEATURE:
<223> OTHER INFORMATION: Synthetic primer

<400> SEQUENCE: 81
ctagtgccct cgaaggagct agcacag					27

<210> SEQ ID NO 82
<211> LENGTH: 27
<212> TYPE: DNA
<213> ORGANISM: Artificial sequence
<220> FEATURE:
<223> OTHER INFORMATION: Synthetic primer

<400> SEQUENCE: 82
aattctgtgc tagctccttc gagggca            27

<210> SEQ ID NO 83
<211> LENGTH: 27
<212> TYPE: DNA
<213> ORGANISM: Artificial sequence
<220> FEATURE:
<223> OTHER INFORMATION: Synthetic primer

<400> SEQUENCE: 83
ctagtccctc gaaggagcta gcacaag            27

<210> SEQ ID NO 84
<211> LENGTH: 27
<212> TYPE: DNA
<213> ORGANISM: Artificial sequence
<220> FEATURE:
<223> OTHER INFORMATION: Synthetic primer

<400> SEQUENCE: 84
aattcttgtg ctagctcctt cgaggga            27

<210> SEQ ID NO 85
<211> LENGTH: 27
<212> TYPE: DNA
<213> ORGANISM: Artificial sequence
<220> FEATURE:
<223> OTHER INFORMATION: Synthetic primer

<400> SEQUENCE: 85
ctagtcctcg aaggagctag cacaaag            27

<210> SEQ ID NO 86
<211> LENGTH: 27
<212> TYPE: DNA
<213> ORGANISM: Artificial sequence
<220> FEATURE:
<223> OTHER INFORMATION: Synthetic primer

<400> SEQUENCE: 86
aattctttgt gctagctcct tcgagga            27

<210> SEQ ID NO 87
<211> LENGTH: 27
<212> TYPE: DNA
<213> ORGANISM: Artificial sequence
<220> FEATURE:
<223> OTHER INFORMATION: Synthetic primer

<400> SEQUENCE: 87
ctagtctcga aggagctagc acaaatg            27

<210> SEQ ID NO 88
<211> LENGTH: 27
<212> TYPE: DNA
<213> ORGANISM: Artificial sequence
<220> FEATURE:
<223> OTHER INFORMATION: Synthetic primer

<400> SEQUENCE: 88
aattcatttg tgctagctcc ttcgaga            27

<210> SEQ ID NO 89
<211> LENGTH: 27
<212> TYPE: DNA

```
<213> ORGANISM: Artificial sequence
<220> FEATURE:
<223> OTHER INFORMATION: Synthetic primer

<400> SEQUENCE: 89
ctagttcgaa ggagctagca caaatag                                          27

<210> SEQ ID NO 90
<211> LENGTH: 27
<212> TYPE: DNA
<213> ORGANISM: Artificial sequence
<220> FEATURE:
<223> OTHER INFORMATION: Synthetic primer

<400> SEQUENCE: 90
aattctattt gtgctagctc cttcgaa                                          27

<210> SEQ ID NO 91
<211> LENGTH: 593
<212> TYPE: DNA
<213> ORGANISM: Artificial sequence
<220> FEATURE:
<223> OTHER INFORMATION: Synthetic primer

<400> SEQUENCE: 91
tattttctgc tgaagactca tttgtgacaa gcttcctgaa gttttactct agatttaacc      60
atttctacac cttctgagga ggtttccaca cactagacag acaacatgag tctcatagcg     120
aagatgtttg gcggtggcaa gaagcaggcc cagccaacgc cgggagaagc catccaaaag     180
ttgagggaga ccgaagagat gttggaaaag aaatcggaat ttttggagtc caaggtgcaa     240
aaggagttag cgatagcaaa aagaacggc acaaagaaca agagagttgc actgcaggct      300
ctgaagagga agaagcgtta tgagaagcag ttgactcaga tcgatggtac actgtccacc     360
atcgagttcc agagggaagc actggagaat gccaacacca acacagaagt actgaagaca     420
atgggctatg cagcaaaggc tcttaaagca gctcatcaac acttggatgt ggaccaggtc     480
gacgacctga tggcagacat acaggaacag caggacattg cacaggagat ctctgatgcc     540
atctccaaac tgttggctt tggggaggat gttgatgagg atgacctgat ggc             593

<210> SEQ ID NO 92
<211> LENGTH: 865
<212> TYPE: DNA
<213> ORGANISM: Artificial sequence
<220> FEATURE:
<223> OTHER INFORMATION: Synthetic primer

<400> SEQUENCE: 92
gcgcgccagc acagtgaaaa aacgatgagt ttcttcggga agctgttttc ggggaaaaag      60
ggcgaaccag ccccgacacc gagcgaagcg atacaaaagc tgcgagacat agaaaatatg     120
ctcaccaaaa agcaggagtt cctagagaag aaaatcgagg tcgagataga tacggccagg     180
aaaaatggta ccaaaaacaa acgagcggcc atccaggcgc tgaagcggaa gaagcggtac     240
gagaaacagc tacagcaaat cgatggcaca cttttcgacga ttgaaatgca gcgagaggcg     300
ctggagaatg cgaacacaaa cgccgaagtg ctgaagacga tgaagaaggc ttccgatgcg     360
cttaaagtta cccataagga tatgaacatt gatgatgtgc acgatctgat ggatgacatt     420
gccgaacaga cgacatcgc gaacgaaatt tccaatgccg tgtccagtgc cgtcggcttc     480
ggccaggacg acgaggacga gctggagaag gagctcgagg agctggagca ggaagagctg     540
gacaaagagc tgctgggcgt gcagccagaa acggacgagc tacccgaggt tccctccacg     600
```

```
gacttgccgg ccaaggcaaa ggagaaggag aaaaagaaag ctgccgtcgc cgaagaagac      660
gatccggaca tgaaggagtt gatgtcatgg gcaaactaat tctgaccggc tcaggaggtg      720
atgataacag ccaatcccac acacacacat acacatacac atactgcata aaagagagga      780
ccgtactctt tttgtgtgca gtttgcttac gttagtgttt aattttgtgc gaagttaatc      840
cacttacatt tattatttgc gttcg                                            865
```

<210> SEQ ID NO 93
<211> LENGTH: 884
<212> TYPE: DNA
<213> ORGANISM: Artificial sequence
<220> FEATURE:
<223> OTHER INFORMATION: Synthetic primer

<400> SEQUENCE: 93

```
atttagtgcg acttatcgtt aatcgttgct gtttttgtga ctgttgatta ttgactattg       60
acttgttgta atttgtatac ggtacctttg aatgattatg ttaattgcat aaataggtta      120
ataaagttaa tataaataat atattgtaca ctatgagttt cctgggtaag attttcggta      180
gcaaaaagga agagaaagga ccttcgacgg aagatgcgat acaaaagctt cgatccacag      240
aagagatgct gataaaaaaa caagaatttt tagaaaaaaa aattgaacaa gaagtagcga      300
tagcaaaaaa aaatggtaca actaataaac gagctgcatt gcaagccttg aagcgtaaga      360
aacggtatga acaacaacta gcgcaaattg atggtaccat gttaactatt gaacaacagc      420
gagaggcatt agaaggtgct aacacaaata cagcagtatt aactacgatg aaaacagctg      480
cagatgcact gaaatcggct catcaaaata tgaatgttga tgatgttcac aatatgatgg      540
atgatatagc agagtcacaa gatttatcca agaaatatc agaagctatt tcaaatccag      600
ttgcatttgg aactgatgta gacgaagatg aattacaaaa ggaattggaa gagctagaac      660
aagaagaatt ggacaaagag ttgttgaata caggcaagac acctgtcaac gatttgccaa      720
cgcctgcagt gccaacattt gagcccagtg gccgaggcaa agcaaaaact aaagctgaag      780
aggatgatga tgaaatgaaa gaattagcta attgggcttc ataaaaaaat gtttaagtga      840
cgtcaaaata tttgatggta aacatgataa aaaaaatatt ttta                       884
```

<210> SEQ ID NO 94
<211> LENGTH: 558
<212> TYPE: DNA
<213> ORGANISM: Artificial sequence
<220> FEATURE:
<223> OTHER INFORMATION: Synthetic primer

<400> SEQUENCE: 94

```
cgagggtgga catgagtggt ctcggcagac tcttcgggag ggggaagaag gagaagggac       60
caacccctga ggaggcaata cagaaactga aggagacaga gaagatattg ataaagaaac      120
aggagtttct ggagcagaag attcaacagg agttacaaat ggccaagaag catgggatca      180
aaaataagag agccgcccta caggctttgc ggaggaagaa aagattggaa cagcagctgg      240
cacaaaccga tgggacatta tccaccctgg agtttcagcg tgaggccatt gagaatgcca      300
ccaccaatgc agaagtgctt cgtaccatgg agcttgctgc ccaaggcatg aagaaggcct      360
accaggacat ggacattgac aaggtggatg aactgatggc tgacattaca gaacaacaag      420
aggtggccca gcagatttca gatgccattt ctcggcctgt gggctttgga gatgttgtag      480
atgaggatga gctattggaa gagctagagt tgctggagca ggaggaactg gctcgggact      540
```
tgttaaccgt gggtgaca                                                558

<210> SEQ ID NO 95
<211> LENGTH: 614
<212> TYPE: DNA
<213> ORGANISM: Artificial sequence
<220> FEATURE:
<223> OTHER INFORMATION: Synthetic primer

<400> SEQUENCE: 95
agctgtgggg cggaggcggc ggagaggcct gcggcggcag ggagcggcgg gacccggagc    60
gggcgctgga gccaagccga gccgagccgg agcgggcggc gcaggccggc gcggcgagca   120
gcaaccatgt cggtgttcgg gaaactgttc ggggcaggag ggggtaaggc cggcaagggc   180
ggtgggaccc ctcaagatgc catccagcgg ctgcgggaca cggaggagat gctaagtaaa   240
aaacaggaat tcctggagac caagatcgag caggagctga ccgctgccaa gaagcacggc   300
accaaaaaca agcgcgcggc cctccaggca ctgaagcgca agaaggta tgaaaagcag     360
ctggcgcaga tcgacggcac actatcaacc atcgagtttc agcgggaagc cctggagaat   420
gccaatacca acaccgaggt gctcaagaac atgggctatg ctgctaaggc gatgaaggct   480
gcccatgaca acatggacat cgataaagtt gatgaattaa tgcaggacat tgctgaccag   540
caagaacttg cagaggagat ttcaacagct atttcaaaac ctgtaggatt tggagaagag   600
tttgatgagg atga                                                    614

<210> SEQ ID NO 96
<211> LENGTH: 618
<212> TYPE: DNA
<213> ORGANISM: Artificial sequence
<220> FEATURE:
<223> OTHER INFORMATION: Synthetic primer

<400> SEQUENCE: 96
tgaagttcgc caataatttg tttaggaacg tctaatttag tgaaaatgag ttttcttcaa    60
aaaatgtttg ggtctggtgg caaagataaa ggcatgccca ctaccgggca agctatacaa   120
aagttaagag aaactgagga aatgctgatt aagaaacaag aatttcttga aaaaaaaatt   180
gaccaagaat tggatattgc taaaaagaat ggaactaaaa acaaaagagt tgctattcag   240
gccctaaaac ggaagaagag gtatgagaag caactccagc agattgatgg cactatttca   300
actattgaaa tgcaaagaga agctttggag ggagcaaata ccaatacagc ggttcttcag   360
acaatgggcg atgctgctaa agcactaaaa gcagctcatc agcatatgga tgtgacaag    420
gtacatgaca tgatggatga cattgctgag caacaggaag ttgcacgaga aatctcagaa   480
gccatttcta atccagtggc ctttggtcaa gatattgatg aagatgaatc ggagagagag   540
tcggaagaat cggaccagga agagctggat aatgaatggc tgaatgttcc agcagctgca   600
gctctgccat ctgtgcct                                                618

<210> SEQ ID NO 97
<211> LENGTH: 538
<212> TYPE: DNA
<213> ORGANISM: Artificial sequence
<220> FEATURE:
<223> OTHER INFORMATION: Synthetic primer

<400> SEQUENCE: 97
agagagactg aagaaatgtt aataaaaaaa caggattttt tagaaaagaa grtagaagaa    60
tataccttag tagcaaagaa aaatgcgtcg aaaaataaaa gagttgcacy ccaagctctc   120

```
aaaaagaaga aacgattgga aaagacccaa ctacaaatag atggaacmct tacaactatt    180
gaaatgcaga gggaagccct cgaaggagct agcacaaata ctgctgtatt agattctatg    240
aaaaatgctg cagatgccct taagaaagct cataagaact tgaatgtgga tgatgttcac    300
gacatcatgg atgacatagc cgaacaacac gacatagcca acgaaatcac aaacgctatt    360
agcaaccctg ttggattcac cgacgatctg gacgaygatg aattagagaa agaattagaa    420
gagctcgaac aagaaggatt ggaagaagac ctgcttcaag tgccaggtcc cactcaactg    480
ccggctgtgc ctactgatgc agttgctaat aaaccaatca aaccagcagc tagaaaag     538
```

<210> SEQ ID NO 98
<211> LENGTH: 538
<212> TYPE: DNA
<213> ORGANISM: Artificial sequence
<220> FEATURE:
<223> OTHER INFORMATION: Synthetic primer

<400> SEQUENCE: 98

```
agagagactg aagaaatgtt aataaaaaaa caggattttt tagaaaagaa gatagaagaa     60
tttaccatgg tagcaaagaa aaatgcgtcg aaaaataaaa gagttgcact ccaagccctc    120
aaaaagaaga acgattgga aaagactcaa ctacaaatag atggaaccct tacaactatt    180
gaaatgcaga gggaagccct cgaaggagct agcacaaata ctgctgtatt agattctatg    240
aaaaatgctg cagatgccct taagaaagct cataagaatt tgaatgtaga tgatgttcac    300
gatatcatgg atgacatagc cgaacaacac gacatagcca acgaaattac aaatgctatt    360
agcaaccctg ttggattcac cgacgatctg gacgacgatg aattagaaaa agaattagaa    420
gagctcgaac aagaaggatt ggaagaagac ctgctccaag tgccaggtcc aactcaactg    480
ccggctgtgc ctgctgatgc agttactact aaaccaatca aaccagcagc taaaaaag     538
```

<210> SEQ ID NO 99
<211> LENGTH: 538
<212> TYPE: DNA
<213> ORGANISM: Artificial sequence
<220> FEATURE:
<223> OTHER INFORMATION: Synthetic primer

<400> SEQUENCE: 99

```
agagagactg aagaaatgtt aataaaaaaa caggattttt tagagaagaa gatagaagaa     60
tttaccttag tagcaaagaa aaatgcgtcg aaaaataaaa gagttgcact ccaagccctc    120
aaaaagaaga aacgattgga aaagacccaa ctacaaatag atggaaccct tacaactatt    180
gaaatgcaga gggaagccct cgaaggagct agcacaaata ctgctgtatt agattctatg    240
aaaaatgctg cagatgccct taagaaagct cataagaact tgaatgtgga tgatgttcac    300
gacatcatgg atgacatagc cgaacaacac gacatagcca acgaaatcac aaacgctatt    360
agcaatcctg ttggattcac cgacgatctg gacgatgatg aattagagaa agaattagaa    420
gagctcgaac aagaaggatt ggaagaagac ctgcttcaag tgccaggtcc aactcaactg    480
ccggctgtgc ctactgatgc agttgctaat aaaccaatta aaccagcagc tagaaaag     538
```

<210> SEQ ID NO 100
<211> LENGTH: 538
<212> TYPE: DNA
<213> ORGANISM: Artificial sequence
<220> FEATURE:
<223> OTHER INFORMATION: Synthetic primer

<400> SEQUENCE: 100

| | |
|---|---|
| agagagactg aagaaatgtt aataaaaaaa caggatttttt tagaaaagaa gatagaagaa | 60 |
| tttaccatgg tagcaaagaa aaatgcgtcg aaaaataaaa gagttgcact ccaagccctc | 120 |
| aaaaagaaga aacgattgga aaagacccaa ctacaaatag atggaaccct tacaactatt | 180 |
| gaaatgcaga gggaagccct cgaaggagct agcacaaata ctgctgtatt agattctatg | 240 |
| aaaaatgctg cagatgccct taagaaagct cataagaatt tgaatgtaga tgatgttcac | 300 |
| gatatcatgg atgacatagc cgaacaacac gacatagcca acgaaatcac aaacgctatt | 360 |
| agcaatcctg tcggattcac cgacgatctg gatgacgatg aattagaaaa agaattagaa | 420 |
| gagctcgaac aagaaggatt ggaagaagac ctgctccaag tgccaggtcc aactcaactg | 480 |
| ccggctgtgc ctgctgatgc agttgctact aaaccaatca aaccagcagc taaaaaag | 538 |

<210> SEQ ID NO 101
<211> LENGTH: 543
<212> TYPE: DNA
<213> ORGANISM: Artificial sequence
<220> FEATURE:
<223> OTHER INFORMATION: Synthetic primer

<400> SEQUENCE: 101

| | |
|---|---|
| gattttatttt tttataattg aagacgata gcctcctaga tatgtcattg ctaagcaaaa | 60 |
| tatttggagg aggaaaagga gcaaaggcac cgagtccaca ggaggcgatc cagaaactcc | 120 |
| gagagacgga ggacatgcta acgaagaaac aggaaatgtt ggagaataaa atcgaacagg | 180 |
| aacttcaaac agccaagaaa aatggcacga aaaacaagcg agcggcactg caagccttaa | 240 |
| aaagaaagaa gcgctatgag aaacagctcg cccagattga tggaacactg tcgaccatcg | 300 |
| agttccagag agaagcttta gagaacgcca acaccagcac tgaggtgctc aagaacatgg | 360 |
| gctttgctgc caaggccttg aaagctgccc ataaagactt ggacattgac aaagtggatg | 420 |
| atctaatgca ggacatcaca gaacagcagg agctggctca ggaaatctct gacgcaatct | 480 |
| ccaaacccgt tgggttgggt gaacagtttg atgaggatga cctgatggcc gagctggatg | 540 |
| agc | 543 |

<210> SEQ ID NO 102
<211> LENGTH: 598
<212> TYPE: DNA
<213> ORGANISM: Artificial sequence
<220> FEATURE:
<223> OTHER INFORMATION: Synthetic primer

<400> SEQUENCE: 102

| | |
|---|---|
| tggtatggtc tgtttcggga ccacttattt ccagcaagtt tttgtctaat tcttcttgtt | 60 |
| ctagttcctc tagttctgcc atgagttcat cctcatcaaa ttcctcccca aatcctactg | 120 |
| gctttgagat cgctgttgaa atctcatctg ccagctcttg ctgctccgca atgtcctgca | 180 |
| ttaattcatc tactttatca atatccatgt tgtcatgagc agctttcata gctttagcag | 240 |
| caaaacccat attcttaagc acttcagtgt tggtgttggc attctccaag gcttccctct | 300 |
| gaaattcgat tgtggacaac gtgccatcta tctgtgcaag ctgcttctca tacctcttct | 360 |
| tacgctttag ggcctgaaga gcagcgcgct tgttcttggt gccgtgtttg cgggcggccg | 420 |
| ccagctcctg ctcgatcttc ttctccagga actcctgctt cttgctcagc atctcctccg | 480 |
| tgtcccgcag ccgctggatg gcctcctgag gggacgggcc cttccggcg ccttccgc | 540 |
| cggcgccggc cccgaacagc ttccccagga tccccgacat ggctgcgcta tgccgggc | 598 |

<210> SEQ ID NO 103
<211> LENGTH: 501
<212> TYPE: DNA
<213> ORGANISM: Artificial sequence
<220> FEATURE:
<223> OTHER INFORMATION: Synthetic primer

<400> SEQUENCE: 103

| | | | | | |
|---|---|---|---|---|---|
| gcgaaacaga | aaatatgcta | attaagaagc | aggaatttct | cgaatctaaa | attgaggagg | 60 |
| aattgaacat | agcacgtaaa | aatgcttcga | aaaataaaag | agtggctttg | caagctttaa | 120 |
| aaaaaaaaaa | gcgcttagaa | aagcaattgc | aacaaatcga | tggcactctg | tcaacaattg | 180 |
| aaatgcaacg | agaagcattg | gaaagtgcta | acacgaatac | cgctgtcttg | acaactatga | 240 |
| aaaatgctgc | agatgctttg | aaggctgccc | accaaaatat | ggacgtggac | aaagtgcacg | 300 |
| acatgatgga | cgatatagcc | gaacaacagg | acgtagcacg | agaaatttct | gaagccattt | 360 |
| caaatccagt | agcctttggt | gctgacatag | atgatgaaga | cttggaacgt | gaattagacg | 420 |
| aattggagca | agagaacttt | gataaagaaa | tcattggaat | acccgaacca | gccgcgacgc | 480 |
| tacccgaggt | acccgctgat | g | | | | 501 |

<210> SEQ ID NO 104
<211> LENGTH: 597
<212> TYPE: DNA
<213> ORGANISM: Artificial sequence
<220> FEATURE:
<223> OTHER INFORMATION: Synthetic primer

<400> SEQUENCE: 104

| | | | | | |
|---|---|---|---|---|---|
| aattccgaaa | ataataattg | aagagtgtat | attgcataat | ttatggggcc | aacattttta | 60 |
| actaaaagta | tacgaacgat | ttagtgtata | aaaagattgt | caacatgagt | tttttaagca | 120 |
| aggtattggg | tggtaaaaag | gaggagaagg | cccccagcac | tggggaagca | atacaaaagt | 180 |
| tgagagagac | agaagaaatg | cttataaaga | aacaggagtt | tttagaaaag | aaaatcgaac | 240 |
| aagaaatcgc | aatggcacga | aagaatggaa | cgaagaataa | gcgggctgct | atacaggcac | 300 |
| tcaagagaaa | gaagcgatat | gaaaaacaac | tgcaacagat | ggatgaaact | ttatcaacaa | 360 |
| tggagatgca | acgagaagct | cttgaaggag | caaataccaa | tactgctgta | ctccaaacaa | 420 |
| tgaaaagtgc | ctctgatgct | cttaaggctg | ctcatcaaca | tatgaatgtt | gacgatgtac | 480 |
| atgacatgat | ggatgatatt | gcggaacaac | aggatgtagc | aagagaaata | tcagatgcca | 540 |
| tttcaaatcc | tgtcgcatgt | gggcaggatg | tagatgagga | tgaacttgaa | cgtgaat | 597 |

<210> SEQ ID NO 105
<211> LENGTH: 1515
<212> TYPE: DNA
<213> ORGANISM: Artificial sequence
<220> FEATURE:
<223> OTHER INFORMATION: Synthetic primer

<400> SEQUENCE: 105

| | | | | | |
|---|---|---|---|---|---|
| atgaacactg | caaggtacgt | tttcaggaat | tgcatggctt | ccttccaagg | agaccacacg | 60 |
| tcatttcaaa | ggctcacggc | caaaaaaaac | ccgcaccaac | cgatctcact | gcagcccag | 120 |
| aagaaacgct | cccacccgc | tcctcaggcc | ctgcccagcc | ttgtggcctc | ccttcacccg | 180 |
| ccgccaccat | ccgcggagcc | aaagcggagc | cctggtctcc | cgcggccggg | gatgggggct | 240 |
| ggaagctccc | ggatcaccctc | gctgccggca | atgctccacc | tggcagtgct | gcccgatgtc | 300 |

```
caactccgcc atctctccga cgccgtaagg ggcggggcaa agcctgaggg gcggggcaat      360
gagcgcgcgc ggcgcctgac gggagagtgg cggacccaga ggcggagtct acaggtgggg      420
gcggggcctg gaaaccagct gtgcattcgc cgtgaccagg aaaggccact gttctgcgac      480
ctcaccacac tctcctactc tcctcttctg tctccaagtg ccagcgacag tgaccttttc      540 tcaacccta agggccgggt ggcgccggcc agccgacgtc ccagcggtgg cctcccgcc       600 cagccgctgt gcagcgggc ggggccgaac tggcagccag gaaatgccct ggggtgtgtg      660
tcacctgtcc aggacgactt gttgattccc aggagcgccg cctttccggt ctgggtcccc      720
gagaggactg ccttgctcac ctgtcccctc ggcgcggccc cggggagctc ccgagaggcc      780
cccgggatcg ctcgccctcc gaactccaca gcaatgagca agttgggcaa gttctttaaa      840
gggggcggct cttctaagag ccgagccgct cccagtcccc aggaggccct ggtccgactt      900
cgggagactg aggagatgct gggcaagaaa caagagtacc tggaaaatcg aatccagaga      960
gaaatcgccc tggccaagaa gcacggcacg cagaataagc gagctgcatt acaggcacta     1020
aagagaaaga agaggttcga gaaacagctc actcagattg atggcacact ttctaccatt     1080
gagttccaga gagaagccct ggagaactca cacaccaaca ctgaggtgtt gaggaacatg     1140
ggctttgcag caaaagcgat gaaatctgtt catgaaaaca tggatctgaa caaaatagat     1200
gatttgatgc aagagatcac agagcaacag gatatcgccc aagaaatctc agaagcattt     1260
tctcaacggg ttggctttgg tgatgacttt gatgaggatg agttgatggc agaacttgaa     1320
gaattggaac aggaggaatt aaataagaag atgacaaata ccgccttcc aaatgtgcct     1380 tcctcttctc tcccagcaca gccaaataga aaaccaggca tgtcgtccac tgcacgtcga     1440
tcccgagcag catcttcccg gagggcagaa gaagaggatg atgatatcaa acaattggca     1500
gcttgggcta cctaa                                                     1515

<210> SEQ ID NO 106
<211> LENGTH: 942
<212> TYPE: DNA
<213> ORGANISM: Artificial sequence
<220> FEATURE:
<223> OTHER INFORMATION: Synthetic primer

<400> SEQUENCE: 106
atgtcggtgt tcgggaagct gttcggggct ggaggggggta aggccggcaa gggcggcccg       60
accccccagg aggccatcca gcggctgcgg gacacggaag agatgttaag caagaaacag      120
gagttcctgg agaagaaaat cgagcaggag ctgacggccg ccaagaagca cggcaccaaa      180
cacaagcgcg gtgaggctgc ccggcccctt cagacttgcc acgggctccc cccaggctcc      240
ccggccccgg acttcacctt catcagactc gcctcggggt ctggtctgac cctggaactc      300
tccgggtcag acttcttgcc ggcggccctc caggcactga agcgtaagaa gaggtatgag      360
aagcagctgg cgcagatcga cggcacatta tcaaccatcg agttccagcg ggaggccctg      420
gagaatgcca acaccaacac cgaggtgctc aagaacatgg gctatgccgc caaggccatg      480
aaggcggccc atgacaacat ggacatcgat aaagttgatg agttaatgca ggacattgct      540
gaccagcaaa acttgcaga ggagatttca acagcaattt ccaaacctgt agggtttgga      600
gaagagtttg acgaggatga gctcatggcg gaattagaag aactagaaca ggaggaacta      660
gacaagaatt tgctggaaat cagtggaccc gaaacagtcc ctctaccaaa tgttccctct      720
atagccctac catcaaaacc cggcaccaag gagcagtctc cctacagcct ggagaggagg      780
ctggccacag ggcagggctg tttgacagcc ctcatttccg gccagaacat gttgaacgca      840
```

```
ccagtcatcc taaatagcct tttctgtctt cacacagcca agaagaaaga agaggaggac    900
gacgacatga aggaattgga gaactgggcc ggatccatgt aa                       942
```

<210> SEQ ID NO 107
<211> LENGTH: 714
<212> TYPE: DNA
<213> ORGANISM: Diabrotica barberi
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t

<400> SEQUENCE: 107

```
acacgcgtcc ggaagcgaaa caataaagct ctccaatttg tacaacagag tattatatag     60
agacgcacga gagaataacc tgtcattttg ttttctagta gtattatctc tactactaag    120
agtaagactg gcccttcttc ttgtaattgt tgtcaacccg gtatcgtcag cgacggaggc    180
cttttccctt gacttgtctt cataatcagc tctgcttgcc gcgacgttcg attccaacat    240 ttttttcct ccaagttccc aaaatgagtg ggttcctatt tggaaagaag aagaaggagg     300
taactgtttc gccagcagaa gctatccaga aacttagatc aaccgaagaa atgctcgtga    360
aaaaacaaga gtttttagaa ggaaaggtgt caaaggaact tgtcatagca aagcagaatg    420
gaacgaaaaa taagagagtt gcaatccaag cgctgaaaag gaagaagaag tatgagaagc    480
agctggccca agttgatgga accttgacta cgatagaagc acagagggag gcgctggaga    540
atgctaatac caatgcagag gtcctcaaaa atatgnaatt tgcaagcaca gccttaaaaa    600
cagcacataa agaaatgggg tgtntgaaga tgtngnatga ttttgatggg cagatgtgca    660
tngaacaaat gggaactagc cancagaaat tttctgatgc cantctcaaa tcca          714
```

<210> SEQ ID NO 108
<211> LENGTH: 781
<212> TYPE: DNA
<213> ORGANISM: Diabrotica undecimpunctata
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t -continued

```
<400> SEQUENCE: 108
cagggagaag cgcgtggcgg ccctcaggca catacagcaa tactttaacc actttccttg      60
taccggcggc tccgggaggg gaaatgtctt tgatcgggaa gttgttcggt accgggggca     120
aaggagccaa aggcccaagc ccccaggaag ccatccagaa actacgggac acagaagaga     180
tgctggccaa aaacaggag ttcctggaga agaagatcga acaggagctt gtgacggcaa      240
agaagcacgg caccaagaac aagagggccg ccttgcaagc tctgaaacgt aagaagcgat     300
atgagaagca gctggcccag attgatgcca cgctatcaac catcgaattc cagagggaag     360
cccttgaaaa tgccaacaca aatactgaag ttctcaagaa tatgggcttt gcagctaagg     420
caatgaaagc tgctcatgat aacatggata ttgaaaaggt ggatgaactc atgcaagata     480
ttgctgatca acaggaactt gctcaggaaa tctcagatgc catttccaag ccagttggat     540
ttggagagga ctttgatgaa gatgaactaa tggcggagct ggaagaacta gaacaggaag     600
aattagacaa aaatctactg gaagtccaag gtccggagac tgtgcctctc cccaatgtgc     660
ctgcagcctc gttgccagca aaaccagtca agaaaaagca agaggaggat gacgacgaca     720
tgagagaatt anaaaattgg gccactgcat agatgcccaa ctgctgcatg aanttgcaca     780
g                                                                    781

<210> SEQ ID NO 109
<211> LENGTH: 36
<212> TYPE: DNA
<213> ORGANISM: Diabrotica virgifera

<400> SEQUENCE: 109
taatacgact cactatagga cttcaaccca atcaac                                36

<210> SEQ ID NO 110
<211> LENGTH: 23
<212> TYPE: DNA
<213> ORGANISM: Diabrotica barberi

<400> SEQUENCE: 110
gaatcatttt gtgtttgaca agg                                              23

<210> SEQ ID NO 111
<211> LENGTH: 21
<212> TYPE: DNA
<213> ORGANISM: Diabrotica balteata

<400> SEQUENCE: 111
gacttcaacc caatcaacat c                                                21

<210> SEQ ID NO 112
<211> LENGTH: 37
<212> TYPE: DNA
<213> ORGANISM: Diabrotica undecimpunctata

<400> SEQUENCE: 112
taatacgact cactatagga atcattttgt gtttgac                               37

<210> SEQ ID NO 113
<211> LENGTH: 32
<212> TYPE: DNA
<213> ORGANISM: Diabrotica virgifera

<400> SEQUENCE: 113
ctagtgactt caacccaatc aacatcaagt tg                                    32
```

<210> SEQ ID NO 114
<211> LENGTH: 32
<212> TYPE: DNA
<213> ORGANISM: Diabrotica virgifera zeae

<400> SEQUENCE: 114
aattcaactt gatgttgatt gggttgaagt ca                                        32

<210> SEQ ID NO 115
<211> LENGTH: 32
<212> TYPE: DNA
<213> ORGANISM: Diabrotica barberi

<400> SEQUENCE: 115
ctagtcaacc caatcaacat caagttggga tg                                        32

<210> SEQ ID NO 116
<211> LENGTH: 32
<212> TYPE: DNA
<213> ORGANISM: Diabrotica undecimpunctata

<400> SEQUENCE: 116
aattcatccc aacttgatgt tgattgggtt ga                                        32

<210> SEQ ID NO 117
<211> LENGTH: 32
<212> TYPE: DNA
<213> ORGANISM: Diabrotica virgifera

<400> SEQUENCE: 117
ctagtcaatc aacatcaagt tgggatctca cg                                        32

<210> SEQ ID NO 118
<211> LENGTH: 32
<212> TYPE: DNA
<213> ORGANISM: Diabrotica virgifera zeae

<400> SEQUENCE: 118
aattcgtgag atcccaactt gatgttgatt ga                                        32

<210> SEQ ID NO 119
<211> LENGTH: 32
<212> TYPE: DNA
<213> ORGANISM: Diabrotica barberi

<400> SEQUENCE: 119
ctagtaacat caagttggga tctcacttaa cg                                        32

<210> SEQ ID NO 120
<211> LENGTH: 32
<212> TYPE: DNA
<213> ORGANISM: Diabrotica undecimpunctata

<400> SEQUENCE: 120
aattcgttaa gtgagatccc aacttgatgt ta                                        32

<210> SEQ ID NO 121
<211> LENGTH: 32
<212> TYPE: DNA
<213> ORGANISM: Diabrotica virgifera

<400> SEQUENCE: 121

```
ctagtcaagt tgggatctca cttaactgga gg                                      32

<210> SEQ ID NO 122
<211> LENGTH: 32
<212> TYPE: DNA
<213> ORGANISM: Diabrotica barberi

<400> SEQUENCE: 122
aattcctcca gttaagtgag atcccaactt ga                                      32

<210> SEQ ID NO 123
<211> LENGTH: 32
<212> TYPE: DNA
<213> ORGANISM: Diabrotica undecimpunctata

<400> SEQUENCE: 123
ctagttggga tctcacttaa ctggaggtga tg                                      32

<210> SEQ ID NO 124
<211> LENGTH: 32
<212> TYPE: DNA
<213> ORGANISM: Diabrotica undecimpunctata

<400> SEQUENCE: 124
aattcatcac ctccagttaa gtgagatccc aa                                      32

<210> SEQ ID NO 125
<211> LENGTH: 32
<212> TYPE: DNA
<213> ORGANISM: Diabrotica virgifera

<400> SEQUENCE: 125
ctagttctca cttaactgga ggtgatatat ag                                      32

<210> SEQ ID NO 126
<211> LENGTH: 32
<212> TYPE: DNA
<213> ORGANISM: Diabrotica barberi

<400> SEQUENCE: 126
aattctatat atcacctcca gttaagtgag aa                                      32

<210> SEQ ID NO 127
<211> LENGTH: 32
<212> TYPE: DNA
<213> ORGANISM: Diabrotica undecimpunctata

<400> SEQUENCE: 127
ctagtcttaa ctggaggtga tatatatggt cg                                      32

<210> SEQ ID NO 128
<211> LENGTH: 32
<212> TYPE: DNA
<213> ORGANISM: Diabrotica virgifera

<400> SEQUENCE: 128
aattcgacca tatatatcac ctccagttaa ga                                      32

<210> SEQ ID NO 129
<211> LENGTH: 32
<212> TYPE: DNA
<213> ORGANISM: Diabrotica barberi

<400> SEQUENCE: 129
```
ctagtctgga ggtgatatat atggtctagt tg                              32

<210> SEQ ID NO 130
<211> LENGTH: 32
<212> TYPE: DNA
<213> ORGANISM: Diabrotica undecimpunctata

<400> SEQUENCE: 130
aattcaacta gaccatatat atcacctcca ga                              32

<210> SEQ ID NO 131
<211> LENGTH: 32
<212> TYPE: DNA
<213> ORGANISM: Diabrotica virgifera

<400> SEQUENCE: 131
ctagtggtga tatatatggt ctagttcatg ag                              32

<210> SEQ ID NO 132
<211> LENGTH: 32
<212> TYPE: DNA
<213> ORGANISM: Diabrotica balteata

<400> SEQUENCE: 132
aattctcatg aactagacca tatatatcac ca                              32

<210> SEQ ID NO 133
<211> LENGTH: 32
<212> TYPE: DNA
<213> ORGANISM: Diabrotica virgifera zeae

<400> SEQUENCE: 133
ctagttatat atggtctagt tcatgaaaac ag                              32

<210> SEQ ID NO 134
<211> LENGTH: 32
<212> TYPE: DNA
<213> ORGANISM: Diabrotica balteata

<400> SEQUENCE: 134
aattctgttt tcatgaacta gaccatatat aa                              32

<210> SEQ ID NO 135
<211> LENGTH: 32
<212> TYPE: DNA
<213> ORGANISM: Hippodamia convergens

<400> SEQUENCE: 135
ctagtatggt ctagttcatg aaaacaccct tg                              32

<210> SEQ ID NO 136
<211> LENGTH: 50
<212> TYPE: DNA
<213> ORGANISM: Pan troglodytes

<400> SEQUENCE: 136
taccattgag ttccagagag aagccctgga gaactcacac accaacactg           50

<210> SEQ ID NO 137
<211> LENGTH: 50
<212> TYPE: DNA
<213> ORGANISM: Pan troglodytes

<400> SEQUENCE: 137
aaccatcgag ttccagcggg aggccctgga gaatgccaac accaacaccg          50

<210> SEQ ID NO 138
<211> LENGTH: 50
<212> TYPE: DNA
<213> ORGANISM: Canis familiaris

<400> SEQUENCE: 138
caccctggag tttcagcgtg aggccattga gaatgccacc accaatgcag          50

<210> SEQ ID NO 139
<211> LENGTH: 50
<212> TYPE: DNA
<213> ORGANISM: Canis familiaris

<400> SEQUENCE: 139
aaccatcgag tttcagcggg aagccctgga gaatgccaat accaacaccg          50

<210> SEQ ID NO 140
<211> LENGTH: 50
<212> TYPE: DNA
<213> ORGANISM: Gallus gallus

<400> SEQUENCE: 140
cacaatcgaa tttcagaggg aagccttgga gaatgccaac accaacactg          50

<210> SEQ ID NO 141
<211> LENGTH: 50
<212> TYPE: DNA
<213> ORGANISM: Xenopus laevis

<400> SEQUENCE: 141
aaccatcgaa ttccagaggg aagcccttga aaatgccaac acaaatactg          50

<210> SEQ ID NO 142
<211> LENGTH: 50
<212> TYPE: DNA
<213> ORGANISM: Danio rerio

<400> SEQUENCE: 142
caccattgag ttccagagag aagcattaga aaatgccaat acaaacacag          50

<210> SEQ ID NO 143
<211> LENGTH: 51
<212> TYPE: DNA
<213> ORGANISM: Fugu rubripes

<400> SEQUENCE: 143
gaccatcgag ttccagagag aagctttaga gaacgccaac accagcactg a        51

<210> SEQ ID NO 144
<211> LENGTH: 50
<212> TYPE: DNA
<213> ORGANISM: Amphioxus floridae

<400> SEQUENCE: 144
caccatcgag ttccagaggg aagcactgga gaatgccaac accaacacag          50

<210> SEQ ID NO 145
<211> LENGTH: 50
<212> TYPE: DNA
<213> ORGANISM: Ciona savignyi -continued

<400> SEQUENCE: 145
cactgttgag ttccaactgg aagctttaca aaatgcgcaa tcaaataaac          50

<210> SEQ ID NO 146
<211> LENGTH: 50
<212> TYPE: DNA
<213> ORGANISM: Strongylocentrotus purpuratus

<400> SEQUENCE: 146
tacgatagaa gcacagaggg aggcgctgga gaatgctaat accaatgcag          50

<210> SEQ ID NO 147
<211> LENGTH: 50
<212> TYPE: DNA
<213> ORGANISM: Daphnia magna

<400> SEQUENCE: 147
aactattgaa atgcaaagag aagctttgga gggagcaaat accaatacag          50

<210> SEQ ID NO 148
<211> LENGTH: 50
<212> TYPE: DNA
<213> ORGANISM: Bombyx mon

<400> SEQUENCE: 148
tcagattgag gcccaaaggg aagcgctaga aggtgccaat accaatgccc          50

<210> SEQ ID NO 149
<211> LENGTH: 50
<212> TYPE: DNA
<213> ORGANISM: Acyrthosiphon pisum

<400> SEQUENCE: 149
aactattgaa caacagcgag aggcattaga aggtgctaac acaaatacag          50

<210> SEQ ID NO 150
<211> LENGTH: 50
<212> TYPE: DNA
<213> ORGANISM: Apis mellifera

<400> SEQUENCE: 150
tacaattgaa agtcaaaggg aagcacttga atgtgcgaat actaatactg          50

<210> SEQ ID NO 151
<211> LENGTH: 50
<212> TYPE: DNA
<213> ORGANISM: Locusta migratoria

<400> SEQUENCE: 151
aacaatggag atgcaacgag aagctcttga aggagcaaat accaatactg          50

<210> SEQ ID NO 152
<211> LENGTH: 50
<212> TYPE: DNA
<213> ORGANISM: Anopheles gambiae

<400> SEQUENCE: 152
gacgattgaa atgcagcgag aggcgctgga gaatgcgaac acaaacgccg          50

<210> SEQ ID NO 153
<211> LENGTH: 50
<212> TYPE: DNA

<213> ORGANISM: Glossina morsitans

<400> SEQUENCE: 153
aacaattgaa atgcaacgag aagcattgga aagtgctaac acgaataccg          50

<210> SEQ ID NO 154
<211> LENGTH: 50
<212> TYPE: DNA
<213> ORGANISM: Drosophila melanogaster

<400> SEQUENCE: 154
cacaatcgaa atgcagcgcg aggctctgga gagcgccaac acaaacactg          50

<210> SEQ ID NO 155
<211> LENGTH: 50
<212> TYPE: DNA
<213> ORGANISM: Artificial sequence
<220> FEATURE:
<223> OTHER INFORMATION: Artificial oligonucleotide

<400> SEQUENCE: 155
gacgattgaa atgcagagag aagtcttgga atcacccaat actagttcca          50

<210> SEQ ID NO 156
<211> LENGTH: 50
<212> TYPE: DNA
<213> ORGANISM: Tribolium castaneum

<400> SEQUENCE: 156
caccatcgag atgcagcggg aggccctcga gggggccaac accaacacag          50

<210> SEQ ID NO 157
<211> LENGTH: 50
<212> TYPE: DNA
<213> ORGANISM: Diabrotica balteata

<400> SEQUENCE: 157
aactattgaa atgcagaggg aagccctcga aggagctagc acaaatactg          50

<210> SEQ ID NO 158
<211> LENGTH: 50
<212> TYPE: DNA
<213> ORGANISM: Diabrotica undecimpunctata

<400> SEQUENCE: 158
aactattgaa atgcagaggg aagccctcga aggagctagc acaaatactg          50

<210> SEQ ID NO 159
<211> LENGTH: 50
<212> TYPE: DNA
<213> ORGANISM: Diabrotica barberi

<400> SEQUENCE: 159
aactattgaa atgcagaggg aagccctcga aggagctagc acaaatactg          50

<210> SEQ ID NO 160
<211> LENGTH: 50
<212> TYPE: DNA
<213> ORGANISM: Diabrotica virgifera zeae mexican

<400> SEQUENCE: 160
aactattgaa atgcagaggg aagccctcga aggagctagc acaaatactg          50

```
<210> SEQ ID NO 161
<211> LENGTH: 50
<212> TYPE: DNA
<213> ORGANISM: Diabrotica virgifera virgifera

<400> SEQUENCE: 161
aactattgaa atgcagaggg aagccctcga aggagctagc acaaatactg            50

<210> SEQ ID NO 162
<211> LENGTH: 300
<212> TYPE: DNA
<213> ORGANISM: Diabrotica virgifera virgifera

<400> SEQUENCE: 162
gtcgagaaca ttttaaaatt tttggataag tactacgttc ccagcaaaat agctaaagga   60
aatggccaaa twaaaacatg ctctcatcac gactatccta ctagtggaga agtatgcgaa  120
gtcgatgtca gagattggga agaatgcaac agggatcaat tctttaatta tcacaagaat  180
tctccatgta tttttattaa attgaacaaa atatataact gggagccaat rtattacgat  240
gatccmtacg atttacctga ggaaatgccg gataatctga agcaacatat aaggggtatc  300

<210> SEQ ID NO 163
<211> LENGTH: 300
<212> TYPE: DNA
<213> ORGANISM: Diabrotica virgifera zeae

<400> SEQUENCE: 163
gtcgagaaca ttttaaaatt tttggataag tactacgttc ccagcaaaat agctaaagga   60
aatggccaaa taaaaacatg ctctcatcac gactatccta ctagtggaga agtatgcgaa  120
gtcgatgtca gagattggga agaatgcaac agggatcaat tctttaatta tcacaagaat  180
tctccatgta tttttattaa attgaacaaa atatataact gggagccaat atattacgat  240
gatccctacg atttacctga ggaaatgccg gataatctga agcaacatat aaggggtatc  300

<210> SEQ ID NO 164
<211> LENGTH: 300
<212> TYPE: DNA
<213> ORGANISM: Diabrotica barberi

<400> SEQUENCE: 164
gtcgagaaca ttttgaaatt tttrgataag tactacgttc ccagcaaaat agctaaagga   60
aatggccaaa taaaaacatg ctctcatcac gactatccta ctagtggaga agtatgcgaa  120
gtcgatgtca gagattggga agaatgcaac agggatcaat tctttaatta tcacaagaat  180
tctccatgta tttttattaa attgaacaaa atatatgact gggagccaga atattacgat  240
gatccctaca atttacctga ggaaatgccg gataatctga agcaacatat aagaagtatc  300

<210> SEQ ID NO 165
<211> LENGTH: 300
<212> TYPE: DNA
<213> ORGANISM: Diabrotica undecimpunctata howardii

<400> SEQUENCE: 165
gtagagaaca ttttgaaatt tttggataag tactatgttc ccagcaaaat agctaaagga   60
aatagccaaa taaaaacatg ctctcatcac gactatccta ccagtggaga agtatgcgaa  120
gttgatgtta gagattggga agaatgcaat agggatcagt tctttaatta tcacaagaat  180
tctccatgta tctttattaa attgaacaaa atatatgact gggaaccaat gtattacgat  240
```

```
-continued gatccctatg atttacccga ggaaatgcct gatactctga agcaacatat aaggagtatc         300

<210> SEQ ID NO 166
<211> LENGTH: 300
<212> TYPE: DNA
<213> ORGANISM: Diabrotica spp

<400> SEQUENCE: 166
gtagagaaca ttttgaaatt tttggataag tactacgttc ccagcaaaat agctaaagga          60
aatggtcaaa taaaaacatg ctctcatcac gactatccta ccagtggaga agtatgcgaa         120
gttgatgtta gagattggga ggaatgcaat agggatcagt tctttaatta tcacaagaat         180
tctccatgta tttttattaa attgaacaaa atatatgact gggaaccatt atattacgac         240
gatccctata atttacccga ggaaatgcct gattctctga agcaacatat aagaagtatc         300

<210> SEQ ID NO 167
<211> LENGTH: 21
<212> TYPE: DNA
<213> ORGANISM: Artificial sequence
<220> FEATURE:
<223> OTHER INFORMATION: Synthetic primer

<400> SEQUENCE: 167
aacctgtaca tgcagagttt c                                                   21
```

SELECTING AND STABILIZING DSRNA CONSTRUCTS

This application is a divisional of U.S. application Ser. No. 11/674,005 filed Feb. 12, 2007, now abandoned, which claims benefit of U.S. Provisional Application No. 60/772,736, filed Feb. 13, 2006, each of the entire contents of which are incorporated by reference herein.

INCORPORATION OF SEQUENCE LISTING

The Sequence listing contained in the file named MONS092USD1_ST25.txt, which is 72.6 kilobytes (size as measured in Microsoft Windows®) and created on Jun. 9, 2014, is incorporated herein by reference.

BACKGROUND OF THE INVENTION

1. Field of the Invention

The present invention relates to stable expression of RNAi constructs in plants to enable genetic control of plant pathogens and pests. The invention provides methods and compositions for improving the efficacy of dsRNAs derived from such constructs.

2. Description of Related Art

Short strands of complementary double stranded RNA (dsRNA) when present in, or introduced into, living cells may specifically affect the expression of a "target" gene when regions of nucleotide sequence similarity are shared between the dsRNA and the target gene transcript. Such RNA molecules may comprise complementary sequences separated by a "spacer" region such that double stranded regions of RNA are formed. The dsRNA may be cleaved by enzymes known as dimeric RNase III ribonucleases (also called "dicer" enzymes) into segments approximately 21-25 base pairs in length; called siRNAs ("short interfering RNAs" or "small interfering RNAs"). The siRNA causes specific RNAse activity in a RNA-induced silencing complex ("RISC") to hydrolyze the target gene mRNA, thereby post-transcriptionally suppressing expression of the target gene. Only transcripts complementary to the siRNA are cleaved and degraded, and thus the effect, sometimes called RNA interference (RNAi), is gene specific. RNAi has been used to specifically disrupt gene expression in a number of organisms including *Caenorhabditis elegans* (Fire et al., 1998), *Drosophila melanogaster*, insects including Coleoptera (Bucher et al., 2002) and Lepidoptera (Uhlirova et al. 2003; Bettencourt et al., 2002), fungi (Cogoni et al. 2000), and plants such as *Arabidopsis thaliana*, among others. dsRNA present in plants may also guide DNA methylation of targeted chromatin regions, resulting in gene silencing (e.g. Wassenegger et al., 1994; Carthew, 2001; Zilberman et al., 2004).

Effective use of RNAi leads to suppression of expression of a specific target gene, and thus stable expression of RNAi constructs in transgenic crops can allow for novel genetic approaches to pest control. However dsRNA produced from a transgene in planta, although targeted to another organism, may evoke in planta responses such as cleavage ("dicing") of a transgene transcript, as well as silencing of the cognate transgene in the transgenic host plant. These responses could reduce or eliminate dsRNA production and hence efficacy against a target organism.

There have been reports concerning design of constructs for evoking dsRNA-mediated suppression of gene expression (Wesley et al., 2001; Yuan et al., 2004; Reynolds et al., 2004; Arziman et al., 2005). Mechanisms for systemic transport of sRNA ("small RNA") molecules (including dsRNA) are known in some organisms (e.g. Voinnet 2005), and the sequence of the ribonucleotide being transported is known to have an effect on the efficiency of its uptake (Winston et al., 2002). For instance, *C. elegans* requires a dsRNA of roughly 100 base pairs (bp) in length to be productively taken up into gut cells e.g. via SID1 protein (Feinberg and Hunter, 2003), and WO9953050 describes dsRNA constructs comprising intron sequences in spacer regions. However the parameters leading to optimized production, stabilization, and uptake of dsRNA active against a target pest, while ensuring stable expression of a transgene encoding such dsRNA, and avoiding transgene silencing in a host cell, are not well understood. Thus there exists a need to ensure stable transcription of specific effective dsRNA-encoding transgenes within plants, and subsequent transport and uptake of the resulting dsRNA, to yield effective and specific gene suppression in target plant pathogen and pest species.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 1A-1B: Alignment of a 100 bp segment of the Dv49 target with related sequences from other organisms representing multiple genera, orders and phyla, specifically, *Pan troglodytes* (Pt49_1) (SEQ ID NO:136); *Pan troglodytes* (Pt49_2) (SEQ ID NO:137); *Canis familiaris* (Cf49_1) (SEQ ID NO:138); *Canis familiaris* (Cf49_2) (SEQ ID NO:139); *Gallus gallus* (Gg49) (SEQ ID NO:140); *Xenopus laevis* (Xl49) (SEQ ID NO:141); *Danio rerio* (Dr49) (SEQ ID NO:142); *Fugu rubripes* (Fr49) (SEQ ID NO:143); *Amphioxus floridae* (Af49) (SEQ ID NO:144); *Ciona savignyi* (Cs49) (SEQ ID NO:145); *Strongylocentrotus purpuratus* (Sp49) (SEQ ID NO:146); *Daphnia magna* (Dmag49) (SEQ ID NO:147); *Bombyx mori* (Bm49) (SEQ ID NO:148); *Acyrthosiphon pisum* (Ap49) (SEQ ID NO:149); *Apis mellifera* (Am49) (SEQ ID NO:150); *Locusta migratoria* (Lm49) (SEQ ID NO:151); *Anopheles gambiae* (Ag49) (SEQ ID NO:152); *Glossina morsitans* (Gm49) (SEQ ID NO:153); *Drosophila melanogaster* (Dm49) (SEQ ID NO:154); (Lh49) (SEQ ID NO:155); *Tribolium castaneum* (Tc49) (SEQ ID NO:156); *Diabrotica balteata* (Dba149) (SEQ ID NO:157); *Diabrotica undecimpunctata* (Du49) (SEQ ID NO:158); *Diabrotica barberi* (Db49) (SEQ ID NO:159); *Diabrotica virgifera zeae mexican* (Dz49) (SEQ ID NO:160); and *Diabrotica virgifera virgifera* (Dv49) (SEQ ID NO:161). Sequences differing from *Diabrotica virgifera virgifera* (Dv49) are highlighted. Amino acid alignment (a.a.) for the Dv49 conceptual translation is shown below the nucleotide sequence. Reynolds scores were calculated for the Dv49 sequence and are shown below the amino acid alignment—the score position corresponds to nucleotide 19 of the antisense strand 21mer. Data from the embedded 26mer efficacy scan are presented below the Reynolds score. The potential 21mers that could be produced from each scan segment are underlined and the WCR mortality resulting from each embedded segment fed at 0.2 ppm in artificial diet bio-assay is shown below each scan segment. * significantly different from untreated control, P value <0.05, Planned Contrasts.

FIG. 2: Segments of coding sequence from a Na/K-exchanging ATPase (putative Drosophila gene, CG9261, ortholog) aligned from multiple *Diabrotica* spp., namely *Diabrotica virgifera virgifera* (Western Corn Rootworm, WCR) (SEQ ID NO:162); *Diabrotica virgifera* zeae (Mexican Corn Rootworm, MCR) (SEQ ID NO163); *Diabrotica barberi* (Northern Corn Rootworm, NCR) (SEQ ID NO:164); *Diabrotica undecimpunctata howardii* (Southern Corn Rootworm, SCR) (SEQ ID NO:165); and *Diabrotica* spp (BCB) (SEQ ID NO:166). Sequence conforming to the group consensus is boxed and shaded. Sequencing has shown presence of alleles in some instances (e.g. "R" at position 49 of NCR sequence).

Figure 3:
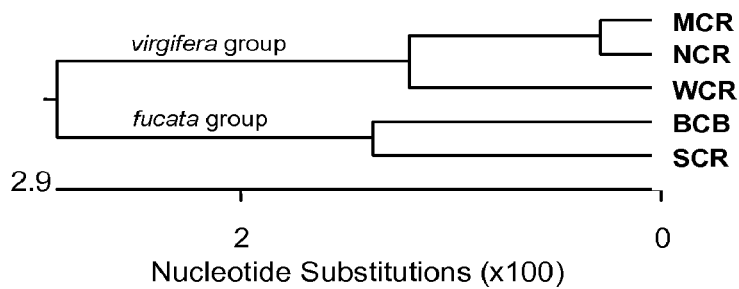
FIG. 3: Phylogenetic tree determined using a 559 bp segment of Dv26 and the ClustalW algorithm in the DNAS-TAR software package (Madison, Wis.).

In still yet another aspect, the invention provides a method for protecting a plant from pest infestation comprising expressing a dsRNA molecules obtained according to the invention in a transgenic plant, providing said plant or a part or tissue thereof to one or more pests comprising said nucleotide sequence, and observing a phenotypic effect in the organism, wherein the phenotypic effect is sufficient to inhibit infestation of the transgenic plant by the pest. The invention also provides a plant protected from pest infestation according to any of the methods described herein, as well as a plant regenerated from such a cell, and also a seed or progeny produced from such a plant, wherein said seed or progeny comprises a nucleotide sequence obtained according to the invention.

In still yet another aspect, the invention provides a method of producing an expression construct for expressing a dsRNA with reduced transgene silencing in a plant cell, comprising: (a) preparing an expression construct comprising a first sequence, a second sequence, and a third polynucleotide sequence, wherein the third polynucleotide sequence is linked to the first polynucleotide sequence by the second polynucleotide sequence and the third polynucleotide sequence is substantially the reverse complement of the first polynucleotide sequence; and (b) introducing an intron into at least one of the first and third polynucleotide sequences or introducing said expression construct into the intron, wherein the first and third polynucleotide sequences hybridize when transcribed into RNA and form a dsRNA molecule stabilized by the second polynucleotide sequence after intron splicing, and wherein the expression construct exhibits reduced transgene silencing in a plant cell transformed with the expression construct relative to an expression construct that lacks the intron. In one embodiment, the intron is introduced into at least one of the first and third polynucleotide sequences. In another embodiment, the intron is introduced into the first and third polynucleotide sequences. In further embodiments, the expression construct is introduced into the intron.

In still yet another aspect, the invention provides a method of controlling feeding by a target crop pest or pathogen or progeny thereof on a plant comprising introducing into the plant an expression construct prepared by any of the methods disclosed herein. The construct may be introduced, for example, by direct genetic transformation or by transformation of a parent plant and/or progenitor cell. The invention further provides an expression construct prepared according to any of the methods disclosed herein. Still further provided are transgenic plants and plant cell transformed with an expression construct disclosed herein.

In still yet another aspect, the invention provides a method of increasing the pest or pathogen-inhibitory activity of a dsRNA, comprising: (a) obtaining a first nucleic acid segment that when expressed as a dsRNA and taken up by a target crop pest or pathogen inhibits feeding by the target crop pest or pathogen or progeny thereof; and (b) linking the first nucleic acid segment to a second nucleic acid segment to create a longer nucleic acid segment, wherein the second nucleic acid segment is a nucleic acid that does not inhibit feeding by the target crop pest or pathogen or progeny thereof when expressed as a dsRNA, and wherein a dsRNA expressed from the longer nucleic acid segment exhibits increased potency of inhibition of feeding by the target crop pest or pathogen or progeny thereof relative to the dsRNA expressed from the first nucleic acid segment alone. In one embodiment, the first nucleic acid segment is obtained by a method comprising the steps of: I) obtaining a starting nucleic acid molecule that when expressed as a dsRNA and taken up by a target crop pest or pathogen inhibits feeding by the target crop pest or pathogen or progeny thereof; II) selecting at least a first portion of the starting nucleic acid molecule that inhibits feeding by a target crop pest or pathogen or a progeny thereof following uptake of a dsRNA expressed from said portion; and III) employing the portion as said the first nucleic acid segment in step a). The starting nucleic acid molecule may be a cDNA. In one embodiment, step II) comprises preparing a series of overlapping or consecutive portions from the starting nucleic acid molecule and identifying from said portions at least a first portion that inhibits feeding by a target crop pest or pathogen or a progeny thereof when expressed as a dsRNA and taken up by the target crop pest or pathogen.

The method of increasing the pest or pathogen-inhibitory activity of a dsRNA may further comprise in particular embodiments producing a recombinant vector comprising a first, a second and a third polynucleotide sequence, wherein the first polynucleotide sequence comprises the longer nucleotide segment and wherein the third polynucleotide sequence is linked to the first polynucleotide sequence by the second polynucleotide sequence, and wherein the third polynucleotide sequence is substantially the reverse complement of the first polynucleotide sequence such that the first and the third polynucleotide sequences hybridize when transcribed into a ribonucleic acid to form the double stranded ribonucleotide molecule stabilized by the linked second ribonucleotide sequence. In specific embodiments the second nucleotide segment is not substantially complementary to a nucleotide sequence of the target crop pest or pathogen. In further embodiments, one or both of the first nucleic acid segment and the third nucleic acid segment comprises an intron. The method may also comprise introducing an intron into said first nucleic acid segment. In further embodiments, the first nucleic acid segment may comprise about 19 to about 80, about 19 to about 50 and about 21 to about 30 contiguous bases substantially complementary to a coding sequence of the target crop pest or pathogen. The longer nucleic acid segment may comprise at least about 80 bases, including at least about 100 bases and from about 80 bp to about 250 bases. In one embodiment, the target crop pest or pathogen is an insect and may be a Coleopteran, Lepidopteran, Homopteran, or Hemipteran, e.g. a *Diabrotica* spp. In other embodiments the target crop pest or pathogen is a nematode.

In another aspect, the invention further provides a method for producing an expression construct for expressing a dsRNA with increased specificity of pest or pathogen-inhibitory activity comprising: (a) obtaining a starting nucleic acid molecule substantially complementary to at least a first coding sequence of a target crop pest or pathogen; (b) selecting a region within the starting molecule that when expressed as a dsRNA inhibits feeding by the target crop pest or pathogen or progeny thereof following uptake of the dsRNA expressed from the region by the target crop pest or pathogen; (c) linking the region to a second nucleic acid molecule to produce an expression construct, wherein the second nucleic acid molecule when expressed as a dsRNA does not inhibit feeding by a target crop pest or pathogen or progeny thereof following uptake of the dsRNA. The starting nucleic acid molecule utilized by the method may be a cDNA from the target crop pest or pathogen, such as an insect or nematode. In particular embodiments, the insect may be a Coleopteran, Lepidopteran, Homopteran, or Hemipteran insect, including an insect selected from the group consisting of: *D. virgifera virgifera; D. virgifera* zeae; *D. undecimpunctata; D. balteata; D. barberi*; and *D. speciosa*. In further embodiments, the first nucleic acid segment may comprise about 19 to about 80, about 19 to about 50 and about 21 to about 30 contiguous bases substantially complementary to a coding sequence of the target crop pest or pathogen. The longer nucleic acid segment may comprise at least about 80 bases, including at least about 100 bases and from about 80 bp to about 250 bases.

A further aspect of the invention provides a method comprising identifying at least a second region within the starting molecule that when expressed as a dsRNA inhibits feeding by the target crop pest or pathogen or progeny thereof, and linking the second region to the second nucleic acid molecule or a third nucleic acid molecule that when expressed as a dsRNA does not inhibit feeding by a target crop pest or pathogen or progeny thereof following uptake of the dsRNA expressed from the third nucleic acid molecule by the target plant pest or pathogen. In some embodiments, the region is not substantially complementary to a nucleic acid of a non-target crop pest or pathogen. In other embodiments, the region is complementary to a nucleic acid unique to the species in which the target crop pest or pathogen is classified. In yet other embodiments, the region is complementary to a nucleic acid unique to the genus in which the target crop pest or pathogen is classified. In still further embodiments, the region is unique to *Diabrotica* spp., including those selected from the group consisting of *Diabrotica undecimpunctata howardii* (Southern Corn Rootworm (SCR)), *Diabrotica virgifera virgifera* (Western Corn Rootworm (WCR)), *Diabrotica barberi* (Northern Corn Rootworm (NCR)), *Diabrotica virgifera zeae* (Mexican Corn Rootworm (MCR)), *Diabrotica balteata, Diabrotica viridula*, and *Diabrotica speciosa* (Brazilian Corn Rootworm (BZR)).

In another aspect, the invention provides a method of controlling feeding by a target crop plant pest or pathogen or progeny thereof on a plant comprising introducing into the plant an expression construct or dsRNA prepared by the foregoing method. The invention also provides a plant cell transformed with an expression construct prepared by the foregoing method.

In yet another aspect, the invention provides a method of enhancing the control of a target crop pest or pathogen in a plant comprising expressing in the cells of the plant at least two dsRNA sequences that function upon uptake by the pest or pathogen to inhibit the expression of at least a first target coding sequence within the target crop pest or pathogen, wherein the two dsRNA sequences are substantially complementary to two non-contiguous portions of the first target coding sequence or to two different coding sequences of the target crop pest or pathogen. In further embodiments, the invention provides a method wherein the two dsRNA sequences comprises about 19 bp to about 80 bp, or about 19 bp to about 50 bp, or about 21 bp to about 30 bp in length. In another embodiment, the two dsRNA sequences are substantially complementary to at least two target coding sequences of the target crop pest or pathogen. The method may further comprise expressing in the cells of the plant at least a third dsRNA sequence that functions upon uptake by the pest or pathogen to inhibit the expression of a third target coding sequence within the target crop pest or pathogen, wherein the third dsRNA sequence is substantially complementary to a portion of the third target coding sequence. In yet another embodiment, a method is provided wherein the two dsRNA sequences are expressed from regions selected from a starting nucleic acid molecule that when expressed as a dsRNA inhibits feeding by a target crop pest or pathogen or progeny thereof following uptake of the dsRNA by the target crop pest or pathogen. The starting nucleic acid molecule may further be a cDNA from the target crop pest or pathogen.

In another embodiment, the provided method further comprises expressing a polynucleotide sequence in the cell selected from the group consisting of a patatin, a *Bacillus thuringiensis* insecticidal protein, a *Xenorhabdus* insecticidal protein, a *Photorhabdus* insecticidal protein, a *Bacillus laterosporus* insecticidal protein, and a *Bacillus sphaericus* insecticidal protein. In further embodiments, exemplary polynucleotides may encode a *Bacillus thuringiensis* insecticidal protein selected from the group consisting of a Cry1, a Cry2, a Cry3, or a coleopteran toxic protein selected from the group consisting of a TIC851, a CryET70, ET29, a binary insecticidal protein CryET33 and CryET34, a binary insecticidal protein CryET80 and CryET76, a binary insecticidal protein ET29 and TIC810, a binary insecticidal protein TIC100 and TIC101, and a binary insecticidal protein PS149B1, or other coleopteran toxic protein (e.g. deMaagd et al., 2003). Other insecticidal compositions directed to controlling additional plant pests are possible, for example, as set forth in the full toxin listing at the following website: lifesci.sussex.ac.uk/home/Neil_Crickmore/Bt/index.html, and also including one or more VIP toxin(s) as set forth therein. Thus, in certain embodiments, combinations of control agent(s) include one or more polynucleotides of the present invention that express a dsRNA and at least one other agent toxic to a plant pest such as an insect or a nematode.

The invention further provides a method wherein the target coding sequence encodes a protein, the predicted function of which is selected from the group consisting of muscle formation, juvenile hormone formation, juvenile hormone regulation, ion regulation and transport, digestive enzyme synthesis, maintenance of cell membrane potential, feeding site formation, feeding site development, feeding site maintenance, infection, molting, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis. In another embodiment, the invention provides a method wherein two coding sequences are targeted. The two target coding sequences may perform at least two functions essential for target crop pest or pathogen survival that are suppressed by the dsRNA sequences, the functions being selected from the group consisting of feeding by the pest or pathogen, cell apoptosis, cell differentiation and development, capacity or desire for sexual reproduction, muscle formation, muscle twitching, muscle contraction, juvenile hormone formation, juvenile hormone regulation, ion regulation and transport, maintenance of cell membrane potential, amino acid biosynthesis, amino acid degradation, sperm formation, pheromone synthesis, pheromone sensing, antennae formation, wing formation, leg formation, egg formation, larval maturation, digestive enzyme formation, haemolymph synthesis, haemolymph maintenance, neurotransmission, larval stage transition, pupation, emergence from pupation, cell division, energy metabolism, respiration, and formation of cytoskeletal structure.

The invention further provides a method of resistance management, comprising contacting a target organism with at least a first nucleic acid segment of the present invention, and one or more agent(s) selected from the group consisting of: a patatin, a *Bacillus thuringiensis* insecticidal protein, a *Xenorhabdus* insecticidal protein, a *Photorhabdus* insecticidal protein, a *Bacillus laterosporus* insecticidal protein, a *Bacillus sphaericus* insecticidal protein, or other insecticidal Bt toxin as set forth at the website: lifesci.sussex.ac.uk/home/Neil_Crickmore/Bt/index.html., a biocontrol agent, and an insecticide.

DETAILED DESCRIPTION OF THE INVENTION

Described herein are methods and compositions for improving efficacy and expression of dsRNA molecules that modulate gene expression in plant pests and pathogens. The methods enhance the specificity of small interfering RNA (siRNA) or related segments produced from plant transgenes that encode dsRNA, and that provide dsRNA-mediated suppression of target gene expression in plant pests and plant pathogens. The transgene construct and target sequence size is optimized for production and delivery of one or more ribonucleotides effective in the cells of specific target species, while avoiding production of non-specific siRNAs that might otherwise modulate gene expression in an unintended manner. At the same time, by optimizing arrangement of target sequences, the invention reduces the potential for silencing of the transgene in the plant by disrupting continuous target sequence with introns, thereby preventing feedback that would recognize the gene and lead to silencing in the plant.

Sequences that specifically target pest or pathogen species may be engineered into plant expression constructs, such as those with inverted repeats or by use of other methods for eliciting the formation of dsRNA. By cloning siRNAs or by empirical determination via presentation of dsRNA segments to cells or whole pests that scan across a target sequence, 21-24mers that effectively lead to target message degradation can be determined. Using this information novel sequence structure for expression in planta can be created. This sequence structure can be further designed to yield dsRNA molecules, encoding one or more siRNA molecules that are effectively taken up by the target species, while at the same time resulting in formation of siRNAs specific for modulating expression of a specific ortholog, homolog, or allele of a target gene in a target species. Expression of a specific member of a gene family may be suppressed by designing a dsRNA construct that targets that member based on sequence polymorphism between the members of a gene family Thus, specific target sequences (e.g. siRNA-sized, approximately 20-25 base pairs in length) may be included in a dsRNA construct based upon their empirically determined or predicted efficacy toward specific target species, populations, or sub-populations, and less specific or non-specific sequences may be excluded, while still achieving transport of effective transgene-encoded dsRNA into a cell of a target organism. The efficacy of specific siRNA-sized ribonucleotide sequences can be determined by practical evaluations in bio-assays or through the use of predictive tools (e.g. Reynolds scores; Reynolds et al., 2004) that consider biophysical parameters that are common to effective or ineffective siRNAs.

Understanding specific requirements needed to target pest species with exogenous (e.g. transgenic plant-produced) RNA enhances the ability to produce highly effective and specific transgenic constructs. In western corn rootworm (WCR), it was determined that a 50 bp segment of the WCR V-ATPase subunit A is sufficient to elicit mortality when tandemly duplicated 5 times (250 bp total), but is ineffective as a 50 bp monomer. The 50 bp segment embedded in a neutral carrier sequence to yield a total dsRNA of 100 bp was also effective. Thus there is a size optimum for efficient uptake into organisms susceptible to RNAi. This observation indicates the need to "stabilize" the production of appropriately sized dsRNA for pest control.

Using the carrier concept, one or more siRNA sequence can be embedded for transcription within longer sequences. Such sequences may be used to demonstrate the effectiveness of any candidate siRNA, independent of adjacent naturally occurring sequences, allowing for enhanced flexibility in designing transgene constructs that encode dsRNA. Naturally occurring adjacent sequences that demonstrate less efficacy or specificity may be left out of a dsRNA construct, while the construct nevertheless encodes the necessary sequence, and sequence length, to yield efficacious siRNA upon expression within a plant host cell and uptake and processing in a cell of a target organism. This knowledge enables the creation of novel chimeric sequences that incorporate chosen sequences encoding siRNAs into highly effective primary suppression transcripts.

Figure 4:
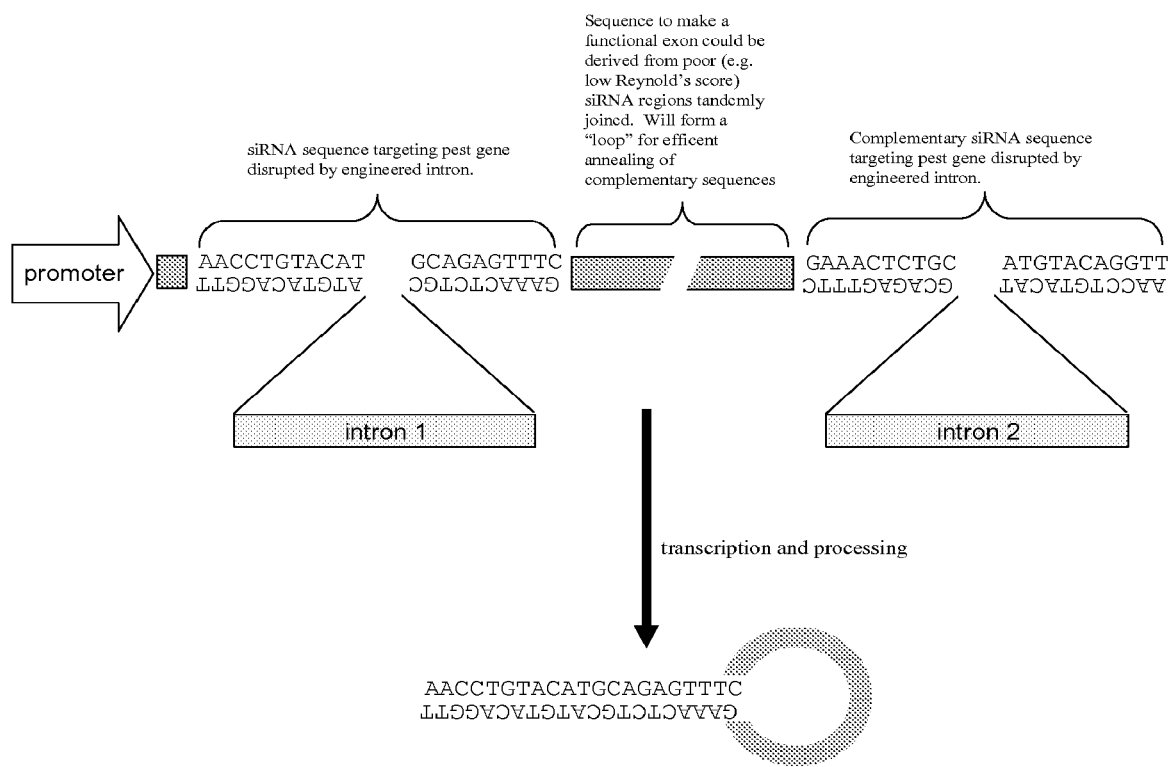
FIG. 4: Design for transgene that reduces direct contiguous sequence identity between transcript of gene and resulting dsRNA transcript. Transcription unit could be terminated by a synthetic sequence derived from siRNAs that are not productively incorporated into RISC. The figure shows the illustrative sequence AACCTGTACATGCAGA nucleotide sequence, and observing a phenotypic effect in said organism, wherein the phenotypic effect is sufficient to inhibit infestation of said transgenic plant by said pest.

A transgene designed by the present methods may also have dsRNA segment(s) encoding siRNA sequences interrupted through intron placement. Inclusion of one or more intron sequences in the target sequence may enhance production and stability of a primary transcript that ultimately yields an effective siRNA, while displaying a reduced propensity to be silenced in the plant cell. Additional sequence such as 5' and 3' untranslated regions (UTRs) and other sequence, for instance to make exons of at least a minimal required size for plant processing, may be produced by combining sequences (e.g. direct tandem sense sequence) that do not elicit effective siRNAs. Additional exon sequences may be created from sequence that does not give rise to productive siRNAs. This arrangement may result in a reduced potential to silence the transgene (e.g. via methylation and eventual transcriptional silencing in a plant host cell) because the gene is distinct in sequence from the processed transcript that generates siRNAs, which might otherwise cause transgene silencing via changes in chromatin structure. The presence of introns in the siRNA regions of the primary transcript may also slow overall processing and improve the longevity or stability of the dsRNA that results (FIG. 4).

Figure 5:
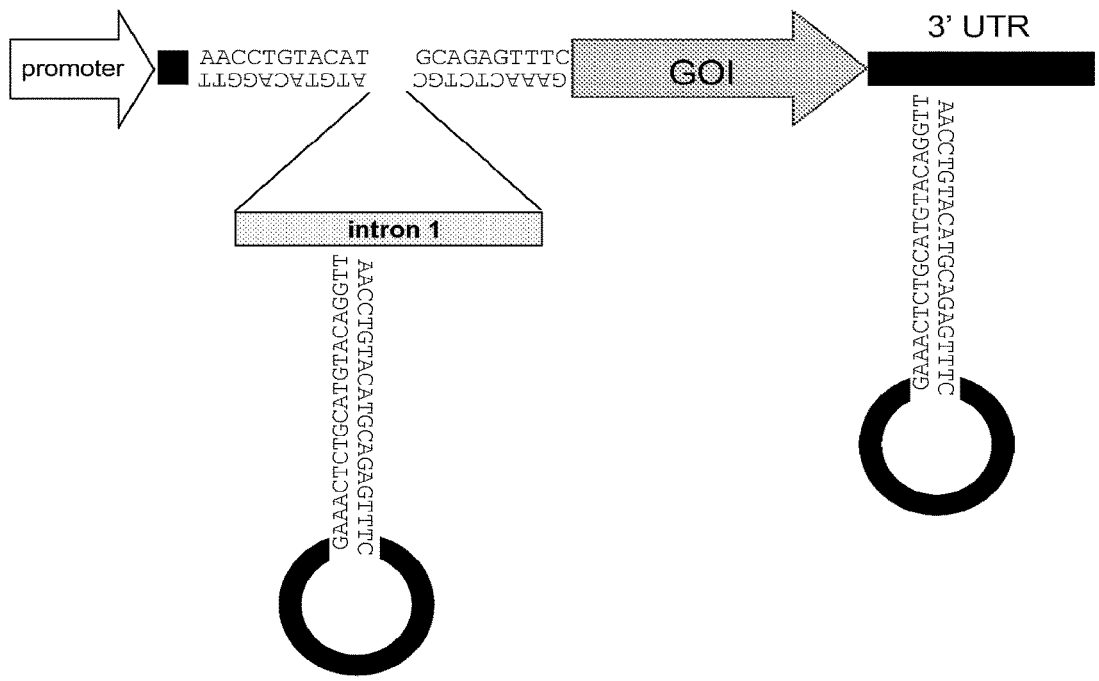

Additional target sequences may be added by extending the primary transcriptional unit with more introns and exons designed as above. Overlapping potent siRNAs and placing the intron within the overlap could expand the number of target sequences while minimizing the number of required introns within the construct (FIG. 5). One or more distinct sequences, each encoding siRNAs targeting expression of one or more target genes and that modulate gene expression in a target organism, may be deployed.

Suppression of expression of two or more target genes allows for provision of multiple modes of action via dsRNA-mediated gene suppression against a target organism. Multiple modes of action may also be achieved in transgenic plants by combining one or more dsRNA-mediated approaches with other means, such as *Bacillus*-derived insecticidal peptides (e.g. crystal proteins), to interfere with the growth and development of target organisms. Combining several or multiple sequences encoding potent siRNAs, possibly in conjunction with other means, also allows development of durable pest resistance management schemes.

A. Nucleic Acid Compositions and Constructs

The invention provides recombinant DNA constructs for use in achieving stable transformation of a host plant cell. Transformed host cells may express effective levels of preferred dsRNA molecules and hence siRNA from the recombinant DNA constructs, to modulate gene expression in target cells. Isolated and purified nucleotide segments may be provided from cDNA and/or genomic libraries. Deduced nucleotide sequence information allows identification of pairs of nucleotide sequences which may be derived from any preferred invertebrate pest, such as an insect, for use as thermal amplification primers to generate the dsRNA and siRNA molecules of the present invention.

As used herein, the term "nucleic acid" refers to a single or double-stranded polymer of deoxyribonucleotide or ribonucleotide bases. The "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), sRNA (small RNA), tRNA (transfer RNA, whether charged or discharged with a corresponding acylated amino acid), and cRNA (complementary RNA) and the term "deoxyribonucleic acid" (DNA) is inclusive of cDNA and genomic DNA and DNA-RNA hybrids. The words "nucleic acid segment", "nucleotide sequence segment", or more generally "segment" will be understood by those in the art as a functional term that includes both genomic sequences, ribosomal RNA sequences, transfer RNA sequences, messenger RNA sequences, operon sequences and smaller engineered nucleotide sequences that express, or may be adapted to express, polynucleotides, proteins, polypeptides or peptides.

Provided according to the invention are nucleotide sequences, the expression of which results in an RNA sequence which is substantially homologous to an RNA molecule of a targeted gene in a target organism, such as a plant pest or pathogen. Thus, after taking up the stabilized RNA sequence, down-regulation of the expression of the nucleotide sequence of the target gene in the cells of the target organism may be obtained, resulting in a deleterious effect on the maintenance, feeding, viability, proliferation, or reproduction of the target organism.

As used herein, the term "substantially homologous" or "substantial homology", with reference to a nucleic acid sequence, includes a nucleotide sequence that hybridizes under stringent conditions to a coding sequence as set forth in the sequence listing, or the complements thereof. Sequences that hybridize under stringent conditions are those that allow an antiparallel alignment to take place between the two sequences, and the two sequences are then able, under stringent conditions, to form hydrogen bonds with corresponding bases on the opposite strand to form a duplex molecule that is sufficiently stable under the stringent conditions to be detectable using methods well known in the art. Substantially homologous sequences have preferably from about 70% to about 80% sequence identity, or more preferably from about 80% to about 85% sequence identity, or most preferable from about 90% to about 95% sequence identity, to about 99% sequence identity, to a nucleotide sequence as set forth in the sequence listing, or the complements thereof.

As used herein, the term "sequence identity", "sequence similarity" or "homology" is used to describe sequence relationships between two or more nucleotide sequences. The percentage of "sequence identity" between two sequences is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

As used herein, a "comparison window" refers to a conceptual segment of at least 6 contiguous positions, usually about 50 to about 100, more usually about 100 to about 150, in which a sequence is compared to a reference sequence of the same number of contiguous positions after the two sequences are optimally aligned. The comparison window may comprise additions or deletions (i.e. gaps) of about 20% or less as compared to the reference sequence (which does not comprise additions or deletions) for optimal alignment of the two sequences Those skilled in the art should refer, for example, to the detailed methods used for sequence alignment in the Wisconsin Genetics Software Package Release 7.0, Genetics Computer Group, 575 Science Drive Madison, Wis., USA).

The present invention provides DNA sequences capable of being expressed as an RNA in a cell or microorganism to inhibit target gene expression in a cell, tissue or organ of a target organism. The sequences may comprise a DNA molecule coding for one or more different nucleotide sequences, wherein each of the different nucleotide sequences comprises a sense nucleotide sequence and an antisense nucleotide sequence. The sequences may be connected by a spacer sequence. The spacer sequence can constitute part of the sense nucleotide sequence or the antisense nucleotide sequence and is found within the dsRNA molecule between the sense and antisense sequences. The sense nucleotide sequence or the antisense nucleotide sequence is substantially identical to the nucleotide sequence of the target gene or a derivative thereof or a complementary sequence thereto. The dsDNA molecule may be placed operably under the control of a promoter sequence that functions in the cell, tissue or organ of the host expressing the dsDNA to produce dsRNA molecules. As used herein, the term "plant expression construct" refers to a recombinant DNA molecule comprising a promoter functional in a plant cell operably linked to a DNA sequence that encodes dsRNA, and a 3' transcription termination polynucleotide molecule.

The invention also provides a DNA sequence for expression in a cell of a plant that, upon expression of the DNA to RNA and being taken up by a target organism, such as a plant pathogen or plant pest, achieves suppression of a target gene in a cell, tissue or organ of a target organism. The dsRNA may comprise one or multiple structural gene sequences, wherein each of the structural gene sequences comprises a sense nucleotide sequence and an antisense nucleotide sequence that may be connected by a spacer sequence that forms a loop within the complementary sense and antisense sequences. An intron sequence with appropriate splice sites may be placed in at least one of the sense and antisense nucleotide sequences. The sense nucleotide sequence or the antisense nucleotide sequence, apart from any intron present, is substantially identical to the nucleotide sequence of the target gene, derivative thereof, or sequence complementary thereto. The one or more structural gene sequences may be placed operably under the control of one or more promoter sequences, at least one of which is operable in the cell, tissue or organ of a host organism for expression of the transcript.

A gene sequence or fragment for control of gene expression in a target organism according to the invention may be cloned between two tissue specific promoters, which are operable in a transgenic plant cell, and therein expressed to produce mRNA in the transgenic plant cell that form dsRNA molecules thereto. The dsRNA molecules contained in plant tissues may be taken up by a target organism so that the intended suppression of the target gene expression is achieved.

A nucleotide sequence provided by the present invention may comprise an inverted repeat separated by a "spacer sequence." The spacer sequence may be a region comprising any sequence of nucleotides that facilitates secondary structure formation between each repeat, where this is required. In one embodiment of the present invention, the spacer sequence is part of the sense or antisense coding sequence for mRNA. The spacer sequence may alternatively comprise any combination of nucleotides or homologues thereof that are capable of being linked covalently to a nucleic acid molecule. The spacer sequence may comprise, for example, a sequence of nucleotides of at least about 10-100 nucleotides in length, or alternatively at least about 100-200 nucleotides in length, at least 200-400 about nucleotides in length, or at least about 400-500 nucleotides in length.

The nucleic acid molecules or fragments of the nucleic acid molecules or other nucleic acid molecules in the sequence listing are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the complement of another nucleic acid molecule if they exhibit complete complementarity. Two molecules are said to be "minimally complementary" if they can hybridize to one another with sufficient stability to permit them to remain annealed to one another under at least conventional "low-stringency" conditions. Similarly, the molecules are said to be complementary if they can hybridize to one another with sufficient stability to permit them to remain annealed to one another under conventional "high-stringency" conditions. Conventional stringency conditions are described by Sambrook, et al., (1989), and by Haymes et al., (1985).

Departures from complete complementarity are therefore permissible, as long as such departures do not completely preclude the capacity of the molecules to form a double-stranded structure. Thus, in order for a nucleic acid molecule or a fragment of the nucleic acid molecule to serve as a primer or probe it needs only be sufficiently complementary in sequence to be able to form a stable double-stranded structure under the particular solvent and salt concentrations employed.

Appropriate stringency conditions which promote DNA hybridization are, for example, 6.0×sodium chloride/sodium citrate (SSC) at about 45° C., followed by a wash of 2.0×SSC at 50° C., are known to those skilled in the art or can be found in Current Protocols in Molecular Biology (1989). For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Preferably, a nucleic acid for use in the present invention will exhibit at least from about 80%, or at least from about 90%, or at least from about 95%, or at least from about 98% or even about 100% sequence identity with one or more nucleic acid molecules as set forth in the sequence listing.

Nucleic acids of the present invention may also be synthesized, either completely or in part, especially where it is desirable to provide plant-preferred sequences, by methods known in the art. Thus, all or a portion of the nucleic acids of the present invention may be synthesized using codons preferred by a selected host. Species-preferred codons may be determined, for example, from the codons used most frequently in the proteins expressed in a particular host species. Other modifications of the nucleotide sequences may result in mutants having slightly altered activity.

dsRNA or siRNA nucleotide sequences comprise double strands of polymerized ribonucleotide and may include modifications to the phosphate-sugar backbone or the nucleoside. Modifications in RNA structure may be tailored to allow specific genetic inhibition. In one embodiment, the dsRNA molecules may be modified through an enzymatic process so that siRNA molecules may be generated. The siRNA can efficiently mediate the down-regulation effect for some target genes in some target organisms. This enzymatic process may be accomplished by utilizing an RNAse III enzyme or a DICER enzyme, present in the cells of an insect, a vertebrate animal, a fungus or a plant in the eukaryotic RNAi pathway (Elbashir et al., 2002; Hamilton and Baulcombe, 1999). This process may also utilize a recombinant DICER or RNAse III introduced into the cells of an organism through recombinant DNA techniques that are readily known to those skilled in the art. Both the DICER enzyme and RNAse III, being naturally occurring in an organism, or being made through recombinant DNA techniques, cleave larger dsRNA strands into smaller oligonucleotides. The DICER enzymes specifically cut the dsRNA molecules into siRNA pieces each of which is about 19-25 nucleotides in length while the RNAse III enzymes normally cleave the dsRNA molecules into 12-15 base-pair siRNA.

The siRNA molecules produced by either of the enzymes have 2 to 3 nucleotide 3' overhangs, and 5' phosphate and 3' hydroxyl termini. The siRNA molecules generated by RNAse III enzyme are the same as those produced by Dicer enzymes in the eukaryotic RNAi pathway and are hence then targeted and degraded by an inherent cellular RNA-degrading mechanism after they are subsequently unwound, separated into single-stranded RNA and hybridize with the RNA sequences transcribed by the target gene. This process results in the effective degradation or removal of the RNA sequence encoded by the nucleotide sequence of the target gene in the target organism. The outcome is the silencing of a particularly targeted nucleotide sequence within the target organism. Detailed descriptions of enzymatic processes can be found in Hannon (2002).

A nucleotide sequence of the present invention can be recorded on computer readable media. As used herein, "computer readable media" refers to any tangible medium of expression that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; optical character recognition formatted computer files, and hybrids of these categories such as magnetic/optical storage media. A skilled artisan can readily appreciate that any of the presently known computer readable mediums can be used to create a manufacture comprising a computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII text file, stored in a database application, such as DB2, Sybase, Oracle, or the like. The skilled artisan can readily adapt any number of data processor structuring formats (e.g. text file or database) in order to obtain computer readable medium having recorded thereon the nucleotide sequence information of the present invention.

Computer software is publicly available which allows a skilled artisan to access sequence information provided in a computer readable medium. Software that implements the BLAST (Altschul et al., 1990) and BLAZE (Brutlag, et al., 1993) search algorithms on a Sybase system can be used to identify open reading frames (ORFs) within sequences such as the Unigenes and EST's that are provided herein and that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As used herein, "a target structural motif," or "target motif," refers to any rationally selected sequence or combination of sequences in which the sequences or sequence(s) are chosen based on a three-dimensional configuration that is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures, siRNAs, and inducible expression elements (protein binding sequences).

B. Recombinant Vectors and Host Cell Transformation

A recombinant DNA vector may, for example, be a linear or a closed circular plasmid. The vector system may be a single vector or plasmid or two or more vectors or plasmids that together contain the total DNA to be introduced into the genome of the bacterial host. In addition, a bacterial vector may be an expression vector. Nucleic acid molecules as set forth in the sequence listing, or fragments thereof, can, for example, be suitably inserted into a vector under the control of a suitable promoter that functions in one or more microbial hosts to drive expression of a linked coding sequence or other DNA sequence. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more selectable marker genes, and an inducible promoter allowing the expression of exogenous DNA.

Expression and cloning vectors may contain a selection gene, also referred to as a selectable marker. This gene encodes a protein necessary for the survival or growth of transformed host cells grown in a selective culture medium. Typical selection genes encode proteins that (a) confer resistance to antibiotics, herbicides, or other toxins, e.g., ampicillin, neomycin, methotrexate, glyphosate, or tetracycline, (b) complement auxotrophic deficiencies, or (c) supply critical nutrients not available from complex media, e.g., the gene encoding D-alanine racemase for Bacilli. Those cells that are successfully transformed with a heterologous protein or fragment thereof produce a protein conferring drug resistance and thus survive the selection regimen.

An expression vector for producing a mRNA can also contain an inducible promoter that is recognized by the host organism and is operably linked to the nucleic acid encoding, the nucleic acid molecule, or fragment thereof, of interest. Inducible promoters suitable for use with bacterial hosts include β-lactamase promoter, *E. coli* λ phage PL and PR promoters, *E. coli* galactose promoter, arabinose promoter, alkaline phosphatase promoter, tryptophan (trp) promoter, and the lactose operon promoter and variations thereof and hybrid promoters such as the tac promoter. However, other known bacterial inducible promoters are suitable. Plant promoters are discussed below.

The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream (5' non-coding sequences), within, or downstream (3' non-translated sequences) of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, and polyadenylation recognition sequences and the like.

Alternatively, the expression constructs can be integrated into the host cell genome with an integrating vector. Integrating vectors typically contain at least one sequence homologous to the chromosome that allows the vector to integrate. Integrations appear to result from recombination between homologous DNA in the vector and the chromosome in the case of bacteria. For example, integrating vectors constructed with DNA from various *Bacillus* strains integrate into the *Bacillus* chromosome (EP 0 127,328). Integrating vectors may also be comprised of bacteriophage or transposon sequences. Suicide vectors are also known in the art.

Construction of suitable vectors containing one or more of the above-listed components employs standard recombinant DNA techniques. Isolated plasmids or DNA fragments can be cleaved, tailored, and re-ligated in the form desired to generate the plasmids required. Examples of available bacterial expression vectors include, but are not limited to, the multifunctional *E. coli* cloning and expression vectors such as Bluescript™ (Stratagene, La Jolla, Calif.); pIN vectors (Van Heeke and Schuster, 1989); and the like.

A yeast recombinant construct can typically include one or more of the following: a promoter sequence, fusion partner sequence, leader sequence, transcription termination sequence, a selectable marker. These elements can be combined into an expression cassette, which may be maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 (Botstein et al., 1979), pCl/1 (Brake et al., 1984), and YRp17 (Stinchcomb et al., 1982). In addition, a replicon may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20 copies.

Useful yeast promoter sequences can be derived from genes encoding enzymes in the metabolic pathway. Examples of such genes include alcohol dehydrogenase (ADH) (EP 0 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EP 0 3215447). The yeast PHO5 gene, encoding acid phosphatase, also provides useful promoter sequences (Myanohara et al., 1983). In addition, synthetic promoters that do not occur in nature also function as yeast promoters. Examples of such hybrid promoters include the ADH regulatory sequence linked to the GAP transcription activation region (U.S. Pat. Nos. 4,876,197 and 4,880,734). Examples of transcription terminator sequences and other yeast-recognized termination sequences, such as those coding for glycolytic enzymes, are known to those of skill in the art.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombination between homologous DNA in the vector and the yeast chromosome (Orr-Weaver et al., 1983). An integrating vector may be directed to a specific locus in yeast by selecting the appropriate homologous sequence for inclusion in the vector. See Orr-Weaver et al., supra. One or more expression constructs may integrate, possibly affecting levels of recombinant protein produced (Rine et al., 1983).

The present invention also contemplates transformation of a nucleotide sequence of the present invention into a plant to achieve inhibitory levels of expression of one or more dsRNA molecules. A transformation vector can be readily prepared using methods available in the art. The transformation vector typically comprises one or more nucleotide sequences capable of being transcribed to an RNA molecule substantially homologous and/or complementary to one or more nucleotide sequences encoded by the genome of the target organism, and may comprise an intron sequence within the otherwise homologous or complementary sequence such that uptake by the organism of the RNA transcribed and processed from the one or more nucleotide sequences results in down-regulation of expression of at least one of the respective nucleotide sequences of the genome of the target organism.

The transformation vector may be termed a dsDNA construct and may also be defined as a recombinant molecule, a pest or disease control agent, a genetic molecule or a chimeric genetic construct. A chimeric genetic construct of the present invention may comprise, for example, nucleotide sequences encoding one or more antisense transcripts, one or more sense transcripts, one or more of each of the aforementioned, wherein all or part of a transcript therefrom is homologous to all or part of an RNA molecule comprising an RNA sequence encoded by a nucleotide sequence within the genome of a target organism.

In one embodiment, a plant transformation vector comprises an isolated and purified DNA molecule comprising a heterologous promoter operatively linked to one or more nucleotide sequences of the present invention. The nucleotide sequence may be selected from among those as set forth in the sequence listing, or a fragment thereof. The nucleotide sequence can include a segment coding for all or part of an RNA present within a targeted organism. The RNA transcript may comprise inverted repeats of all or a part of a targeted RNA. The DNA molecule comprising the expression vector may also contain a functional intron sequence positioned either upstream of the coding sequence or even within the coding sequence, and may also contain a five prime (5') untranslated leader sequence (i.e., a UTR or 5'-UTR) positioned between the promoter and the point of translation initiation.

A plant transformation vector may contain sequences from one or more genes, thus allowing production of more than one dsRNA for inhibiting expression of a gene or genes in cells of a target organism. One skilled in the art will readily appreciate that segments of DNA whose sequence corresponds to that present in different genes can be combined into a single composite DNA segment for expression in a transgenic plant. Alternatively, a plasmid of the present invention already containing at least one DNA segment can be modified by the sequential insertion of additional DNA segments between the enhancer and promoter and terminator sequences. In the disease or pest control agent of the present invention designed for the inhibition of multiple genes, the genes to be inhibited can be obtained from the same target species in order to enhance the effectiveness of the control agent. In certain embodiments, the genes can be derived from different pathogen or pest organisms in order to broaden the range of pathogens against which the agent(s) is/are effective. When multiple genes are targeted for suppression or a combination of expression and suppression, a polycistronic DNA element can be fabricated as illustrated and disclosed in Application Publication No. US 2004-0029283.

Promoters that function in different plant species are also well known in the art. Promoters useful for expression of polypeptides in plants include those that are inducible, viral, synthetic, or constitutive as described in Odell et al. (1985), and/or promoters that are temporally regulated, spatially regulated, and spatio-temporally regulated. Preferred promoters include the enhanced CaMV35S promoters, and the FMV35S promoter. A fragment of the CaMV35S promoter exhibiting root-specificity may also be preferred. A number of tissue-specific promoters have been identified and are known in the art (e.g. U.S. Pat. Nos. 5,110,732; 5,837,848; Hirel et al. 1992; Stahl et al. 2004; Busk et al., 1997).

A recombinant DNA vector or construct of the present invention typically comprises a selectable marker that confers a selectable phenotype on plant cells. Selectable markers may also be used to select for plants or plant cells that contain the exogenous nucleic acids encoding polypeptides or proteins of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene which codes for kanamycin resistance and can be selected for using kanamycin, G418, etc., a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulfonylurea resistance; and a methotrexate resistant DHFR gene. Examples of such selectable markers are illustrated in U.S. Pat. Nos. 5,550,318; 5,633,435; 5,780,708 and 6,118,047.

A recombinant vector or construct of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson, 1987; Jefferson et al., 1987); an R-locus gene, which encodes a product that regulates the production of anthocyanin pigments (red color) in plant tissues (Dellaporta et al., 1988); a β-lactamase gene (Sutcliffe et al., 1978), a gene which encodes an enzyme for which various chromogenic substrates are known (e.g., PADAC, a chromogenic cephalosporin); a luciferase gene (Ow et al., 1986) a xylE gene (Zukowsky et al., 1983) which encodes a catechol dioxygenase that can convert chromogenic catechols; an α-amylase gene (Ikatu et al., 1990); a tyrosinase gene (Katz et al., 1983) which encodes an enzyme capable of oxidizing tyrosine to DOPA and dopaquinone which in turn condenses to melanin; an α-galactosidase, which catalyzes a chromogenic α-galactose substrate.

Preferred plant transformation vectors include those derived from a Ti plasmid of *Agrobacterium tumefaciens* (e.g. U.S. Pat. Nos. 4,536,475, 4,693,977, 4,886,937, 5,501,967 and EP 0 122 791). *Agrobacterium rhizogenes* plasmids (or "Ri") are also useful and known in the art. Other preferred plant transformation vectors include those disclosed, e.g., by Herrera-Estrella (1983); Bevan (1983), Klee (1985) and EPO 0 120 516.

In general it may be preferred to introduce a functional recombinant DNA at a non-specific location in a plant genome. In special cases it may be useful to insert a recombinant DNA construct by site-specific integration. Several site-specific recombination systems exist which are known to function implants include cre-lox as disclosed in U.S. Pat. No. 4,959,317 and FLP-FRT as disclosed in U.S. Pat. No. 5,527,695.

Suitable methods for transformation of host cells for use with the current invention are believed to include virtually any method by which DNA can be introduced into a cell (see, for example, Miki et al., 1993), such as by transformation of protoplasts (U.S. Pat. No. 5,508,184; Omirulleh et al., 1993), by desiccation/inhibition-mediated DNA uptake (Potrykus et al., 1985), by electroporation (U.S. Pat. No. 5,384,253), by agitation with silicon carbide fibers (Kaeppler et al., 1990; U.S. Pat. No. 5,302,523; and U.S. Pat. No. 5,464,765), by *Agrobacterium*-mediated transformation (U.S. Pat. Nos. 5,563,055; 5,591,616; 5,693,512; 5,824,877; 5,981,840; 6,384,301) and by acceleration of DNA coated particles (U.S. Pat. Nos. 5,015,580; 5,550,318; 5,538,880; 6,160,208; 6,399,861; 6,403,865; Padgette et al. 1995), etc. Through the application of techniques such as these, the cells of virtually any species may be stably transformed. In the case of multicellular species, the transgenic cells may be regenerated into transgenic organisms.

The most widely utilized method for introducing an expression vector into plants is based on the natural transformation system of *Agrobacterium* (for example, Horsch et al., 1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. Descriptions of *Agrobacterium* vector systems and methods for *Agrobacterium*-mediated gene transfer are provided by numerous references, including Gruber et al., 1993; Miki et al., 1993, Moloney et al., 1989, and U.S. Pat. Nos. 4,940,838 and 5,464,763. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector (Broothaerts et al., 2005).

Plant transformation vectors can be prepared, for instance, by inserting the dsRNA producing nucleic acids disclosed herein into plant transformation vectors and introducing these into plants. One known vector system has been derived by modifying the natural gene transfer system of *Agrobacterium tumefaciens*. The natural system comprises large Ti (tumor-inducing) plasmids containing a large segment, known as the T-DNA, which is transferred to transformed plant cells. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences. The T-region may also contain a selectable marker for efficient recovery of transgenic cells and plants, and a multiple cloning site for inserting sequences for transfer, such as a dsRNA encoding nucleic acid.

Transgenic plants may be regenerated from a transformed plant cell by methods well known in the field of plant cell culture. A transgenic plant formed using *Agrobacterium* transformation methods typically contains a single simple recombinant DNA sequence inserted into one chromosome and is referred to as a transgenic event. Such transgenic plants can be referred to as being heterozygous for the inserted exogenous sequence. A transgenic plant homozygous with respect to a transgene can be obtained by sexually mating (selfing) an independent segregant transgenic plant that contains a single exogenous gene sequence to itself, for example an F0 plant, to produce F1 seed. One fourth of the F1 seed produced will be homozygous with respect to the transgene. Germinating F1 seed results in plants that can be tested for heterozygosity, typically using a SNP assay or a thermal amplification assay that allows for the distinction between heterozygotes and homozygotes (i.e., a zygosity assay). Crossing a heterozygous plant with itself or another heterozygous plant results in only heterozygous progeny.

C. Nucleic Acid Expression and Target Gene Suppression

The present invention provides, as an example, a transformed host plant for a pathogenic target organism, transformed plant cells and transformed plants and their progeny. The transformed plant cells and transformed plants may be engineered to express one or more of the dsRNA sequences including siRNA, under the control of a heterologous promoter to provide a pest or pathogen-protective effect. These sequences may be used for gene suppression in a pest or pathogen, thereby reducing the level or incidence of disease caused by the pathogen on a protected transformed host organism. As used herein the words "gene suppression" are intended to refer to any of the well-known methods for reducing the levels of protein produced as a result of gene transcription to mRNA and subsequent translation of the mRNA.

Gene suppression is also intended to mean the reduction of protein expression from a gene or a coding sequence including posttranscriptional gene suppression and transcriptional suppression. Posttranscriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect RNA interference (RNAi).

Transcriptional suppression is mediated by the presence in the cell of a dsRNA gene suppression agent exhibiting substantial sequence identity to a target DNA sequence or the complement thereof. Gene suppression can be effective against target genes in plant pests or pathogens that may take up or contact plant material containing gene suppression agents, specifically designed to inhibit or suppress the expression of one or more homologous or complementary sequences in the cells of the target organism. Post-transcriptional gene suppression by anti-sense or sense oriented RNA to regulate gene expression in plant cells is disclosed in U.S. Pat. Nos. 5,107,065, 5,759,829, 5,283,184, and 5,231,020. The use of dsRNA to suppress genes in plants is disclosed in WO 99/53050, WO 99/49029, U.S. Patent Application Publication No. 2003/0175965, and 2003/0061626, U.S. patent application Ser. No. 10/465,800, and U.S. Pat. Nos. 6,506,559, and 6,326,193.

A beneficial method of gene suppression employs both sense-oriented and anti-sense-oriented, transcribed RNA which is stabilized, e.g., as a hairpin and stem and loop structure. A preferred DNA construct for effecting gene suppression in a target organism is one in which a first segment encodes an RNA exhibiting an anti-sense orientation exhibiting substantial identity to a segment of a gene targeted for suppression, which is linked to a second "spacer" segment, and to a third segment encoding an RNA exhibiting substantial complementarity to the first segment. Such a construct forms a stem and loop structure by hybridization of the first segment with the third segment, and a loop structure from the second segment nucleotide sequences linking the first and third segments (see WO94/01550, WO98/05770, US 2002/0048814, and US 2003/0018993).

According to one embodiment of the present invention, there is provided a nucleotide sequence, for which in vitro expression results in transcription of a stabilized RNA sequence that is substantially homologous to an RNA molecule that comprises an RNA sequence encoded by a nucleotide sequence within the genome of the target organism. Thus, after the target organism takes up the stabilized RNA sequence, a down-regulation of the nucleotide sequence corresponding to the target gene in the cells of a target organism is effected.

Inhibition of a target gene using the stabilized dsRNA technology of the present invention is sequence-specific in that nucleotide sequences corresponding to the duplex region of the RNA are targeted for genetic inhibition. RNA containing a nucleotide sequences identical to a portion of the target gene is preferred for inhibition. RNA sequences with insertions, deletions, and single point mutations relative to the target sequence may also be found to be effective for inhibition. In performance of the present invention, it is preferred that the inhibitory dsRNA and the portion of the target gene share at least from about 80% sequence identity, or from about 90% sequence identity, or from about 95% sequence identity, or from about 99% sequence identity, or even about 100% sequence identity. Alternatively, the duplex region of the RNA may be defined functionally as a nucleotide sequence that is capable of hybridizing with a portion of the target gene transcript. A less than full length sequence exhibiting a greater homology compensates for a longer less homologous sequence. The length of the identical nucleotide sequences may be at least about 20, 50, 100, 200, 300, 400, 500 or at least about 1000 bases. Normally, a sequence of greater than about 20 nucleotides is to be used. The introduced nucleic acid molecule may not need to possess absolute homology, and may not need to be full length, relative to either the primary transcription product or fully processed mRNA of the target gene. Therefore, those skilled in the art need to realize that, as disclosed herein, 100% sequence identity between the RNA and the target gene may not be required to practice specific embodiments of the present invention. Those skilled in the art will also recognize that a greater degree of sequence similarity between the introduced nucleic acid and the target sequence may result in a higher level of gene suppression.

Inhibition of target gene expression may be quantified by measuring either the endogenous target RNA or the protein produced by translation of the target RNA and the consequences of inhibition can be confirmed by examination of the outward properties of the cell or organism. Techniques for quantifying RNA and proteins are well known to one of ordinary skill in the art.

In certain embodiments gene expression is inhibited by at least 10%, preferably by at least 33%, more preferably by at least 50%, and yet more preferably by at least 80%. In particularly preferred embodiments of the invention gene expression is inhibited by at least 80%, more preferably by at least 90%, more preferably by at least 95%, or by at least 99% within cells in the target organism so that a significant inhibition takes place. Significant inhibition is intended to refer to sufficient inhibition that results in a detectable phenotype (e.g., cessation of vegetative or reproductive growth, feeding, mortality, etc.) or a detectable decrease in RNA and/or protein corresponding to the target gene being inhibited. Although in certain embodiments of the invention inhibition occurs in substantially all cells of the target organism, in other preferred embodiments inhibition occurs in only a subset of cells expressing the gene.

dsRNA molecules may be synthesized either in vivo or in vitro. The dsRNA may be formed by a single self-complementary RNA strand or from two complementary RNA strands. Endogenous RNA polymerase of the cell may mediate transcription in vivo, or cloned RNA polymerase can be used for transcription in vivo or in vitro. Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus.

A RNA, dsRNA, siRNA, or miRNA of the present invention may be produced chemically or enzymatically by one skilled in the art through manual or automated reactions or in vivo in another organism. RNA may also be produced by partial or total organic synthesis; any modified ribonucleotide can be introduced by in vitro enzymatic or organic synthesis. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593,874, 5,698,425, 5,712,135, 5,789,214, and 5,804,693). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

For transcription from a transgene in vivo or an expression construct, a regulatory region (e.g., promoter, enhancer, silencer, and polyadenylation) may be used to transcribe the RNA strand (or strands). Therefore, in one embodiment, the nucleotide sequences for use in producing RNA molecules may be operably linked to one or more promoter sequences functional in a microorganism, a fungus or a plant host cell. Ideally, the nucleotide sequences are placed under the control of an endogenous promoter, normally resident in the host genome. The endogenous promoter is thus typically a heterologous promoter with respect to the transgene. The nucleotide sequence of the present invention, under the control of an operably linked promoter sequence, may further be flanked by additional sequences that advantageously affect its transcription and/or the stability of a resulting transcript. Such sequences are generally located upstream of the operably linked promoter and/or downstream of the 3' end of the expression construct and may occur both upstream of the promoter and downstream of the 3' end of the expression construct, although such an upstream sequence only is also contemplated.

As used herein, the term "gene suppression agent" refers to a particular RNA molecule consisting of a first RNA segment, a second RNA segment, and a third RNA segment. The first and the third RNA segments lie within the length of the RNA molecule, are substantially inverted repeats of each other, and are linked together by the second RNA segment. At least one of the nucleotide sequences encoding the first and third RNA segments may comprise an intron sequence. The complementarity between the first and the third RNA segments upon removal of the intron results in the ability of the two segments to hybridize in vivo and in vitro to form a double stranded molecule, i.e., a stem, linked together at one end of each of the first and third segments by the second segment which forms a loop, so that the entire structure forms into a stem and loop structure, or an even more tightly hybridizing structures may form into a stem-loop knotted structure. The first and the third segments correspond invariably and not respectively to a sense and an antisense sequence with respect to the target RNA transcribed from the target gene in the target organism that is suppressed by the ingestion or uptake of the dsRNA molecule. The control agent can also be a substantially purified (or isolated) nucleic acid molecule and more specifically nucleic acid molecules or nucleic acid fragment molecules thereof from a genomic DNA (gDNA) or cDNA library. Alternatively, the fragments may comprise smaller oligonucleotides having from about 15 to about 250 nucleotide residues, and more preferably, about 15 to about 30 nucleotide residues.

As used herein, the term "genome" as it applies to cells of a target organism or a host plant encompasses not only chromosomal DNA found within the nucleus, but organelle DNA found within subcellular components of the cell. The DNA's of the present invention introduced into plant cells can therefore be either chromosomally integrated or organelle-localized. The term "genome" as it applies to bacteria encompasses both the chromosome and plasmids within a bacterial host cell. The DNA's of the present invention introduced into bacterial host cells can therefore be either chromosomally integrated or plasmid-localized.

As used herein, the term "target organism" or "target crop pest" refers to Ascomycetes, Basidiomycetes, Deuteromycetes, Oomycetes, viruses, nematodes, insects, and the like that are present in the environment and that may infect, cause disease, or infest host plant material transformed to express or coated with a double stranded gene suppression agent containing the gene suppression agent. As used herein, "phytopathogenic microorganism" refers to microorganisms that can cause plant disease, including viruses, bacteria, fungi, oomycetes, chytrids, algae, and nematodes. As used herein, the term "plant pest" refers to insects such as beetles, grasshoppers, weevils, aphids, mites, leafhoppers, thrips, whiteflies, rootworms, borers, grubs, and the like.

As used herein, a "pathogen resistance" or "pest resistance" trait is a characteristic of a host plant that causes the plant host to be resistant to attack from a pest or pathogen that typically is capable of inflicting damage or loss to the plant. Such resistance can arise from a natural mutation or more typically from incorporation of recombinant DNA that confers resistance. To impart resistance to a transgenic plant a recombinant DNA can, for example, be transcribed into a RNA molecule that forms a dsRNA molecule within the tissues or fluids of the recombinant plant. Formation of the RNA molecule may also include processing, such as intron splicing. The dsRNA molecule is comprised in part of a segment of RNA that is identical to a corresponding RNA segment encoded from a DNA sequence within a pest or pathogen that prefers to cause disease on the recombinant plant. Expression of the corresponding gene within the target organism is suppressed by the dsRNA, and the suppression of expression of the gene in the target organism results in the plant being resistant to the pest or pathogen. Fire et al., (U.S. Pat. No. 6,506,599) generically described inhibition of pest infestation, providing specifics only about several nucleotide sequences that were effective for inhibition of gene function in the nematode species *Caenorhabditis elegans*. Similarly, US 2003/0061626 describes the use of dsRNA for inhibiting gene function in a variety of nematode pests. US 2003/0150017 describes using dsDNA sequences to transform host cells to express corresponding dsRNA sequences that are substantially identical to target sequences in specific pests, and particularly describe constructing recombinant plants expressing such dsRNA sequences for ingestion by various plant pests, facilitating down-regulation of a gene in the genome of the pest organism and improving the resistance of the plant to the pest infestation.

The modulatory effect of dsRNA is applicable to a variety of genes expressed in a pest or pathogen, including, for example, endogenous genes responsible for cellular metabolism or cellular transformation, including house keeping genes, transcription factors and other genes which encode polypeptides involved in cellular metabolism.

As used herein, the phrase "inhibition of gene expression" or "inhibiting expression of a target gene in the cell of a target organism" refers to the absence (or observable decrease) within the target organism in the level of protein and/or mRNA product from the target gene. Specificity refers to the ability to inhibit the target gene without manifest effects on other genes of the cell and without any effects on any gene within the cell that is producing the dsRNA molecule. The inhibition of gene expression of the target gene in the target organism may result in novel phenotypic traits in the target organism. To create a durable transgenic trait, production of dsRNA and/or its processing into siRNA would need to occur over both the developmental lifetime time of the individual transgenic crop plant and over generational time of a target organism.

The present invention provides in part a delivery system for the delivery of the target organism control agents by ingestion of host cells or the contents of the cells. In accordance with another embodiment, the present invention involves generating a transgenic plant cell or a plant that contains a recombinant DNA construct transcribing the stabilized dsRNA molecules of the present invention. As used herein, the phrase "taking up" refers to the process of an agent coming in contact with, or entering, a cell of a target organism. This may occur, for instance, by diffusion, active uptake, ingestion, feeding, injection, or soaking. As used herein, the phrase "generating a transgenic plant cell or a plant" refers to the methods of employing the recombinant DNA technologies readily available in the art (e.g., by Sambrook, et al., 1989) to construct a plant transformation vector transcribing the stabilized dsRNA molecules of the present invention, to transform the plant cell or the plant and to generate the transgenic plant cell or the transgenic plant that contain the transcribed, stabilized dsRNA molecules.

The invention also provides methods comprising exposure of a target organism to one or more control agent(s) of the present invention incorporated in a spray mixer and applied to the surface of a host, such as a host plant, including as a seed treatment (e.g. U.S. Pat. No. 6,551,962). Such control agent(s) may thus provide for exposure of a target organism by means of a dsRNA of the invention that targets suppression of one or more essential or pathogenicity related gene(s) in the target organism in combination with one or more of the following: a Bt toxin as set forth in the website (lifesci.sussex.ac.uk/home/Neil_Crickmore/Bt/index.html), a biocontrol agent, an insecticide, and a seed treatment. Methods for formulating and applying such seed treatments are well known in the art.

Such applications, including a seed treatment, may include an insecticide known in the art. Examples are set forth in U.S. Pat. No. 6,551,962, including a carbaryl insecticide, fenvalerate, esfenvalerate, malathion, a carbofuran insecticide, chloropyrifos, fonophos, phorate, terbufos, permethrin, a neonicotinoid, and tefluthrin among others. Thus, a combination of lethality may be provided to a target organism, yielding a means for resistance management to prevent development of resistance by a target organism to a particular pesticidal composition. Biocontrol agents are known in the art, and may include, for instance, naturally-occurring or recombinant bacteria or fungi from the genera *Rhizobium, Bacillus, Pseudomonas, Serratia, Clavibacter, Trichoderma, Glomus, Gliocladium* and mycorrhizal fungi, among others. A method for such resistance management is also provided by the invention.

Combinations of control agent(s) that may be employed with the invention include one or more polynucleotides that comprise or express a dsRNA of the present invention and at least one other agent toxic to an insect such as a coleopteran. Such combinations may be used to provide a "synergistic" effect. When it is said that some effects are "synergistic", it is meant to include the synergistic effects of the combination on the pesticidal activity (or efficacy) of the combination of the dsRNA and the pesticide. However, it is not intended that such synergistic effects be limited to the pesticidal activity, as such effects include unexpected advantages of increased scope of activity, advantageous activity profile as related to type and amount of damage reduction, decreased cost of pesticide and application, decreased pesticide distribution in the environment, decreased pesticide exposure of personnel who produce, handle and plant crop seed, and other advantages known to those skilled in the art.

In an exemplary embodiment, ingestion of the control agent(s) by a pest or pathogen organism delivers the control agents to the cells of the organism. In yet another embodiment, the RNA molecules themselves are encapsulated in a synthetic matrix such as a polymer and applied to the surface of a host such as a plant. Ingestion of the host cells by a target organism permits delivery of the control agents to the organism and results in down-regulation of a target gene in the organism.

It is envisioned that the compositions of the present invention can be incorporated within the seeds of a plant species either as a product of expression from a recombinant gene incorporated into a genome of the plant cells, or incorporated into a coating or seed treatment that is applied to the seed before planting. The plant cell containing a recombinant gene is considered herein to be a transgenic event.

The present invention provides in part a delivery system for the delivery of disease control agents to target organisms. The stabilized dsRNA or siRNA molecules of the present invention may be directly introduced into the cells of a target organism, or introduced into an extracellular space (e.g. the plant apoplast). Methods for introduction may include direct mixing of RNA with media for the organism, as well as engineered approaches in which a species that is a host is engineered to express the dsRNA or siRNA. In one in vitro embodiment, for example, the dsRNA or siRNA molecules may be incorporated into, or overlaid on the top of, growth media. In another embodiment, the RNA may be sprayed onto a plant surface. In still another embodiment, the dsRNA or siRNA may be expressed by microorganisms and the microorganisms may be applied onto a plant surface or introduced into a root or stem by a physical means such as an injection. In still another embodiment, a plant may be genetically engineered to express the dsRNA or siRNA in an amount sufficient to affect target gene expression in the target organism known to infect or infest a plant host.

It is also anticipated that dsRNA's produced by chemical or enzymatic synthesis may be formulated in a manner consistent with common agricultural practices and used as spray-on products for controlling plant disease. The formulations may include the appropriate stickers and wetters required for efficient foliar coverage as well as UV protectants to protect dsRNAs from UV damage. Such additives are commonly used in the bioinsecticide industry and are well known to those skilled in the art. Such applications could be combined with other spray-on insecticide applications, biologically based or not, to enhance plant protection from infection or insect feeding damage. For instance, the RNA molecules may also be combined with another control agent, for instance an insecticidal agent such as a Cry protein, or insecticidal fragment thereof.

The present invention also relates to recombinant DNA constructs for expression in a microorganism. Exogenous nucleic acids from which an RNA of interest is transcribed can be introduced into a microbial host cell, such as a bacterial cell or a fungal cell, using methods known in the art.

The nucleotide sequences of the present invention may be introduced into a wide variety of prokaryotic and eukaryotic microorganism hosts to produce the stabilized dsRNA or siRNA molecules. The term "organism" includes prokaryotic and eukaryotic species such as bacteria, and fungi. Fungi include yeasts and filamentous fungi, among others. Illustrative prokaryotes, both Gram-negative and Gram-positive, include Enterobacteriaceae, such as *Escherichia, Erwinia, Shigella, Salmonella*, and *Proteus*; Bacillaceae; Rhizobiaceae, such as *Rhizobium*; Spirillaceae, such as photobacterium; *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae, *Actinomycetales*, and Nitrobacteraceae. Among eukaryotes are fungi, such as Phycomycetes and Ascomycetes which includes filamentous fungi such as *Sclerotinia, Erysiphe*, and the like, and yeast, such as *Saccharomyces* and *Schizosaccharomyces*; Basidiomycetes, such as *Rhodotorula, Aureobasidium, Sporobolomyces*, and the like; and Oomycetes, such as *Phytophthora*.

D. Transgenic Plants

The present invention provides a transgenic plant including, without limitation, alfalfa, corn, canola, rice, soybean, tobacco, turfgrass, and wheat, among others. The present invention provides seeds and plants having one or more transgenic event(s). Combinations of events are referred to as "stacked" transgenic events. These stacked transgenic events can be events that are directed at the same target organism, or they can be directed at different target pathogens or pests. In one embodiment, a seed having the ability to express a nucleic acid provided herein also has the ability to express at least one other agent, including, but not limited to, an RNA molecule the sequence of which is derived from the sequence of an RNA expressed in a target pathogen and that forms a double stranded RNA structure upon expressing in the seed or cells of a plant grown from the seed, wherein the ingestion of one or more cells of the plant by the target pathogen results in the suppression of expression of the RNA in the cells of the target pathogen.

In certain embodiments, a seed having the ability to express a dsRNA the sequence of which is derived from a target organism also has a transgenic event that provides herbicide tolerance. One beneficial example of a herbicide tolerance gene provides resistance to glyphosate, N-(phosphonomethyl) glycine, including the isopropylamine salt form of such herbicide.

Benefits provided by the present invention may include, but are not limited to: the ease of introducing dsRNA into the target organism's cells, the low concentration of dsRNA which can be used, the stability of dsRNA, and the effectiveness of the inhibition. The ability to use a low concentration of a stabilized dsRNA avoids several disadvantages of anti-sense interference. The present invention is not limited to in vitro use or to specific sequence compositions, to a particular set of target genes, a particular portion of the target gene's nucleotide sequence, or a particular transgene or to a particular delivery method, as opposed to the some of the available techniques known in the art, such as antisense and co-suppression. Furthermore, genetic manipulation becomes possible in organisms that are not classical genetic models.

In order to achieve inhibition of a target gene selectively within a target organism species that it is desired to control, the target gene should preferably exhibit a low degree of sequence identity with corresponding genes in a plant or a vertebrate animal. Preferably the degree of the sequence identity is less than approximately 80%. More preferably the degree of the sequence identity is less than approximately 70%. Most preferably the degree of the sequence identity is less than approximately 60%.

In addition to direct transformation of a plant with a recombinant DNA construct, transgenic plants can be prepared by crossing a first plant having a recombinant DNA construct with a second plant lacking the construct. For example, recombinant DNA for gene suppression can be introduced into first plant line that is amenable to transformation to produce a transgenic plant that can be crossed with a second plant line to introgress the recombinant DNA for gene suppression into the second plant line.

The present invention can be, in practice, combined with other disease control traits in a plant to achieve desired traits for enhanced control of plant disease. Combining disease control traits that employ distinct modes-of-action can provide protected transgenic plants with superior consistency and durability over plants harboring a single control trait because of the reduced probability that resistance will develop in the field.

The invention also relates to commodity products containing one or more of the sequences of the present invention, and produced from a recombinant plant or seed containing one or more of the nucleotide sequences of the present invention are specifically contemplated as embodiments of the present invention. A commodity product containing one or more of the sequences of the present invention is intended to include, but not be limited to, meals, oils, crushed or whole grains or seeds of a plant, or any food product comprising any meal, oil, or crushed or whole grain of a recombinant plant or seed containing one or more of the sequences of the present invention. The detection of one or more of the sequences of the present invention in one or more commodity or commodity products contemplated herein is defacto evidence that the commodity or commodity product is composed of a transgenic plant designed to express one or more of the nucleotides sequences of the present invention for the purpose of controlling plant disease using dsRNA mediated gene suppression methods.

E. Obtaining Nucleic Acids

The present invention provides methods for obtaining a nucleic acid comprising a nucleotide sequence for producing a dsRNA including siRNA. In one embodiment, such a method comprises: (a) probing a cDNA or gDNA library with a hybridization probe comprising all or a portion of a nucleotide sequence or a homolog thereof from a targeted organism; (b) identifying a DNA clone that hybridizes with the hybridization probe; (c) isolating the DNA clone identified in step (b); and (d) sequencing the cDNA or gDNA fragment that comprises the clone isolated in step (c) wherein the sequenced nucleic acid molecule transcribes all or a substantial portion of the RNA nucleotide acid sequence or a homolog thereof.

In another embodiment, a method of the present invention for obtaining a nucleic acid fragment comprising a nucleotide sequence for producing a substantial portion of a dsRNA or siRNA comprises: (a) synthesizing first and a second oligonucleotide primers corresponding to a portion of one of the nucleotide sequences from a targeted organism; and (b) amplifying a cDNA or gDNA insert present in a cloning vector using the first and second oligonucleotide primers of step (a) wherein the amplified nucleic acid molecule transcribes a substantial portion of the a substantial portion of a dsRNA or siRNA of the present invention.

In practicing the present invention, a target gene may be derived from a pest or pathogen species that causes damage to the crop plants and subsequent yield losses. It is contemplated that several criteria may be employed in the selection of preferred target genes. The gene may be one whose protein product has a rapid turnover rate, so that dsRNA inhibition will result in a rapid decrease in protein levels. In certain embodiments it is advantageous to select a gene for which a small drop in expression level results in deleterious effects for the target organism. If it is desired to target a broad range of pest or pathogen species, a gene is selected that is highly conserved across these species. Conversely, for the purpose of conferring specificity, in certain embodiments of the invention, a gene is selected that contains regions that are poorly conserved between individual species, or between the target and other organisms. In certain embodiments it may be desirable to select a gene that has no known homologs in other organisms. As used herein, the term "derived from" refers to a specified nucleotide sequence that may be obtained from a particular specified source or species, albeit not necessarily directly from that specified source or species.

Other target genes for use in the present invention may include, for example, those that play important roles in the viability, growth, feeding, development, reproduction and infectivity of the target organism. These target genes may be one of the house keeping genes, transcription factors and the like. Additionally, the nucleotide sequences for use in the present invention may also be derived from plant, viral, bacterial or insect genes whose functions have been established from literature and the nucleotide sequences of which share substantial similarity with the target genes in the genome of a target organism. According to one aspect of the present invention, the target sequences may essentially be derived from the targeted organism.

For the purpose of the present invention, the dsRNA or siRNA molecules, or polynucleotides that encode them, may be obtained by polymerase chain (PCR™) amplification of a target gene sequences derived from a gDNA or cDNA library or portions thereof. The DNA library may be prepared using methods known to the ordinary skilled in the art and DNA/RNA may be extracted. Genomic DNA or cDNA libraries generated from a target organism may be used for PCR™ amplification for production of the dsRNA or siRNA. The target genes may be then be PCR™ amplified and sequenced using the methods readily available in the art. One skilled in the art may be able to modify the PCR™ conditions to ensure optimal PCR™ product formation. The confirmed PCR™ product may be used as a template for in vitro transcription to generate sense and antisense RNA with the included minimal promoters.

The present inventors contemplate that nucleic acid sequences identified and isolated from any pest or pathogen species may be used in the present invention for control of plant disease. In one aspect of the present invention, the nucleic acid may be derived from a Western Corn Rootworm (*Diabrotica virgifera virgifera*). The isolated nucleic acids may be useful, for example, in identifying a target gene and one or more sequences within the gene that encode effective siRNA molecules. They may also be useful in constructing a recombinant vector according to the method of the present invention that produces stabilized dsRNAs or siRNAs of the present invention for protecting plants from the rootworm. Therefore, in one embodiment, the present invention comprises isolated and purified nucleotide sequences that may be used as plant pest or disease control agents.

The nucleic acids that may be used in the present invention may also comprise isolated and substantially purified Unigenes and EST nucleic acid molecules or nucleic acid fragment molecules thereof. EST nucleic acid molecules may encode significant portions of, or indeed most of, the polypeptides. Alternatively, the fragments may comprise smaller oligonucleotides having from about 15 to about 250 nucleotide residues, and more preferably, about 15 to about 30 nucleotide residues. Alternatively, the nucleic acid molecules for use in the present invention may be from cDNA libraries from a target organism of interest.

Nucleic acid molecules and fragments thereof from a pest or pathogen species may be employed to obtain other nucleic acid molecules from other species for use in the present invention to produce desired dsRNA and siRNA molecules. Such nucleic acid molecules include the nucleic acid molecules that encode the complete coding sequence of a protein and promoters and flanking sequences of such molecules. In addition, such nucleic acid molecules include nucleic acid molecules that encode for gene family members. Such molecules can be readily obtained by using the above-described nucleic acid molecules or fragments thereof to screen cDNA or genomic DNA libraries. Methods for forming such libraries are well known in the art.

As used herein, the phrase "coding sequence", "structural nucleotide sequence" or "structural nucleic acid molecule" refers to a nucleotide sequence that is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA, cDNA, EST and recombinant nucleotide sequences.

The term "recombinant DNA" or "recombinant nucleotide sequence" refers to DNA that contains a genetically engineered modification through manipulation via mutagenesis, restriction enzymes, and the like.

For many of the pests and pathogens that are potential targets for control by the present invention, there may be limited information regarding the sequences of most genes or the phenotype resulting from mutation of particular genes. Therefore, it is contemplated that selection of appropriate genes from pathogens for use in the present invention may be accomplished through use of information available from study of the corresponding genes in a model organism such as *Saccharomyces cerevisiae*, or in a nematode species such as *C. elegans*, in an insect species, or in a plant species, in which the genes have been characterized. In some cases it will be possible to obtain the sequence of a corresponding gene from a target pest or pathogen by searching databases such as GenBank using either the name of the gene or the sequence from, for example, Drosophila, another insect, a nematode, or a plant from which the gene has been cloned. Once the sequence is obtained, PCR™ may be used to amplify an appropriately selected segment of the gene in the pathogen for use in the present invention.

In order to obtain a DNA segment from the corresponding gene, PCR™ primers may be designed based on the sequence as found in another organism from which the gene has been cloned. The primers are designed to amplify a DNA segment of sufficient length for use in the present invention. DNA (either genomic DNA or cDNA) is prepared from the pathogen, and the PCR™ primers are used to amplify the DNA segment. Amplification conditions are selected so that amplification will occur even if the primers do not exactly match the target sequence. Alternately, the gene (or a portion thereof) may be cloned from a gDNA or cDNA library prepared from the pathogen species, using the known gene as a probe. Techniques for performing PCR™ and cloning from libraries are known. Further details of the process by which DNA segments from target pathogen species may be isolated based on the sequence of genes previously cloned from other species are provided in the Examples. One of ordinary skill in the art will recognize that a variety of techniques may be used to isolate gene segments from plant pest and pathogenic organisms that correspond to genes previously isolated from other species.

Example 1

Effects of dsRNA Presentation Size on Gene Suppression in Corn Rootworm

Bio-assay of dsRNA constructs encoding portions of the western corn rootworm (*Diabrotica virgifera virgifera*; WCR) V-ATPase subunit A gene demonstrated efficacy in gene suppression. Additional work has determined that a 50 bp segment of the WCR V-ATPase subunit A gene (SEQ ID NO:1), when presented as a dsRNA, is sufficient to elicit mortality when tandemly duplicated 5 times, but is ineffective as a 50 bp monomer (Table 1). The 50 bp segment embedded in a neutral carrier for a total dsRNA of 100 bp was also effective, indicating that there are size restrictions on efficient uptake of dsRNA into insects susceptible to RNAi.

Reduced efficacy of smaller unit sizes was also seen using a different gene sequence consisting of 27 bp derived from a *D. virgifera virgifera* sequence encoding Dv49 (SEQ ID NO:2), a putative ortholog of a Drosophila binding/carrier protein (FlyBase sequence CG8055 (SEQ ID NO:3)). A synthetic 27 bp dsRNA segment of Dv49 failed to show activity when fed to insects at 1 ppm (Table 2). The same 27 bp segment embedded in a vector backbone sequence to create a 50 bp dsRNA resulted in increased efficacy. However efficacy was still less than the same 27mer embedded in a total of 206 bp of dsRNA (Table 2). Adjusting the concentration of dsRNA to achieve an equal molar ratio of 27mer sequence showed the 50mer caused no significant mortality (Table 2). Thus, two very different species, *C. elegans* and *D. virgifera*, exhibit an apparent need for dsRNA of minimum size to permit efficient uptake. This observation indicates the importance of ensuring the production of dsRNA in planta of sufficient size to enable uptake and subsequent control of the targeted pest, rather than simply the production of smaller siRNAs that are less likely to be as effective when contacted by a target.

TABLE 1

Impact of dsRNA size on control of WCR in diet bio-assay fed at 1 ppm.

| dsRNA | Mortality in WCR diet bio-assay [1] |
|---|---|
| *Diabrotica virgifera* V-ATPase subunit A, 50 bp segment | 26.6 ± 4.9 |
| Concatemer 3: 5 tandem copies of *Diabrotica virgifera* V-ATPase subunit A 50 bp segment (250 bp total | 71.0 ± 11.8 * |

[1] Percent mortality and standard error of the means.
* significantly different from untreated control P value < 0.05, Planned Contrasts..

TABLE 2

Impact of dsRNA size on control of WCR in diet bio-assay using 27 bp of Dv49 target alone or embedded in neutral carrier and fed at 1 ppm final dsRNA concentration.

| dsRNA | Mortality in WCR diet bio-assay [1] |
|---|---|
| 27 bp from WCR Dv49 | 6.19 ± 3.81 |
| 27 bp from WCR Dv49 plus 23 bp of vector sequence for total of 50 bp contiguous dsRNA | 25.2 ± 6.7 * |
| 27 bp from WCR Dv49 plus 179 bp of vector sequence for total of 206 bp contiguous dsRNA | 100 * |
| 0.1 ppm of 27 bp from WCR Dv49 + 0.9 ppm of vector sequence (non-contiguous to 27 bp of WCR sequence) | 14.8 ± 4.2 |
| 0.2 ppm bp from WCR Dv49 plus 23 bp of vector sequence for total of 50 bp contiguous dsRNA + 0.9 ppm of vector sequence (non-contiguous to 50 bp of sequence) | 11.2 ± 4.9 |

[1] Percent mortality and standard error of the means.
* significantly different from untreated control, P value < 0.05, Planned Contrasts.

Example 2

Fine Mapping Efficacious Corn Rootworm Gene Targets: 26-28mer Analysis

Effective presentation of dsRNA sequences that are otherwise below efficient uptake size was accomplished by embedding segments down to the level of single siRNAs within "carrier" sequence. The WCR sequence Dv49 was chosen for further analysis due to high efficacy in previous insect bio-assays. A 100 bp fragment (SEQ ID NO:4) located 202 bp from the start of translation was synthesized by PCR, as follows:

The 100 bp segment of the Dv49 target was amplified, using cycling conditions described in Table 4, to produce an antisense template using oligonucleotides Dv49-1 (SEQ ID NO:5) and Dv49-2 (SEQ ID NO:6); and a separate sense template using oligonucleotides Dv49-3 (SEQ ID NO:7) and Dv49-4 (SEQ ID NO:8).

each PCR reaction was used to produce a single stranded transcript with the MEGAshortscript™ kit (Ambion, Cat. #1354) according to manufacturer's instructions. The sense and antisense reactions were mixed, heated to 75° C. for 5 min and allowed to cool to room temperature. Further purification of the annealed 100 bp dsRNA product was completed with the MEGAscript™ RNAi Kit (Ambion, Cat #1626) according to manufacture's instructions. This methodology produced a 100 bp product lacking the T7 promoter sequences.

The 100 bp fragment was used as a template for dsRNA synthesis, and the dsRNA was subjected to insect bioassay. When fed at 0.2 ppm, mortality of WCR was 100% with the 100 bp dsRNA (Table 5). No mortality was observed when feeding dsRNA derived from the vector backbone (180 bp) by itself.

TABLE 3

Oligonucleotides used to clone and amplify 100 bp segment of Dv49 used in 26mer scan evaluation. T7 RNA polymerase promoters are shown in lower case (SEQ ID NO: 5-8)

| Name | Sequence | Target DNA | Orientation | Comments |
|---|---|---|---|---|
| Dv49-1 | AAGAAGAAACGATTGGAAAAGAC | Dv49 | sense | For synthesis of 100mer template for dsRNA production of anti-sense strand when used with Dv49-2. |
| Dv49-2 | taatacgactcactataggCDv49AGTATTTGTGCTAGCTCCTTC | Dv49 | antisense | For synthesis of 100mer template for dsRNA production of anti-sense strand when used with Dv49-1. |
| Dv49-3 | CAGTATTTGTGCTAGCTCCTTC | Dv49 | antisense | For synthesis of 100mer template for dsRNA production of sense strand when used with Dv49-4. |
| Dv49-4 | taatacgactcactataggADv49AGAAGAAACGATTGGAAAAGAC | Dv49 | sense | For synthesis of 100mer template for dsRNA production of sense strand when used with Dv49-3. |

TABLE 4

PCR conditions for amplifications of templates used in dsRNA synthesis.

| Step | Temp (° C.) | Time |
|---|---|---|
| 1 | 94 | 2 minutes |
| 2 | 94 | 30 seconds |
| 3 | 52 | 30 seconds |
| 4 | 72 | 30 seconds |
| 5 | | go to step 2, 33 times |
| 6 | 72 | 2 minutes |
| 7 | | hold at 10 forever |

The following reaction conditions were employed: 1× Sigma REDtaq buffer, 200 µM each dNTP, 0.4 µM each oligonucleotide primer, approximately 200 pg of pMON78428 template, and 2 U of REDtaq polymerase (Sigma, Cat. #D4309) in a 50 µl reaction volume. Five µl of

TABLE 5

Impact of dsRNA size on control of WCR in diet bio-assay using 26 bp Dv49 target embedded in vector sequence as carrier (206 bp final size). 1 ppm and 0.2 ppm assays were run at different times.

| dsRNA | Mortality in WCR diet bio-assay fed at 1 ppm[1] | Mortality in WCR diet bio-assay fed at 0.2 ppm[1] |
|---|---|---|
| Scan 0 | 60.1 ± 4.4 * | 13.3 ± 9.7 |
| Scan 1 | 36.4 ± 16.3 * | 16.3 ± 4.3 |
| Scan 2 | 35.8 ± 9.1 * | 22.6 ± 3.3 * |
| Scan 3 | 85.7 ± 9.0 * | 96.7 ± 3.30 * |
| Scan 4 | 75.0 ± 9.4 * | 42.8 ± 3.8 * |
| Scan 5 | 65.4 ± 11.4 * | 39.4 ± 10.7 * |
| Scan 6 | 92.5 ± 5.0 * | 61.9 ± 8.5 * |
| Scan 7 | 94.6 ± 3.3 * | 80.6 ± 9.4 * |
| Scan 8 | 91.0 ± 5.61 * | 66.7 ± 10.0 * |

TABLE 5-continued

Impact of dsRNA size on control of WCR in diet bio-assay using 26 bp Dv49 target embedded in vector sequence as carrier (206 bp final size). 1 ppm and 0.2 ppm assays were run at different times.

| dsRNA | Mortality in WCR diet bio-assay fed at 1 ppm[1] | Mortality in WCR diet bio-assay fed at 0.2 ppm[1] |
| --- | --- | --- |
| Scan 9 | 41.4 ± 6.8 * | 19.0 ± 7.5 |
| Scan 10 | 7.9 ± 5.1 | 6.7 ± 4.1 |
| Scan 11 | 39.3 ± 5.3 * | 5.4 ± 3.3 |
| Scan 12 | 37.9 ± 6.9 * | 13.7 ± 6.9 |
| Scan 13 | 61.2 ± 6.3 * | 33.3 ± 12.6 * |
| Scan 14 | 70.6 ± 7.3 * | 42.3 ± 7.8 * |
| 100 bp Dv49 base sequence | 100 * | 100 * |
| Vector sequence only | NA | 0.0 * |

[1]Percent mortality and standard error of the means.
* significantly different from untreated control, P value < 0.05, Planned Contrasts.
NA = not assayed To define active 21 bp segments (siRNA-sized) and the effects of single nucleotide polymorphisms (SNPs) on efficacy, 26 bp segments scanning through the 100mer base sequence in a 5 bp register were cloned as follows: 26 bp segments derived from the 100 bp Dv49 test sequence were produced synthetically (Integrated DNA Technologies) as sense and antisense oligonucleotides. Pairs of oligonucleotides used in cloning (SEQ ID NO:9-38) were annealed and a 3' A-overhang was added by setting up the following reaction: 1× Sigma REDtaq buffer, 200 µM each dNTP, 0.4 µM each oligonucleotide primer and 2 U of REDtaq polymerase and incubation at 75° C. for 2 minutes followed by 20 minutes at 50° C. Two µl of each PCR reaction was ligated into the PCR2.1-TOPO vector in a TOPO-TA cloning reaction (Invitrogen, Cat. #45-0641) according to manufacturer's instructions and transformed into E. coli TOP10 cells. White to light blue colonies were selected on LB plates containing 100 µg/ml carbenicillin and surface treated with 40 µl of 50 mg/ml X-Gal. Colonies were screened for correct sequence and consistent sense orientation in the vectors. All are in the same relative orientation except for the Scan 7 segment (pMON98376) which is inverted relative to other cloned sequences.

Figure 7:
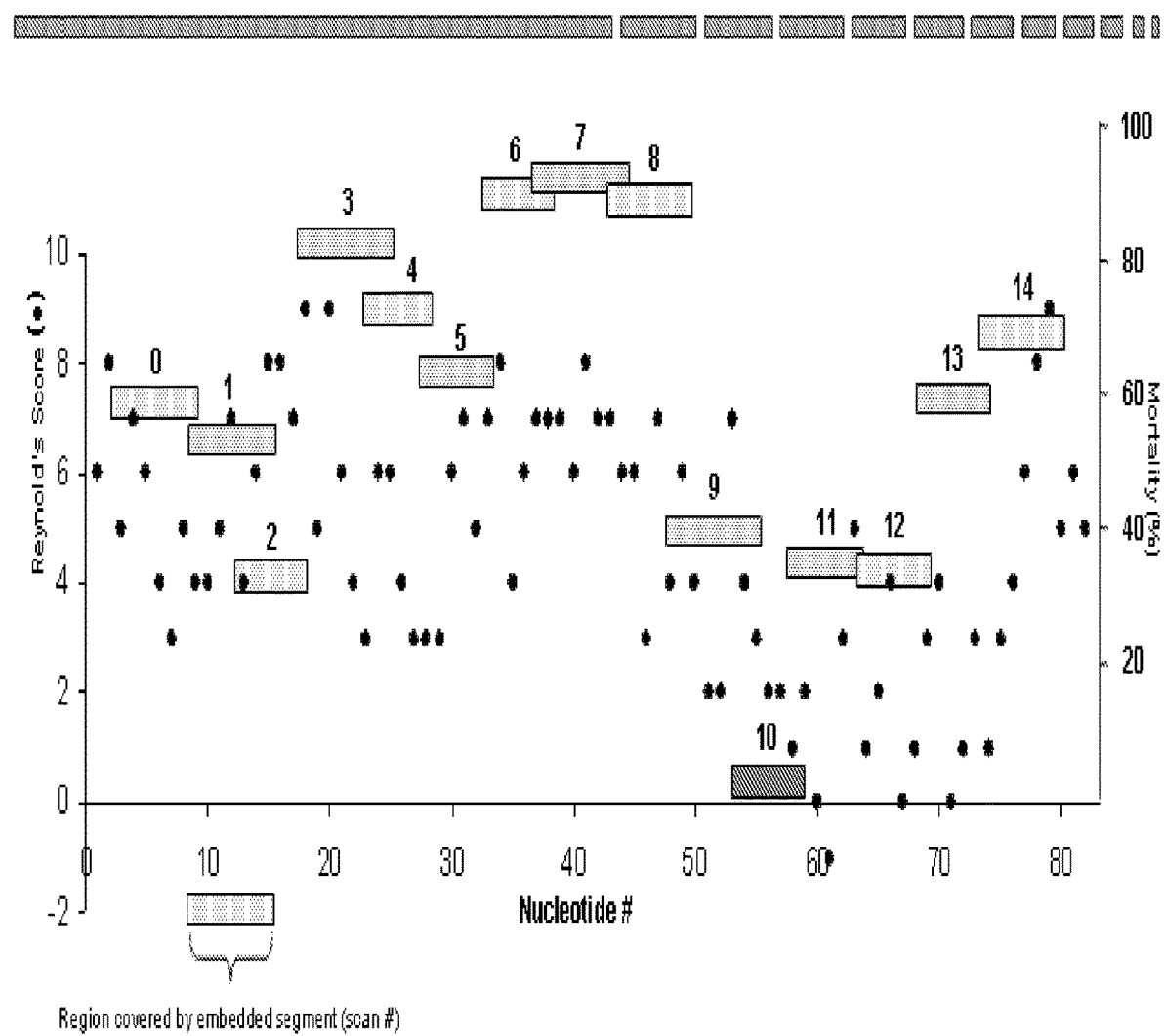
Figure 8:
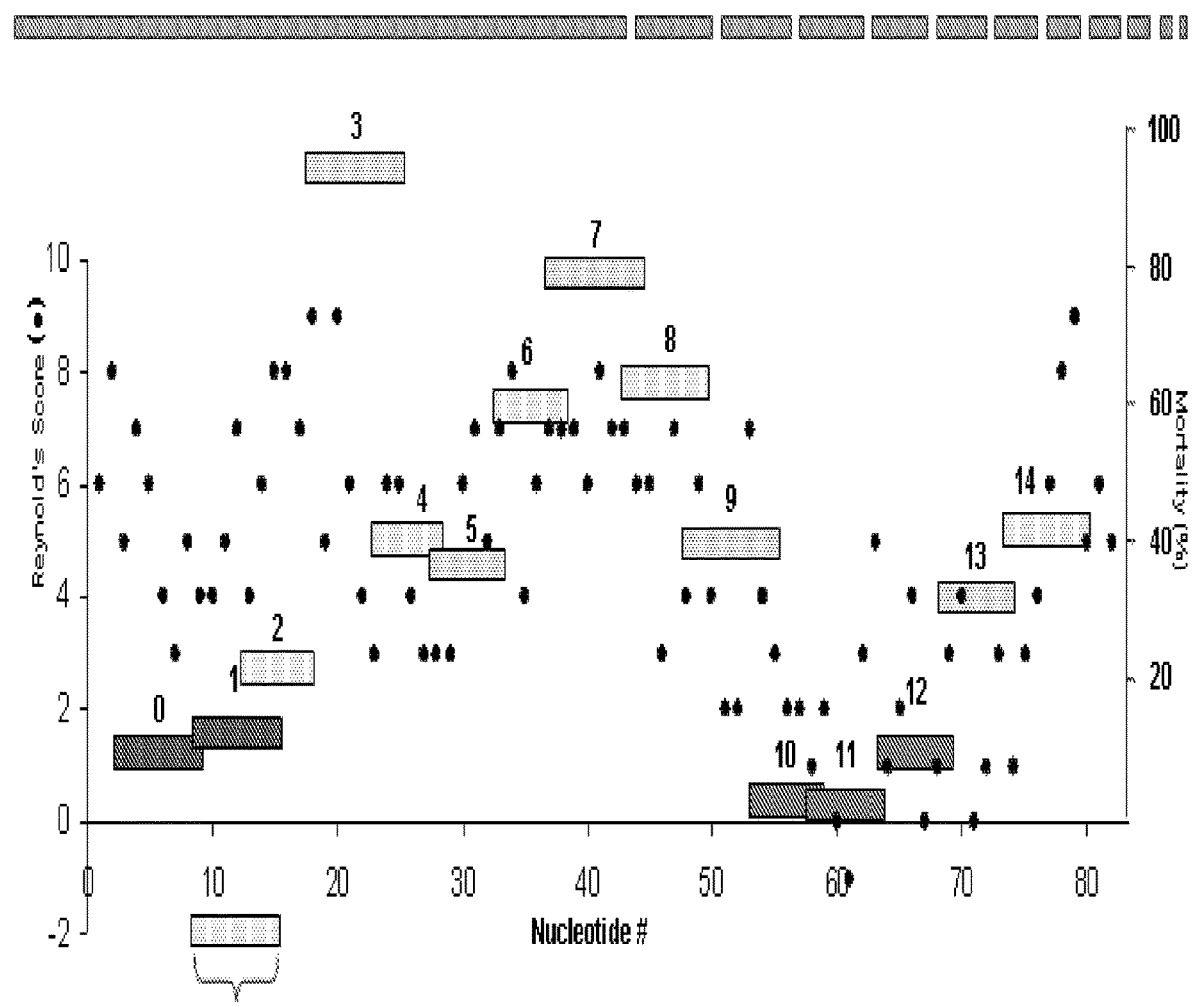

Templates for RNA synthesis were prepared using oligonucleotides pCR2.1-5 and pCR2.1-6 (SEQ ID NO:39-40), the cycling conditions in Table 4, and the same reaction conditions used to amplify the Dv49 100mer template. A blank vector (no corn rootworm sequence), pMON98397, was also amplified to serve as a control for the vector sequences. Fresh PCR product was amplified from verified clones for dsRNA synthesis. Amplifications were visualized on 1-3% agarose gels stained with ethidium bromide to ensure proper size and quality. An aliquot of 5 µl was used in dsRNA synthesis directly from the PCR tube. Synthesis was carried out according to the MEGAscript™ RNAi Kit (Ambion, Cat #1626) with the following alterations: transcription was carried out at 37° C. overnight in a convection oven. Final dsRNA products were quantified by absorption at 260 nm, and visualized on a 1-3% agarose gel to ensure intactness of the product. All samples for insect bioassay were diluted to a final concentration (e.g. 1 ppm) in 10 mM Tris pH 6.8. Twenty µl of each sample were applied to 200 µl of insect diet and allowed to absorb into the diet before addition of a WCR neonate. Stunting and mortality of larvae was scored at day 12.

dsRNA corresponding to the resulting fragments Scan 0 to Scan 14 (FIG. 1) was amplified in a larger neutral carrier (vector backbone sequence), using pCR2.1-5 and pCR2.1-6 oligonucleotides, and dsRNA was synthesized for a total dsRNA length of 206 bp. Since cloning into the pCR2.1-TOPO vector recapitulated the original Dv49 context for some of the cloned 26mer segments, the sequence interrogated for efficacy was actually 27-28 bp in size in some instances. When fed at 1 ppm, the dsRNAs synthesized from the 26mers resulted in a range of mortality from no significant difference from the untreated control to approximately 95% mortality with the scan 7 segment (FIG. 7; Table 5). When fed at 0.2 ppm, the dsRNAs synthesized from the 26mers resulted in a range of mortality from no significant difference from the untreated control to 97% mortality with the scan 3 segment (FIG. 8; Table 5).

The lower dose tested proved useful in discriminating the most active segments. From the dsRNA of each cloned segment of Dv49, several 21 bp siRNAs could potentially result from endogenous WCR DICER activity.

Example 3

Fine Mapping Efficacious Corn Rootworm Gene Targets: 21mer Analysis of Scan 14 Region Twenty one by segments derived from Scan segment 14 of the 26mer analysis were synthesized as above except the ends were modified so that when annealed a Hind III restriction site compatible overhang was created at the 5' end and an Spe I restriction site compatible overhang at the 3' end of each oligonucleotides (SEQ ID NO:41-54). These were ligated into a Hind III/Spe I cut pCR2.1-TOPO backbone. Attempts were made to clone all seven possible 21mer sequences that could be produced from Scan 14. Cloning of Scan 15 failed and the cloned Scan 17 sequence was found to contain a point mutation that is likely responsible for its poor activity. Scan segments 16-21 were amplified to produce templates and dsRNA was prepared as for the 26mer scan. The final size of each dsRNA was 184 bp. Samples were diluted, applied at 0.2 ppm and scored as above.

Figure 9:
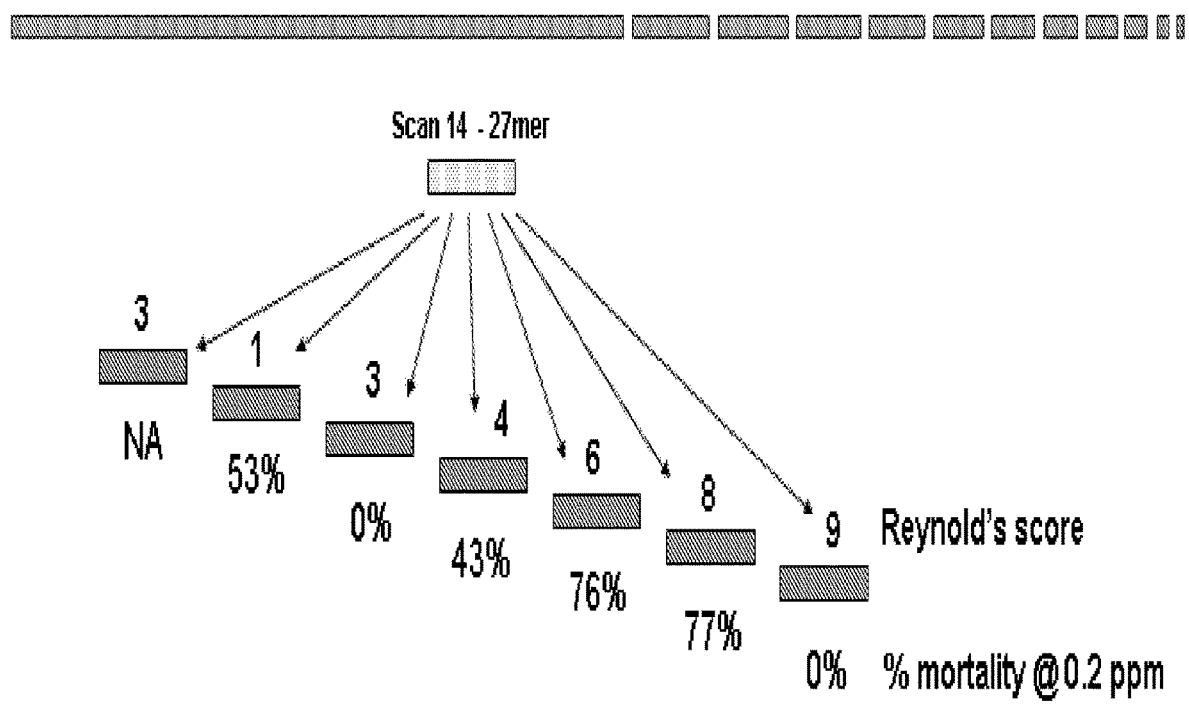

These 21 bp sub-sequences of Scan 14 (Scans 15-21) were tested and most were found to possess significant activity against WCR in diet bio-assay (Table 6; FIG. 9). Generally a higher positive Reynolds score (Reynolds et al. 2004) indicates a greater probability of gene suppression. The noted discrepancies highlight the need for empirical testing in fine mapping efficacy against pest species such as rootworm.

TABLE 6

Impact of dsRNA size on control of WCR in diet bio-assay using 21 bp Dv49 target embedded in vector sequence as carrier. The parental embedded 26 bp sequence from Dv49 (Scan 14) and the 100 bp base sequence were also evaluated. 1 ppm and 0.2 ppm assays were run concurrently. Reynolds scores for 21 bp sequences are indicated.

| dsRNA | Reynolds score | Mortality in WCR diet bio-assay fed at 1 ppm[1] | Mortality in WCR diet bio-assay fed at 0.2 ppm[1] |
|---|---|---|---|
| Scan 14 parent | | 92.0 ± 8.0 * | 77.3 ± 7.6 * |
| Scan 15 | 3 | NA | NA |
| Scan 16 | 1 | 92.1 ± 5.1 * | 53.2 ± 7.9 * |
| Scan 17 | 3 | 13.6 ± 6.0 | 0.0 |
| Scan 18 | 4 | 77.8 ± 10.0 * | 43.2 ± 9.2 * |
| Scan 19 | 6 | 73.3 ± 7.3 * | 76.1 ± 9.6 * |
| Scan 20 | 8 | 85.3 ± 6.2 * | 77.1 ± 7.1 * |
| Scan 21 | 9 | 5.0 ± 5.0 | 0.0 |
| 100 bp Dv49 base sequence | | 97.1 ± 2.9 * | NA |
| Vector sequence only | | 0.0 | NA |

[1]Percent mortality and standard error of the means.
* significantly different from untreated control, P value < 0.05, Planned Contrasts.
NA = not assayed

Example 4

Impact of Dv49 Sequence Polymorphism on Efficacy

The ability to finely map target genes allows an understanding of the impact of sequence variation on efficacy. In FIG. 1, a 100 bp segment of WCR Dv49 used in the 26 bp scan was compared to a number of related sequences from other species (Table 7; SEQ ID NO:2; SEQ ID NO:3; SEQ ID NO:55-72). Sequences for the Dv49 orthologs among *Diabrotica* sp. were found to be highly conserved. From the alignment it is possible to see variation at some locations (e.g. the highly efficacious scan 3 segment), that differs significantly between *Diabrotica* and all other species examined—even other beetle species such as *Tribolium castaneum*. Thus it is possible to make novel chimeric sequences that incorporate small segments (down to siRNA-sized portions) that have high activity and conservation within target *Diabrotica* species but otherwise are poorly conserved outside of this taxonomic group. Such novel sequences could give high activity against *Diabrotica* sp., but low activity against non-target species, even if a species is amenable to RNAi through diet presentation. These may be arranged in novel concatemers that do not create fortuitous matches to other gene sequences via the juxtaposition of subunits (determined by bio-informatic evaluations).

TABLE 7

Gene sequences of animal species acquired from Genbank (accession number listed) or determined through sequencing efforts that have high identity to Dv49 at an amino acid level. Representative sequences (either cDNA or genomic) were used to prepare nucleotide alignments with Dv49. (SEQ ID NO: 2; SEQ ID NO: 3; SEQ ID NOs: 55-72)

| Species | Common Name | Target | Source | SEQ ID NO: |
|---|---|---|---|---|
| *Amphioxus floridae* | Amphioxus | Af49 | BW703594 | 55 |
| *Anopheles gambiae* | mosquito | Ag49 | CR528625 | 56 |
| *Acyrthosiphon pisum* | pea aphid | Ap49 | CN763091 | 57 |
| *Apis mellifera* | honey bee | Am49 | AADG05006126 | |
| *Bombyx mori* | silkworm | Bm49 | AADK01001496 | |
| *Canis familiaris* | dog | Cf49_1 | DN397962 | 58 |
| *Canis familiaris* | dog | Cf49_2 | DN434127 | 59 |
| *Ciona savignyi* | sea squirt | Cs49 | AACT01061660 | |
| *Danio rerio* | zebra fish | Dr49 | CAAK01000381 | |
| *Daphnia magna* | water flea | Dmag49 | BJ928947 | 60 |
| *Diabrotica balteata* | banded cucumber beetle | Dbal49 | | 61 |
| *Diabrotica barberi* | northern corn rootworm | Db49 | | 62 |
| *Diabrotica undecimpunctata* | southern corn rootworm | Du49 | | 63 |
| *Diabrotica virgifera virgifera* | western corn rootworm | Dv49 | | 2 |
| *Diabrotica virgifera zeae* | mexican corn rootworm | Dz49 | | 64 |
| *Drosophila melanogaster* | fruitfly | Dm49 | AABU01002766 | 3 |
| *Fugu rubripes* | puffer fish | Fr49 | BU807180 | 65 |
| *Gallus gallus* | chicken | Gg49 | AJ729228 | 66 |
| *Glossina morsitans* | tsetse fly | Gm49 | BX565926 | 67 |
| *Locusta migratoria* | locust | Lm49 | CO842932 | 68 |
| *Pan troglodytes* | chimpanzee | Pt49_1 | XM_528179 | 69 |
| *Pan troglodytes* | chimpanzee | Pt49_2 | XM_525305 | 70 |
| *Strongylocentrotus purpuratus* | sea urchin | Sp49 | CD309114 | 71 |
| *Tribolium castaneum* | red flour beetle | Tc49 | AAJJ01000852 | |
| *Xenopus laevis* | African clawed frog | Xl49 | BP672793 | 72 |

Small efficacious units such as the scan 3 segment could be vulnerable to nucleotide variation. Natural mutation or pre-existing allelic variation within or between species could reduce the ability to initiate gene suppression targeted against an organism. This potential impact was examined using the sequence corresponding to Dv49, scan segment 3, from *Diabrotica barberi*. This species has a single nucleotide polymorphism when compared to all other *Diabrotica* sp. that were sequenced (FIG. 1). Assay of the Scan 3 segment from *Diabrotica barberi* (Db49 scan 3 segment) revealed it was much less effective than the native *Diabrotica virgifera* scan 3 segment in initiating WCR larval mortality (Table 8). Optimal sequences used for pest RNAi should buffer this potential gene diversity by ensuring that sufficient numbers of highly effective siRNAs can be created from the transgenic construct to target the full range of intended species.

TABLE 8

Impact of Dv49 dsRNA single nucleotide polymorphism on a cloned 26 bp segment (Scan 3) from two *Diabrotica* species when assayed in western corn rootworm bio-assay.

| dsRNA | Mortality in WCR diet bio-assay fed at 1 ppm[1] | Mortality in WCR diet bio-assay fed at 0.2 ppm[1] |
|---|---|---|
| Scan 3 from *Diabrotica virgifera* | 86.3 ± 7.1 * | 91.0 ± 5.6 * |
| Scan 3 from *Diabrotica barberi* | 38.5 ± 5.7 * | 7.3 ± 4.5 |

[1]Percent mortality and standard error of the means.
* significantly different from untreated control, P value < 0.05, Planned Contrasts.

Inspection of alignments of Dv49-related sequences from the organisms listed in Table 7, combined with an analysis of regions within those sequences that may yield efficacious dsRNA (e.g. high Reynolds scores), allows the identification of segments that would likely yield efficacious siRNAs in insect bioassays.

Desirable transgenic RNAi crops would specifically target certain pest species but minimize potential for interactions with unintended species. For instance, ideally one would have a single, simple dsRNA construct that targets a critical gene(s) from *Diabrotica virgifera virgifera* (western corn rootworm, WCR), *Diabrotica virgifera zeae* (Mexican corn rootworm, MCR), and *Diabrotica barberi* (northern corn rootworm, NCR). Additional species, such as *Diabrotica undecimpunctata howardii* (southern corn rootworm, SCR), *Diabrotica undecimpunctata* undecimpunctata (western spotted cucumber beetle); *Diabrotica speciosa*; and *Diabrotica viridula* could also be included among the target species. Selection of gene sequences for inclusion in dsRNA constructs would be optimal with alignments of gene targets from multiple species and populations and also pertinent non-target organisms. cDNA segments coding for Dv49 orthologs from a variety of organisms and populations were sequenced for comparison.

RT-PCR using RNA derived from adults and/or larvae served a source material for obtaining novel sequence. Depending on the target, specific or degenerate primer sets were used to amplify sequences based on information from internal WCR EST libraries and publicly available insect sequences. At least two independent PCR products were examined to develop a consensus for each sequence.

In some instances, alleles were observable in the amplification products from multiple individuals. Alleles were also discernable from sequences present in the EST collections themselves when multiple overlapping ESTs were present for a given sequence. In these instances degenerate nucleotide designations were specified. These degeneracies do not denote ambiguous sequencing reads. Sequencing of target segments from multiple regional representatives of selected species may be performed in order to understand allelic variation on a regional scale.

In general, sequence identity corresponded to previously observed phylogenetic relationships (e.g. Clark et al., 2001). WCR and MCR are closely related and NCR, also in the *virgifera* species group, bears many common stretches of identity. SCR and BCB are clearly more distinctive as members of the *fucata* species group. Each *Diabrotica* spp. exhibits unique small nucleotide polymorphisms (SNPs). If any of the SNPs fall into critical regions that give rise to efficacious siRNAs, they may affect efficacy of a given sequence used in a dsRNA construct. This may become important if a limited target sequence set is employed, for example on the order of one or a small number of efficacious siRNAs in a dsRNA construct. Having sequence available allows informed choices for target sequences in dsRNA constructs. These must however be validated for efficacy in bio-assay.

Examination of target sequences from related *Diabrotica* spp., such as BCB and SCR, may also help to determine likely polymorphic regions amongst relatively closely related species of diabroticine beetles when sequence information is not available.

Example 5

Polymorphisms in Other Target Sequences

Sequences from additional target genes were also obtained. These target sequences included putative orthologs of the following genes: mov34 (Flybase CG3416; SEQ ID NO:107-109); Na/K-exchanging ATPase (Flybase CG9261; SEQ ID NO:110-114); ribosomal protein L19 (Flybase CG2746; SEQ ID NO:115-118); RNA polymerase (Flybase CG3180; SEQ ID NO:119-121); ribosomal protein S9 (Flybase CG3395; SEQ ID NO:122-125); v-ATPase subunit 2 (Flybase CG3762; SEQ ID NO:126-135), in addition to carrier protein Flybase CG8055 orthologs (SEQ ID NO:2; SEQ ID NO:3; SEQ ID NO:61-64). Sequence comparisons were performed. The sequence relationships between orthologs of Flybase CG9261 in the different beetle species (FIG. 2) allowed a phylogenetic comparison (FIG. 3), which differentiates the virgifera group from the fucata group. These sequences extend the number of sequences that may be utilized in designing optimal segments for use in RNAi and other applications.

Example 6

Figure 6:
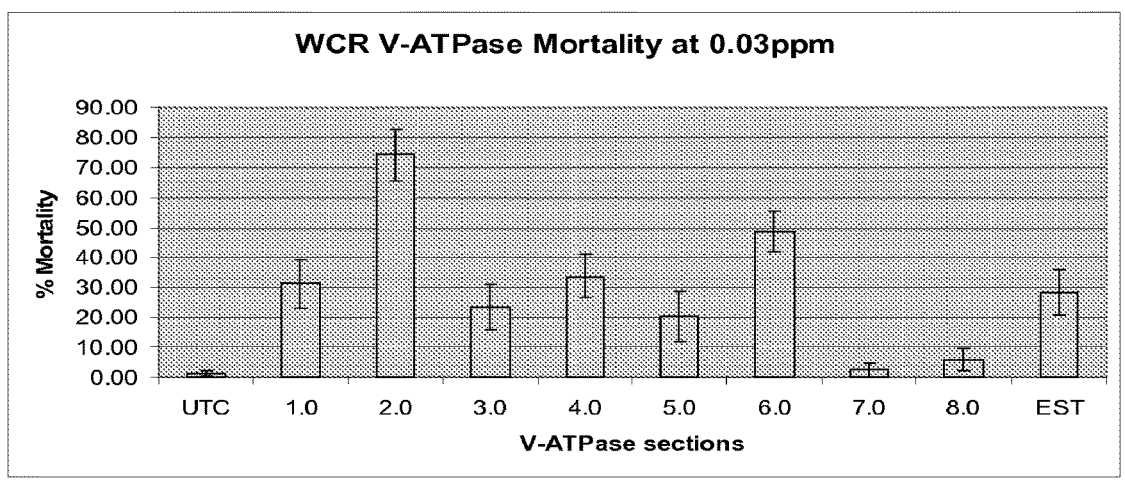

Mapping Efficacious Corn Rootworm Gene Targets: 26mer Analysis of V-ATPase Subunit A A 100 bp segment of *Diabrotica virgifera* V-ATPase subunit A was chosen for detailed efficacy mapping in a manner similar to that used to scan across a 100 bp segment of Dv49. This 100 bp segment was taken from a larger region that showed high efficacy at a discriminating dose (FIG. 6). This 100 bp region had multiple potential siRNAs with high predicted Reynolds scores and low secondary structure. Oligonucleotide pairs (vATP100-1 and vATP100-2; vATP100-3 and vATP100-4 (SEQ ID NO:73-76) were synthesized to allow amplification of template for sense or anti-sense strand transcripts. The transcript strands can then be annealed to create a 100 bp dsRNA.

Twenty-six by segments were selected for fine mapping efficacy, tiling across the base sequence in 5 bp register. Oligonucleotides for each were synthesized as sense and anti-sense pairs (vATP_26-1 to vATP_26-30; SEQ ID NO:77-106). After annealing, the duplexes are cloned via sticky-end ligation using nucleotides added for annealing with Spe I/Eco RI cut vector (pCR2.1-TOPO). Once clones are sequence verified, templates for dsRNA synthesis are prepared using oligonucleotides pCR2.1-5 and pCR2.1-6, as for Dv49 scan in Example 2. The resulting embedded segments comprising candidate target sequences are assayed by WCR diet bio-assay for efficacy. Nucleotide sequences that encode potent siRNA derived from *Diabrotica virgifera* V-ATPase subunit A may be included with sequences derived, for instance, from *Diabrotica virgifera* Dv49, in an RNAi expression construct to yield a dsRNA-encoding construct which exhibits multiple modes of action in suppressing growth and development of the target organism.

TABLE 9

Oligonucleotides to allow amplification of a 100 bp segment of *Diabrotica virgifera* V-ATPase subunit A. T7 RNA polymerase promoters have been incorporated (lower case) (SEQ ID NOs: 73-76).

| Name | Sequence | Target DNA | Orientation | Comments |
|---|---|---|---|---|
| vATP100-1 | taatacgactcactatagGACTTCAACCCAATCAAC | V-ATPAse subunit A | sense | for amplifying sense template to make 100mer segment of WCR V-ATPase |
| vATP100-2 | GAATCATTTTGTGTTTGACAAGG | V-ATPAse subunit A | anti-sense | for amplifying sense template to make 100mer segment of WCR V-ATPase |
| vATP100-3 | GACTTCAACCCAATCAACATC | V-ATPAse subunit A | sense | for amplifying anti-sense template to make 100mer segment of WCR V-ATPase |
| vATP100-4 | taatacgactcactatagGAATCATTTTGTGTTTGAC | V-ATPAse subunit A | anti-sense | for amplifying anti-sense template to make 100mer segment of WCR V-ATPase |

TABLE 10

Oligonucleotides to allow cloning of 26 bp segments from *Diabrotica virgifera* V-ATPase subunit A (lower case). Upper case indicates restriction site overhangs incorporated to facilitate cloning (SEQ ID NOs: 77-106).

| Oligonucleotide | Sequence | Cloned Duplex Product | Orientation |
|---|---|---|---|
| vATP_26-1 | CTAGTgacttcaacccaatcaacatcaagttG | Scan 1 | sense |
| vATP_26-2 | AATTCaacttgatgttgattgggttgaagtcA | | anti-sense |
| vATP_26-3 | CTAGTcaacccaatcaacatcaagttgggatG | Scan 2 | sense |
| vATP_26-4 | AATTCatcccaacttgatgttgattgggttgA | | anti-sense |
| vATP_26-5 | CTAGTcaatcaacatcaagttgggatctcacG | Scan 3 | sense |
| vATP_26-6 | AATTCgtgagatcccaacttgatgttgattgA | | anti-sense |
| vATP_26-7 | CTAGTaacatcaagttgggatctcacttaacG | Scan 4 | sense |
| vATP_26-8 | AATTCgttaagtgagatcccaacttgatgttA | | anti-sense |

TABLE 10-continued

Oligonucleotides to allow cloning of 26 bp segments from *Diabrotica virgifera* V-ATPase subunit A (lower case). Upper case indicates restriction site overhangs incorporated to facilitate cloning (SEQ ID NOs: 77-106).

| Oligonucleotide | Sequence | Cloned Duplex Product | Orientation |
|---|---|---|---|
| vATP_26-9 | CTAGTcaagttgggatctcacttaactggagG | Scan 5 | sense |
| vATP_26-10 | AATTCctccagttaagtgagatcccaacttgA | | anti-sense |
| vATP_26-11 | CTAGTtgggatctcacttaactggaggtgatG | Scan 6 | sense |
| vATP_26-12 | AATTCatcacctccagttaagtgagatcccaA | | anti-sense |
| vATP_26-13 | CTAGTtctcacttaactggaggtgatatataG | Scan 7 | sense |
| vATP_26-14 | AATTCtatatatcacctccagttaagtgagaA | | anti-sense |
| vATP_26-15 | CTAGTcttaactggaggtgatatatatggtcG | Scan 8 | sense |
| vATP_26-16 | AATTCgaccatatatatcacctccagttaagA | | anti-sense |
| vATP_26-17 | CTAGTctggaggtgatatatatggtctagttG | Scan 9 | sense |
| vATP_26-18 | AATTCaactagaccatatatatcacctccagA | | anti-sense |
| vATP_26-19 | CTAGTggtgatatatatggtctagttcatgaG | Scan 10 | sense |
| vATP_26-20 | AATTCtcatgaactagaccatatatatcaccA | | anti-sense |
| vATP_26-21 | CTAGTtatatatggtctagttcatgaaaacaG | Scan 11 | sense |
| vATP_26-22 | AATTCtgttttcatgaactagaccatatataA | | anti-sense |
| vATP_26-23 | CTAGTatggtctagttcatgaaaacacccttG | Scan 12 | sense |
| vATP_26-24 | AATTCaagggtgttttcatgaactagaccatA | | anti-sense |
| vATP_26-25 | CTAGTctagttcatgaaaacacccttgtcaaG | Scan 13 | sense |
| vATP_26-26 | AATTCttgacaagggtgttttcatgaactagA | | anti-sense |
| vATP_26-27 | CTAGTtcatgaaaacacccttgtcaaacacaG | Scan 14 | sense |
| vATP_26-28 | AATTCtgtgtttgacaagggtgttttcatgaA | | anti-sense |
| vATP_26-29 | CTAGTaaaacacccttgtcaaacacaaaatgG | Scan 15 | sense |
| vATP_26-30 | AATTCcattttgtgtttgacaagggtgttttA | | anti-sense |

Example 7

Optimizing Transgenes for Gene Suppression

Knowledge about variation within target and non-target species may also be incorporated to choose those siRNA-sized regions that most specifically target the pests of interest while minimizing SNP variation that could reduce effectiveness. As plant produced siRNAs originating from known transgenes are cloned, and efficacy is confirmed by bioassay, any differences in effective siRNA production between crop and pest species given the same base target sequence may become apparent. Those sequences that effectively suppress gene expression in target insects, and have reduced capacity to initiate transgene suppression in planta (to help prevent transgene silencing and dicing within the transgenic plant), may be selected for further analysis. Additionally, identification of effective and ineffective siRNAs allows further optimization of constructs. If UTRs or other expression elements are chosen for inclusion in a transgene construct coding for dsRNA, choosing those elements with minimal potential to produce effective siRNAs may be desired. This could be extended to coding regions when codon optimization is performed, resulting in reduction in the potential for effective siRNA production or matches to endogenous miRNAs, unless such siRNA were desired.

Example 8

Engineering Stable Expression of dsRNA

After selecting a pest RNAi target, one or more corresponding dsRNA segments is stably expressed via a transgene in planta. The goal is production of a primary transcript that ultimately yields effective siRNAs when consumed by the targeted pest, but has a reduced propensity to undergo post-transcriptional gene silencing (PTGS) because the transgene has the sequences that give rise to siRNA disrupted through intron placement (e.g. illustrated in FIGS. 4-5).

Additional sequence such as 5' and 3' untranslated regions (UTRs) and "filler" (to make exons of at least minimal required size for plant processing) can be produced by combining sequences (e.g. direct tandem sense sequence) that do not elicit effective siRNAs. The efficacy can be determined by practical evaluation of these in bio-assay or through the use of predictive tools (e.g. Reynolds scores) that consider biophysical parameters that a common to effective or ineffective siRNAs.

Such construct designs could result from identification of small regions exhibiting high efficacy against pest species. Regions that give rise to potent siRNAs may be disrupted by introns such as small segments of the natural gene target order or synthetic arrangements such as overlapping siRNAs as illustrated in FIG. 5. Additional exon sequences and UTRs could be created from sequence that does not give rise to productive siRNAs (i.e. those sequences shown in bio-assay or via predictive algorithms to be poorly utilized by the RNA-induced silencing complex (RISC) (Hammond et al., 2000). Because the engineered transgene is distinct from the processed transcript as a result of disrupting the continuity of potential siRNAs, such an arrangement could result in a reduced potential to silence the transgene, including methylation and eventual transcriptional silencing via the RNA-induced initiation of transcriptional gene silencing (RITS) complex (Verdel et al. 2004). The presence of introns in the primary transcript may also slow overall processing and potentially increase the longevity of the larger primary dsRNA transcript, thus enhancing uptake potential. Other designs for stabilizing "large" dsRNAs (e.g. inclusion of a nucleolar targeting sequence) would be compatible with this style of transgene construction.

Additional target sequences are added by extending the primary transcriptional unit with one or more additional introns and exons designed as above so that a longer dsRNA transcript could be created. Overlapping potent siRNAs and placing the intron within the overlap could expand the number of potential target sequences while minimizing the number of required introns within the construct.

REFERENCES

The references listed below are incorporated herein by reference to the extent that they supplement, explain, provide a background for, or teach methodology, techniques, and/or compositions employed herein.

U.S. Pat. No. 4,536,475; U.S. Pat. No. 4,693,977; U.S. Pat. No. 4,876,197; U.S. Pat. No. 4,880,734; U.S. Pat. No. 4,886,937; U.S. Pat. No. 4,940,838; U.S. Pat. No. 4,959,317; U.S. Pat. No. 5,015,580; U.S. Pat. No. 5,107,065; U.S. Pat. No. 5,110,732; U.S. Pat. No. 5,231,020; U.S. Pat. No. 5,283,184; U.S. Pat. No. 5,302,523; U.S. Pat. No. 5,384,253; U.S. Pat. No. 5,464,763; U.S. Pat. No. 5,464,765; U.S. Pat. No. 5,501,967; U.S. Pat. No. 5,508,184; U.S. Pat. No. 5,527,695; U.S. Pat. No. 5,538,880; U.S. Pat. No. 5,550,318; U.S. Pat. No. 5,563,055; U.S. Pat. No. 5,591,616; U.S. Pat. No. 5,593,874; U.S. Pat. No. 5,633,435; U.S. Pat. No. 5,693,512; U.S. Pat. No. 5,698,425; U.S. Pat. No. 5,712,135; U.S. Pat. No. 5,759,829; U.S. Pat. No. 5,780,708; U.S. Pat. No. 5,789,214; U.S. Pat. No. 5,804,693; U.S. Pat. No. 5,824,877; U.S. Pat. No. 5,837,848; U.S. Pat. No. 5,981,840; U.S. Pat. No. 6,118,047; U.S. Pat. No. 6,160,208; U.S. Pat. No. 6,326,193; U.S. Pat. No. 6,384,301; U.S. Pat. No. 6,399,861; U.S. Pat. No. 6,403,865; U.S. Pat. No. 6,506,599; U.S. Pat. No. 6,551,962

U.S. Prov. Appln. 60/772,736
US Publn. 2003/0018993; US Publn. 2003/0061626; US Publn. 2003/0150017; US Publn. 2003/0175965; US Publn. 2002/0048814
U.S. Ser. No. 10/465,800
EP 0 120 516; EP 0 122 791; EP 0 127,328; EP 0 284044; EP 0 3215447
PCT Appln. WO 97/32016; PCT Appln. WO 99/49029; PCT Appln. WO 99/53050; PCT Appln. WO94/01550; PCT Appln. WO98/05770; PCT Appln. PCTUS2006033867
Altschul et al., *J. Mol. Biol.*, 215:403-410, 1990.
Arziman et al. 2005. *Nucl. Acids Res.* 33:W582-W588.
Ausubel et al. eds., *Protocols in Molecular Biology*, Second Edition, John Wiley & Sons, 1992
Bettencourt et al., 2002. *Insect Mol. Biol.* 11:267-271.
Bevan et al. 1984. *Nucl. Acids Res.* 12:8711-8721
Bevan et al., *Nucleic Acids Res.*, 11(2):369-385, 1983.
Botstein et al., *Gene*, 8:17-24, 1979.
Brake et al., *Proc. Natl. Acad. Sci. USA*, 81(15):4642-4646, 1984.
Broothaerts et al., *Nature*, 433:629-633, 2005.
Brutlag et al., *Computers and Chemistry*, 17:203-207, 1993.
Bucher et al., 2002. *Curr. Biol.* 12:R85-R86.
Busk et al., *Plant J.*, 11(6):1285-1295, 1997.
Carthew, 2001. *Curr. Opinion Genet. Devel.*, 13:244-248.
Clark et al., 2001. *Insect Mol. Biol.* 10:303-314
Clark et al., *Blood*, 98:2887-2893, 2001.
Cogoni, and Macino. 2000. *Genes Dev* 10:638-643.
Current Protocols in Molecular Biology, Ausubel et al. (Eds.), Greene Publishing and Wiley-Interscience, NY, 1989.
Dellaporta et al., In: *Chromosome Structure and Function: Impact of New Concepts*, 18th Stadler Genetics Symposium, 11:263-282, 1988.
deMaagd et al., 2003. *Annu. Rev Genet* 37: 409-433.
Elbashir et al., *Methods*, 26:199-213, 2002.
Feinberg and Hunter. 2003. *Science*. 301:1545-7
Fire et al. 1998. *Nature*. 391:806-11
Gruber et al., In: *Vectors for Plant Transformation*, Glick and Thompson (Eds.), CRC Press, Inc., Boca Raton, 89-119, 1993.
Hamilton and Baulcombe, *Science*, 286(5441):950-952, 1999.
Hammond et al., 2000. *Nature* 404:293-296
Hannon et al., *J. Mol. Neurosci.*, 18(1-2):15-27, 2002.
Haymes et al., In: *Nucleic Acid Hybridization, A Practical Approach*, IRL Press, Washington, D.C., 1985
Herr 2005. *FEBS Lett.* 579:5879-88
Herrera-Estrella et al., *Nature*, 303:209-213, 1983.
Hirel et al., *Plant Molecular Biology*, 20:207-218, 1992.
Horsch et al., *Science*, 227:1229, 1985.
Ikatu et al., *Bio/Technol.*, 8:241-242, 1990.
Jefferson et al., *Biochem. Soc. Trans.*, 15:7-19, 1987.
Jefferson et al., *EMBO J.*, 6:3901-3907, 1987.
Kaeppler et al., *Plant Cell Reports*, 9:415-418, 1990.
Katz et al., *J. Gen. Microbiol.*, 129:2703-2714, 1983.
Klee et al., *Bio-Technology*, 3(7):637-642, 1985.
Miki et al., In: *Methods in Plant Molecular Biology and Biotechnology*, Glick and Thompson (Eds.), CRC Press, 67-88, 1993.
Moloney et al., *Plant Cell Reports*, 8:238, 1989.
Myanohara et al., *Proc. Natl. Acad. Sci. USA*, 80(1):1-5, 1983.
Napoli et al., 1990. *Plant Cell* 2:279-289.
Odell et al., *Nature*, 313:810-812, 1985.
Orr-Weaver et al., *Proc. Natl. Acad. Sci. USA*, 80(14):4417-4421, 1983.
Ow et al., *Science*, 234:856-859, 1986.

Padgette et al., *Crop Sci.*, 35:1451-1461, 1995.
Potrykus et al., *Mol. Gen. Genet.*, 199(2):169-177, 1985.
Reynolds et al. 2004. *Nat Biotechnol.* 22:326-330.
Rine et al., *Proc. Natl. Acad. Sci. USA,* 80(22):6750-6754. 1983.
Sambrook et al. 1989. *Molecular Cloning: a Laboratory Manual:* 2nd edition, Cold Spring Harbor Laboratory Press
Stahl et al., *BMC Biotechnol.,* 4:31, 2004.
Stinchcomb et al., *J. Mol. Biol.,* 158(2):157-190, 1982.
Sutcliffe et al., *Proc. Natl. Acad. Sci. USA,* 75:3737-3741, 1978.
Uhlirova et al., 2003. *PNAS* 100: 15607-15613.
Van Heeke and Schuster, *J. Biol. Chem.,* 264(33):19475-19477, 1989.
Verdel et al., 2004. *Science* 303:672-676.
Voinnet. 2005. *FEBS Lett.* 579:5858-71.
Wassenegger et al. 1994. *Cell* 76:567-576.
Wesley et al. 2001. *Plant J.* 27:581-590.
Winston, et al. 2002. *Science* 295: 2456-2459.
Yuan, et al., 2004. *Nucl. Acids Res.* 32:W130-W134;
Zilberman et al., 2004. *Curr. Biol.* 14:1214-1220.
Zukowsky et al., *Proc. Natl. Acad. Sci. USA,* 80:1101-1105, 1983.

What is claimed is:

1. A method of increasing an insect crop pest inhibitory activity of a dsRNA, comprising:
   a) obtaining a first nucleic acid segment that when expressed as a first dsRNA and taken up by the insect crop pest inhibits feeding by the insect crop pest or progeny thereof;
   b) linking the first nucleic acid segment to a second nucleic acid segment to create a third nucleic acid segment that is expressed as a third dsRNA, wherein the second nucleic acid segment is a neutral carrier sequence and does not inhibit feeding by the insect crop pest or progeny thereof when expressed as a dsRNA, and wherein the third dsRNA exhibits increased potency of inhibition of feeding by the insect crop pest or progeny thereof relative to the first dsRNA alone, wherein the third nucleic acid segment comprises at least 80 bases; and
   c) expressing the third nucleic acid segment in a plant or plant cell,
   wherein the insect crop pest is a *Diabrotica* spp.

2. The method of claim 1, wherein the first nucleic acid segment is obtained by a method comprising the steps of:
   I) obtaining a starting nucleic acid molecule that when expressed as a dsRNA and taken up by the insect crop pest inhibits feeding by the insect crop pest or progeny thereof; and
   II) selecting at least a first portion of the starting nucleic acid molecule that inhibits feeding by the insect crop pest or a progeny thereof following uptake of a dsRNA expressed from said portion; and
   III) employing the portion as said the first nucleic acid segment in step a).

3. The method of claim 2, wherein the starting nucleic acid molecule is a cDNA.

4. The method of claim 2, wherein step II) comprises preparing a series of overlapping or consecutive portions from the starting nucleic acid molecule and identifying from said portions at least a first portion that inhibits feeding by the insect crop pest or a progeny thereof when expressed as a dsRNA and taken up by the insect crop pest.

5. The method of claim 1, further comprising producing a recombinant vector comprising a first, a second and a third polynucleotide sequence, wherein the first polynucleotide sequence comprises the third nucleic acid segment and wherein the third polynucleotide sequence is linked to the first polynucleotide sequence by the second polynucleotide sequence, and wherein the third polynucleotide sequence is the reverse complement of the first polynucleotide sequence such that the first and the third polynucleotide sequences hybridize when transcribed into a ribonucleic acid to form the double stranded ribonucleotide molecule stabilized by the linked second ribonucleotide sequence.

6. The method of claim 1, wherein the second nucleotide segment is not complementary to a nucleotide sequence of the insect crop pest.

7. The method of claim 1, wherein one or both of the first nucleic acid segment and the third nucleic acid segment comprises an intron.

8. The method of claim 7, comprising introducing an intron into said first nucleic acid segment.

9. The method of claim 1, wherein the first nucleic acid segment comprises 19 to 80, 19 to 50, or 21 to 30 contiguous bases complementary to a coding sequence of the insect crop pest.

10. An expression construct comprising the third nucleic acid segment prepared according to the method of claim 1 and the reverse complement thereof operably linked to a promoter.

11. A method of controlling feeding by the insect crop pest or progeny thereof on a plant comprising introducing into the plant cell the expression construct of claim 10.

12. The third dsRNA prepared according to the method of claim 1, wherein the third dsRNA is a recombinant dsRNA.

13. A plant cell transformed with the expression construct of claim 10.

14. A transgenic plant comprising the expression construct of claim 10.

15. A method of producing an expression construct for expressing a dsRNA with increased specificity of the insect crop pest inhibitory activity comprising:
   a) obtaining a starting nucleic acid molecule complementary to at least a first coding sequence of the insect crop pest;
   b) selecting a region within the starting nucleic acid molecule that when expressed as a dsRNA inhibits feeding by the insect crop pest or progeny thereof following uptake of the dsRNA expressed from the region by the insect crop pest;
   c) linking the region to a second nucleic acid molecule that is a neutral carrier sequence to create a third nucleic acid molecule, wherein the third nucleic acid molecule comprises at least 80 bases;
   d) producing an expression construct, wherein the second nucleic acid molecule when expressed as a dsRNA does not inhibit feeding by the insect crop pest or progeny thereof following uptake of the dsRNA, wherein the third nucleic acid molecule when expressed as a dsRNA exhibits increased potency of inhibition of feeding by the insect crop pest or progeny thereof relative to the dsRNA expressed from the region,
wherein the insect crop pest is a *Diabrotica* spp.

16. The method of claim 15, wherein selecting a region within the starting molecule comprises screening a series of overlapping or consecutive regions from the starting nucleic acid molecule and identifying from said regions at least a first region that inhibits feeding by the insect crop pest or a progeny thereof when expressed as a dsRNA and taken up by the insect crop pest.

17. The method of claim 15, wherein the starting nucleic acid molecule is a cDNA from the insect crop pest.

18. The method of claim 15, wherein the insect crop pest is selected from the group consisting of: *D. virgifera virgifera; D. virgifera* zeae; *D. undecimpunctata; D. balteata; D. barberi;* and *D. speciosa.*

19. The method of claim 15, wherein the region comprises from 19 bp to 50 bp complementary to a coding sequence of the insect crop pest.

20. The method of claim 19, wherein the region comprises from 21 bp to 30 bp complementary to a coding sequence of the by the insect crop pest.

21. The method of claim 15, comprising identifying at least a second region within the starting molecule that when expressed as a dsRNA inhibits feeding by the by the insect crop pest or progeny thereof and linking the second region to the second nucleic acid molecule or a third nucleic acid molecule that when expressed as a dsRNA does not inhibit feeding by the insect crop pest or progeny thereof following uptake of the dsRNA expressed from the third nucleic acid molecule by the insect crop pest.

22. The method of claim 15, wherein the region is not complementary to a nucleic acid of a non-insect target crop pest.

23. The method of claim 15, wherein the region is complementary to a nucleic acid unique to the species in which the insect crop pest is classified.

24. The method of claim 15, wherein the region is complementary to a nucleic acid unique to the genus in which the insect crop pest is classified.

25. The method of claim 15, wherein the region is unique to *Diabrotica* spp.

26. The method of claim 25, wherein the region is unique to a *Diabrotica* spp. selected from the group consisting of *Diabrotica undecimpunctata howardii* (Southern Corn Rootworm (SCR)), *Diabrotica virgifera virgifera* (Western Corn Rootworm (WCR)), *Diabrotica barberi* (Northern Corn Rootworm (NCR)), *Diabrotica virgifera* zeae (Mexican Corn Rootworm (MCR)), *Diabrotica balteata, Diabrotica viridula,* and *Diabrotica speciosa* (Brazilian Corn Rootworm (BZR)).

27. A method of controlling feeding by the insect crop pest or progeny thereof on a plant comprising introducing into the plant an expression construct prepared by the method of claim 15.

28. A plant cell transformed with an expression construct prepared by the method of claim 15.

29. A method of enhancing the control of an insect crop pest in a plant comprising expressing in the cells of the plant at least two dsRNA sequences that function upon uptake by the pest to inhibit the expression of at least a first target coding sequence within the insect crop pest, wherein the two dsRNA sequences are complementary to two non-contiguous portions of the first target coding sequence or to two different coding sequences of the insect crop pest, and wherein at least one of the two dsRNA sequences comprises a neutral carrier sequence and is at least 80 bases,
wherein the insect crop pest is a *Diabrotica* spp.

30. The method of claim 29, wherein at least one of the two dsRNA sequences comprises 19 bp to 80 bp, 19 bp to 50 bp, or 21 bp to 30 bp.

31. The method of claim 29, wherein the two dsRNA sequences are complementary to at least two target coding sequences of the insect crop pest.

32. The method of claim 31, further comprising expressing in the cells of the plant at least a third dsRNA sequence that functions upon uptake by the insect crop pest to inhibit the expression of a third target coding sequence within the by the insect crop pest, wherein the third dsRNA sequence is complementary to a portion of the third target coding sequence.

33. The method of claim 29, wherein the two dsRNA sequences are expressed from regions selected from a starting nucleic acid molecule that when expressed as a dsRNA inhibits feeding by the insect crop pest or progeny thereof following uptake of the dsRNA by the insect crop pest.

34. The method of claim 33, wherein the starting nucleic acid molecule is a cDNA from the insect crop pest.

35. The method of claim 29, further comprising expressing a polynucleotide sequence in the cell selected from the group consisting of a patatin, a *Bacillus thuringiensis* insecticidal protein, a *Xenorhabdus* insecticidal protein, a *Photorhabdus* insecticidal protein, a *Bacillus laterosporus* insecticidal protein, and a *Bacillus sphaericus* insecticidal protein.

36. The method of claim 35, wherein the *Bacillus thuringiensis* insecticidal protein is selected from the group consisting of a Cry1, a Cry3, a TIC851, a CryET70, a Cry2, ET29, ET37, a binary insecticidal protein CryET33 and CryET34, a binary insecticidal protein CryET80 and CryET76, a binary insecticidal protein TIC100 and TIC101, a binary insecticidal protein ET29 and TIC810, a binary insecticidal protein ET37 and TIC812, and a binary insecticidal protein PS149B1.

37. The method of claim 29, wherein the target coding sequence encodes a protein, the predicted function of which is selected from the group consisting of muscle formation, juvenile hormone formation, juvenile hormone regulation, ion regulation and transport, digestive enzyme synthesis, maintenance of cell membrane potential, feeding site formation, feeding site development, feeding site maintenance, infection, molting, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis.

38. The method of claim 31, wherein the two target coding sequences perform at least two functions essential for the insect crop pest survival that are suppressed by the dsRNA sequences, the functions being selected from the group consisting of feeding by the pest, cell apoptosis, cell differentiation and development, capacity or desire for sexual reproduction, muscle formation, muscle twitching, muscle contraction, juvenile hormone formation, juvenile hormone regulation, ion regulation and transport, maintenance of cell membrane potential, amino acid biosynthesis, amino acid degradation, sperm formation, pheromone synthesis, pheromone sensing, antennae formation, wing formation, leg formation, egg formation, larval maturation, digestive enzyme formation, haemolymph synthesis, haemolymph maintenance, neurotransmission, larval stage transition, pupation, emergence from pupation, cell division, energy metabolism, respiration, and formation of cytoskeletal structure.

39. The method of claim 29, wherein the insect crop pest is a corn rootworm selected from the group consisting of *Diabrotica undecimpunctata howardii* (Southern Corn Rootworm (SCR)), *Diabrotica virgifera virgifera* (Western Corn Rootworm (WCR)), *Diabrotica barberi* (Northern Corn Rootworm (NCR)), *Diabrotica virgifera* zeae (Mexican Corn Rootworm (MCR)), *Diabrotica balteata, Diabrotica viridula,* and *Diabrotica speciosa* (Brazilian Corn Rootworm (BZR)).

* * * * *